US006552188B2

(12) United States Patent
Kodama et al.

(10) Patent No.: US 6,552,188 B2
(45) Date of Patent: Apr. 22, 2003

(54) UNSYMMETRICAL CYCLIC DIAMINE COMPOUND

(75) Inventors: Tatsuhiko Kodama, Setagaya-ku (JP); Masahiro Tamura, Higashimurayama (JP); Toshiaki Oda, Higashimurayama (JP); Yukiyoshi Yamazaki, Higashimurayama (JP); Masahiro Nishikawa, Higashimurayama (JP); Shunji Takemura, Hachioji (JP); Takeshi Doi, Higashimurayama (JP); Yoshinori Kyotani, Higashiyamato (JP)

(73) Assignee: Kowa Co., Ltd., Nagoya (JP)

(*) Notice: Subject to any disclaimer, the term of this patent is extended or adjusted under 35 U.S.C. 154(b) by 0 days.

(21) Appl. No.: 09/893,699

(22) Filed: Jun. 29, 2001

(65) Prior Publication Data
US 2003/0022887 A1 Jan. 30, 2003

(51) Int. Cl.[7] .................. A61K 31/496; A61K 31/551; C07D 241/04; C07D 243/08; C07D 401/06

(52) U.S. Cl. ................ 540/575; 544/295; 544/360; 544/386; 544/391; 514/218; 514/253.01

(58) Field of Search .............. 514/253.01, 218; 544/360, 295, 386, 391; 540/575

(56) References Cited

FOREIGN PATENT DOCUMENTS

| JP | 9-143075 | 6/1997 |
|---|---|---|
| JP | 10-67656 | 3/1998 |
| JP | 10-147568 | 6/1998 |
| JP | 10-182550 | 7/1998 |
| JP | 11-92382 | 4/1999 |
| JP | 2000-86641 | 3/2000 |
| JP | 2000-509070 | 7/2000 |
| JP | 2000-319277 | 11/2000 |

OTHER PUBLICATIONS

Y. Ohkawara, et al., "In Situ Expression of the Cell Adhesion Molecules in Bronchial Tissues Form Asthmatics with Air Flow Limitation: In Vivo Evidence of VCAM–1/VLA–4 Interaction in Selective Eosinophil Infiltration", *American Journal of Respiratory Cell and Molecular Biology*, 1995, vol. 12, pp. 4–12.

A. Sakai, et al., "P–Selectin and Vascular Cell Adhesion Molecule–1 are Focally Expressed in Aortas of Hypercholesterolemic Rabbits Before Intimal Accumulation of Macrophages and T Lymphocytes", *Arteriosclerosis, Thrombosis, and Vascular Biology*, Feb. 1997, vol. 17, No. 2, pp. 310–316.

H. Wakita, et al., "E–Selectin and Vascular Cell Adhesion Molecule–1 as Critical Adhesion Molecules for Infiltration of T Lymphocytes and Eosinophils in Atopic Dermatitis", *Journal of Cutaneous Pathology*, 1994, pp. 33–39.

T. Satoh, et al., "Cyclophosphamide–Induced Blood and Tissue Eosinophilia in Contact Sensitivity: Mechanism of Hapten–Induced Eosinophil Recruitment into the Skin", *European Journal of Immunology*, 1997, vol. 27, pp. 85–91.

P. P. Takm et al., "Expression of Adhesion Molecules in Early Rheumatoid Synovial Tissue", *Clinical Immunology and Immunopathology*, Dec. 1995, vol. 77, No. 3, pp. 236–242.

S. Albelda, et al., "Adhesion Molecules and Inflammatory Injury", *The FASEB Journal*, Reviews, May 1994, vol. 8, pp. 504–512.

(List continued on next page.)

*Primary Examiner*—Phyllis G. Spivack
(74) *Attorney, Agent, or Firm*—Oblon, Spivak, McClelland, Maier & Neustadt, P.C.

(57) ABSTRACT

Cyclic diamine compounds of formula (1) are disclosed:

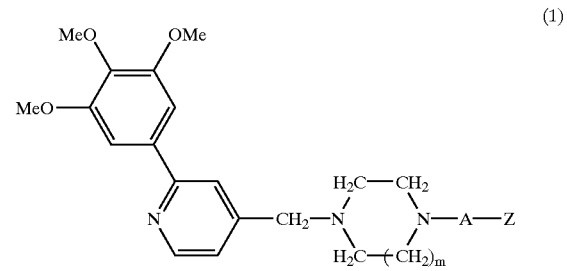

wherein

A is $(CH_2)_n$, $(CH_2)_n$—CH=CH, CO—$(CH_2)_n$ or CO—$(CH_2)_n$—CH=CH, in which n is a number of 0 to 3; Z represents a formula (2) or (3):

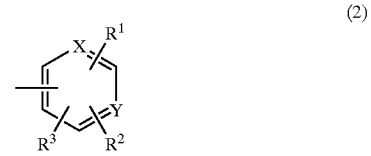

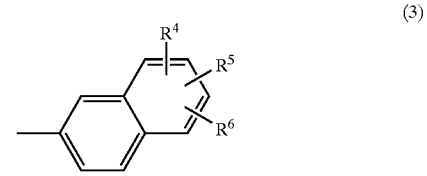

in which $R^1$, $R^2$, $R^4$, $R^5$ and $R^6$ are individually a hydrogen atom, alkyl group, alkoxy group, halogen atom or nitro group; $R^3$ is a hydrogen atom, alkyl group, alkoxy group, halogen atom, nitro group, naphthyl group, or phenyl group which may be substituted by 1 to 3 substituents selected from the group consisting of alkyl groups, alkoxy groups, halogen atoms, a nitro group and a phenyl group; and X and Y are individually CH or a nitrogen atom; and m is 1 or 2; an acid-addition salt thereof, or a hydrate thereof, and a medicine containing such a compound.

41 Claims, No Drawings

OTHER PUBLICATIONS

T. A. Springer, "Traffic Signals On Endothelium for Lymphocyte Recirculation and Leukocyte Emigration", *Annu. Rev. Physiol.*, 1995, vol. 57, pp. 827–872.

S. A. Michie, et al., "The Roles of α4–Integrins in the Development of Insulin–=Dependent Diabetes Mellitus", *Curr. Top. Microbiol. Immunol.*, 1998, vol. 231, pp. 65–83.

N. Ebihara, et al., "Anti VLA–4 Monoclonal Antibody Inhibits Eosinophil Infiltration in Allergic Conjunctivitis Model of Guinea Pig", *Current Eye Research*, 1999, vol. 19, No. 1, pp. 20–25.

S. M. Whitcup, et al., "Blocking ICAM–1 (CD54) and LFA–1 (CD11a) Inhibits Experimental Allergic Conjunctivitis", *Clinical Immunology*, Nov. 1999, vol. 93, No. 2, pp. 107–113.

A. Soriano, et al., "VCAM–1, but not ICAM–1 or MAd-CAM–1, Immunoblockade Ameliorates DSS–Induced Colitis in Mice", *Laboratory Investigation*, Oct. 2000, vol. 80, No. 10, pp. 1541–1551.

A. Zeidler, et al., "Therapeutic Effects of Antibodies Against Adhesion Molecules in Murine Collagen Type II–Induced Arthritis", *Autoimmunity*, 1995, vol. 21, pp. 245–252.

F. Bendjelloul, et al., "Intercellular Adhesion Molecule–1 (ICAM–1) Deficiency Protects Mice Against Severe Forms of Experimentally Induced Colitis", *Clinical and Experimental Immunology*, 2000, vol. 119, pp. 57–63.

W. W. Wolyniec, et al., "Reduction of Antigen–Induced Airway Hyperreactivity and Eosinophilia in ICAM–1–Deficient Mice", *American Journal of Respiratory Cell and Molecular Biology*, 1998, vol. 18, pp. 777–785.

D. C. Bullard, et al., "Reduced Susceptibility to Collagen-Induced Arthritis in Mice Deficient in Intercellular Adhesion Molecule–$1^1$", *The Journal of Immunology*, 1996, vol. 157, pp. 3153–3158.

D. H. Boschelli, et al., "Inhibition of E–Selectin–, ICAM–1–, and VCAM–1–Mediated Cell Adhesion by Benzo[b]thiophene–, Benzofuran–, Indole–, and Naphthalene–2–Carboxamides: Identification of PD 144795 as an Antiinflammatory Agent", *Journal of Medicinal Chemistry*, 1995, vol. 38, No. 22, pp. 4597–4614.

UNSYMMETRICAL CYCLIC DIAMINE COMPOUND

BACKGROUND OF THE INVENTION

1. Field of the Invention

The present invention relates to novel cyclic diamine compounds which have inhibitory effects on both cell adhesion and cell infiltration and are useful as anti-asthmatic agents, anti-allergic agents, anti-rheumatic agents, anti-arteriosclerotic agents, anti-inflammatory agents or the like, and medicines containing such compounds.

2. Description of the Background Art

In various inflammatory diseases, infiltration of leukocytes into inflammatory sites is observed. For example, infiltration of eosinophils into the bronchus in asthma (Ohkawara, Y. et al., Am. J. Respir. Cell Mol. Biol., 12, 4–12 (1995)), infiltration of macrophages and T lymphocytes into the aorta in arteriosclerosis (Sakai, A. et al., Arterioscler Thromb. Vasc. Biol., 17, 310–316 (1997)), infiltration of T lymphocytes and eosinophils into the skin in atopic dermatitis (Wakita H. et al, J. Cutan. Pathol., 21, 33–39 (1994)) or contact dermatitis (Satoh, T. et al., Eur. J. Immunol., 27, 85–91 (1997)), and infiltration of various leukocytes into rheumatoid synovial tissue (Tak, P P. et al., Clin. Immunol. Immunopathol., 77, 236–242 (1995)), have been reported.

Infiltration of these leukocyteds is elicited by cytokines, chemokines, lipids, and complements produced in inflammatory sites (Albelda, S M. et al., FASEB J., 8, 504–512 (1994)). Activated leukocytes adhere to vascular endothelial cells through an interaction called rolling or tethering with endothelial cells activated likewise. Thereafter, the leukocytes transmigrate through endothelium to infiltrate into the inflammatory sites (Springer, T A., Annu. Rev. Physiol., 57, 827–872 (1995)). In adhesion of leukocytes to the vascular endothelial cells in this process, various cell adhesion molecules such as an immunoglobulin superfamily (ICAM-1, VCAM-1 and the like), a selectin family (E-selectin and the like), an integrin family (LFA-1, VLA-4 and the like) and CD44, which are induced on the surfaces of the cells by stimulation by cytokines or the like, play important roles ("Rinsho Meneki (Clinical Immune)", 30, Supple. 18 (1998)), and relationship between the disorder state and aberrant expression of the cell adhesion molecules is noted.

Accordingly, an agent capable of inhibiting cell adhesion can be useful as an agent for preventing and treating allergic diseases such as bronchial asthma, dermatitis, rhinitis and conjunctivitis; autoimmune diseases such as rheumatoid arthritis, nephritis, inflammatory bowel diseases, diabetes and arteriosclerosis; and chronic inflammatory diseases. In fact, it has been reported that antibodies against adhesion molecules on leukocytes such as LFA-1, Mac-1 and VLA-4 or antibodies against ICAM-1, VCAM-1, P-selectin, E-selectin and the like on vascular endothelial cells, which become ligands thereof, inhibit infiltration of leukocytes into inflammatory sites in animal models. For example, neutralizing antibodies against VCAM-1 and VLA-4, which is a counter receptor thereof, can delay development of diabetes in an NOD mouse model which spontaneously causes the diabetes (Michie, S A. et al., Curr. Top. Microbiol. Immunol., 231, 65–83 (1998)). It has also been reported that an antibody against VLA-4 or ICAM-1 and its counter receptor, LFA-1, inhibits infiltration of eosinophils in a guinea pig and mouse allergic conjunctivitis model (Ebihara et al., Current Eye Res., 19, 20–25 (1999); Whitcup, S M et al., Clin. Immunol., 93, 107–113 (1999)), and a monoclonal antibody against VCAM-1 inhibits infiltration of leukocytes in a mouse DSS-induced colitis model to attenuate colitis (Soriano, A. et al., Lab. Invest., 80, 1541–1551 (2000)). Further, an anti-VLA-4 antibody and an anti-CD44 antibody reduce the incidence of disease symptoms in a mouse collagen arthritis model (Zeidler, A. et al., Autoimmunity, 21, 245–252 (1995)). Even in cell adhesion molecule deficient-mice, inhibition of infiltration of leukocytes into inflammatory tissues is observed, likewise in inflammatory models (Bendjelloul, F. et al., Clin. Exp. Immunol., 119, 57–63 (2000); Wolyniec, W W. et al., Am. J. Respir. Cell Mol. Biol., 18, 777–785 (1998); Bullard, DC. et al., J. Immunol., 157, 3153–3158 (1996)).

However, it is difficult to develop antibody-based drugs because they are polypeptides and so oral administration is a problem. Moreover, possible side effects due to antigenicity and allergic reactions are problems.

On the other hand, there have been various investigations of low-molecular weight compounds having an inhibitory effect on cell adhesion with a view toward permitting oral administration. These compounds include benzothiophene derivatives (Boschelli, D H. et al., J. Med. Chem., 38, 4597–4614 (1995)), naphthalene derivatives (Japanese Patent Application Laid-Open No. 10-147568), hydroxybenzoic acid derivatives (Japanese Patent Application Laid-Open No. 10-182550), lignans (Japanese Patent Application Laid-Open No. 10-67656), 2-substituted benzothiazole derivatives (Japanese Patent Application Laid-Open No. 2000-086641 through PCT route), condensed pyrazine compounds (Japanese Patent Application Laid-Open No. 2000-319277 through PCT route), 2,6-dialkyl-4-silylphenol (Japanese Patent Application Laid-Open Re-Publication No. 2000-509070 through PCT route) and the like. However, the goal has not often been sufficiently achieved under the circumstances. Cyclic diamine compounds described in Japanese Patent Application Laid-Open Nos. 9-143075 and 11-92382 do not exhibit a sufficient inhibitory effect on cell adhesion, and so there is a demand for further improvement in activity.

SUMMARY OF THE INVENTION

An object of the present invention is to provide a substance having inhibitory effects on both cell adhesion and cell infiltration, plus excellent anti-asthmatic effects, anti-allergic effects, anti-rheumatic effects, anti-arteriosclerotic effects and anti-inflammatory effects.

With the foregoing circumstances in mind, the present inventors carried out an extensive investigation to find a substance which inhibits cell adhesion and cell infiltration. As a result, we found that compounds represented by the general formula (1), have excellent cell adhesion-inhibiting effects and cell infiltration-inhibiting effects and are useful as anti-allergic agents, anti-asthmatic agents, anti-rheumatic agents, anti-arteriosclerotic agents or anti-inflammatory agents.

The present invention provides a cyclic diamine compound represented by the following general formula (1):

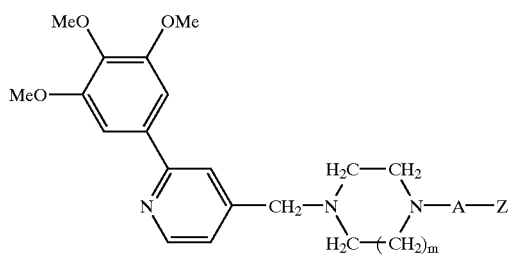

(1)

wherein

A is $(CH_2)_n$, $(CH_2)_n$—CH=CH, CO—$(CH_2)_n$ or CO—$(CH_2)_n$—CH=CH, in which n is a number of 0 to 3; Z represents a formula (2) or (3):

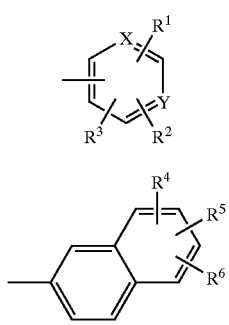

in which $R^1$, $R^2$, $R^4$, $R^5$ and $R^6$ are the same or different from one another and individually a hydrogen atom, alkyl group, alkoxy group, halogen atom or nitro group; $R^3$ is a hydrogen atom, alkyl group, alkoxy group, halogen atom, nitro group, naphthyl group, or phenyl group which may be substituted by 1 to 3 substituents selected from alkyl groups, alkoxy groups, halogen atoms, a nitro group and a phenyl group; and X and Y are the same or different from each other and individually CH or a nitrogen atom; and m is a number of 1 or 2;

an acid-addition salt thereof, or a hydrate thereof.

According to the present invention, there is also provided a medicine comprising the above cyclic diamine compound, an acid-addition salt thereof, or a hydrate thereof as an active ingredient.

According to the present invention, there is further provided a medicinal composition comprising the above cyclic diamine compound, the acid-addition salt thereof, or the hydrate thereof and a pharmaceutically acceptable carrier.

According to the present invention, there is still further provided a method for treating a disease caused by cell adhesion and/or cell infiltration, which comprises administering an effective amount of the above cyclic diamine compound, an acid-addition salt thereof, or a hydrate thereof to a patient who requires such treatment.

DETAILED DESCRIPTION OF THE PREFERRED EMBODIMENTS

The alkyl groups represented by $R^1$ to $R^6$ are preferably $C_1$–$C_6$-alkyl groups, and preferable specific examples include methyl, ethyl, n-propyl, isopropyl, n-butyl, isobutyl, tert-butyl, pentyl and hexyl groups, with methyl, ethyl, n-propyl, isopropyl and tert-butyl groups being particularly preferred.

The alkoxy groups represented by $R^1$ to $R^6$ are preferably $C_1$–$C_6$-alkoxy groups, and preferable specific examples include methoxy, ethoxy, isopropoxy, n-butoxy and isobutoxy groups, with methoxy, ethoxy and isopropoxy groups being particularly preferred. The halogen atoms represented by $R^1$ to $R^6$ include chlorine, bromine, fluorine and iodine atoms.

$R^3$ may be a phenyl group which may be substituted by 1 to 3 substituents selected from alkyl groups, alkoxy groups, halogen atoms, a nitro group and a phenyl group, and as examples of the substituents on said phenyl group, may be mentioned the same groups and atoms as the alkyl groups, alkoxy groups and halogen atoms mentioned above.

$(CH_2)_n$ is preferably methylene, ethylene or trimethylene. $(CH_2)_n$—CH=CH is preferably $CH_2CH$=CH, $(CH_2)_2$—CH=CH or $(CH_2)_3$—CH=CH. CO—$(CH_2)_n$ is preferably CO or CO—$CH_2$. CO—$(CH_2)_n$—CH=CH is preferably CO—CH=CH.

Examples of the ring having X and Y in the formula (2) include benzene, pyridine and pyrimidine rings.

No particular limitation is imposed on the acid-addition salts of the compounds (1) according to the present invention so far as they are pharmaceutically acceptable salts. However, examples of the acid-addition salts include acid-addition salts of mineral acids, such as hydrochlorides, hydrobromides, hydriodides, sulfates and phosphates; and acid-addition salts of organic acids, such as benzoates, methanesulfonates, ethanesulfonates, benzenesulfonates, p-toluenesulfonates, oxalates, maleates, fumarates, tartrates, citrates and acetates.

The compounds (1) according to the present invention may be present in the form of solvates typified by hydrates, and the solvates may also be embraced in the present invention.

The compound (1) according to the present invention can be prepared in accordance with, for example, the following process a, b or c:

Process a

A synthetic process in the case where A is $(CH_2)_n$ or $(CH_2)_n$—CH=CH, in which a substituted pyridylmethyl group is introduced into a diamine (9) before introduction of A-Z.

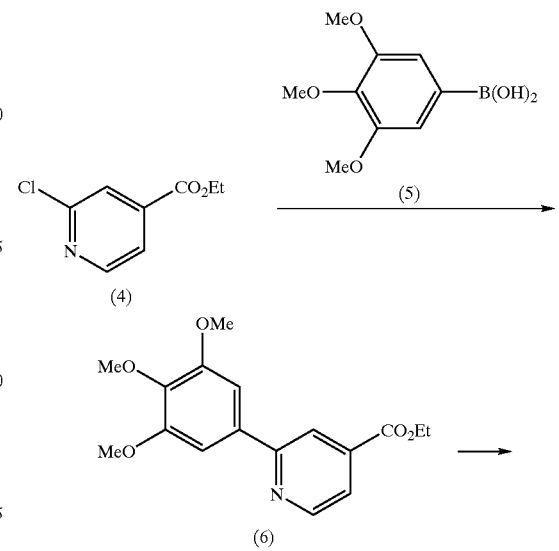

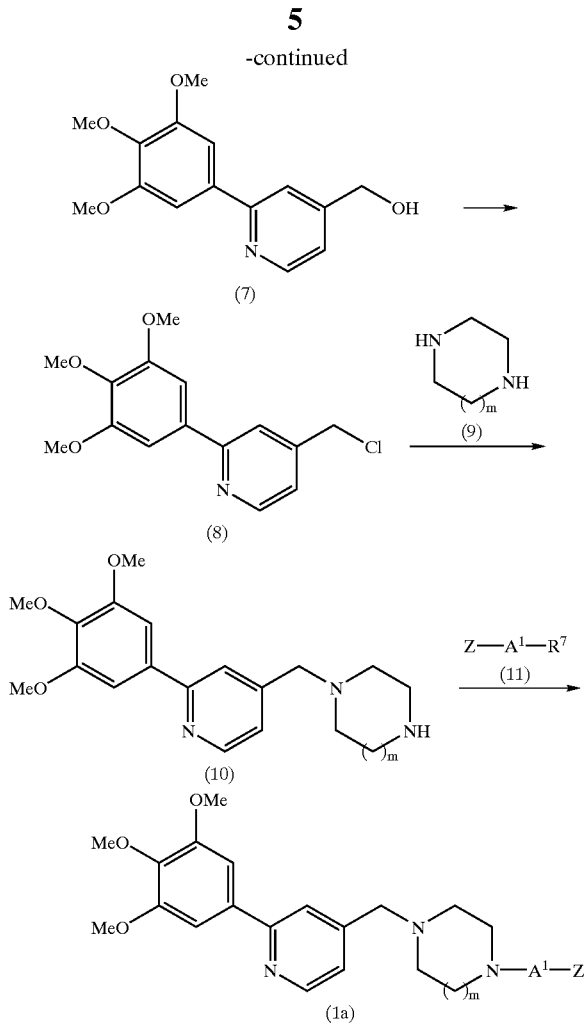

wherein $R^7$ is a halogen atom, or an alkylsulfonyloxy or arylslfonyloxy group, $A^1$ is $(CH_2)_n$ or $(CH_2)_n$—CH=CH, and m and Z have the same meanings as defined above.

More specifically, ethyl 2-chloroisonicotinate (4) is reacted with 3,4,5-trimethoxyphenylboronic acid (5) at 0° C. to reflux temperature, preferably 90° C. for 10 minutes to several days, preferably 5 hours in the presence of a metal catalyst such as tetrakis(triphenylphosphine)-palladium(0) in a mixture of a solvent such as toluene, benzene, tetrahydrofuran (THF), dioxane or acetonitrile and 2 M sodium carbonate, thereby obtaining a compound (6). This compound is reacted with lithium aluminum hydride at −20° C. to room temperature, preferably 0° C. for several seconds to several hours, preferably 30 minutes in THF, thereby giving an alcohol (7). The alcohol (7) is stirred together with thionyl chloride at −20° C. to room temperature, preferably 0° C. for 1 hour to several days, preferably 5 hours in a solvent such as chloroform, dichloromethane, ethyl acetate, ether, THF or dioxane, thereby obtaining a chloro-derivative (8). The chloro-derivative (8) and a diamine (9) are stirred at room temperature to 100° C., preferably 50° C. for 1 hour to several days, preferably 5 hours in the presence of potassium carbonate in a solvent such as N,N-dimethylformamide (DMF), dimethyl sulfoxide (DMSO) or acetonitrile, thereby obtaining a mono-substituted compound (10). The compound (10) is condensed with a compound (11), thereby obtaining a compound (1a) according to the present invention. The condensation reaction is conducted by stirring the reactants at room temperature to 100° C., preferably 50° C. for 1 hour to several days, preferably 5 hours in the presence of potassium carbonate in a solvent such as DMF, DMSO or acetonitrile.

As the halogen atom represented by $R^7$, chlorine or bromine are preferred. As the alkylsulfonyloxy group, a methanesulfonyloxy group is preferred. As the arylsulfonyloxy group, a p-toluenesulfonyloxy group is preferred.

The compound (11) can be prepared in accordance with, for example, the following reaction formula:

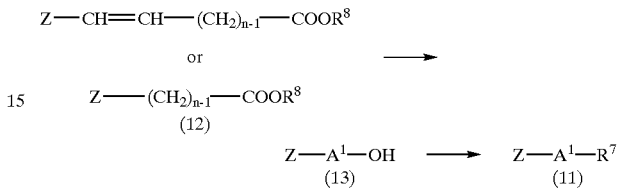

wherein $R^8$ is a hydrogen atom or lower alkyl group, $A^1$ is $(CH_2)_n$ or $(CH_2)_n$—CH=CH, and Z and $R^7$ have the same meanings as defined above.

More specifically, a carboxylic acid or its ester derivative (12) is reduced with a reducing agent such as lithium aluminum hydride to give an alcohol (13). The alcohol is then reacted with a halogenating agent such as thionyl chloride, or a methanesulfonylating agent, thereby obtaining the compound (11). The reduction reaction is conducted in the same manner as described above. The reaction of the alcohol (13) with thionyl chloride in the case of the halogenation, or with methanesulfonyl chloride in the case of the methanesulfonylation is preferably conducted by stirring the reactants at −20° C. to room temperature, preferably 0° C. for 1 hour to several days, preferably 5 hours in a solvent such as chloroform, dichloromethane, ethyl acetate, ether, THF or dioxane for thionyl chloride or in the presence of a base such as triethylamine or pyridine in a solvent such as chloroform, dichloromethane, ethyl acetate, ether, THF, dioxane or pyridine for methanesulfonyl chloride.

Process b

A synthetic process in the case where A is $(CH_2)_n$ or $(CH_2)_n$—CH=CH, in which a substituted pyridylmethyl group is introduced into a diamine (9) after introduction of A–Z.

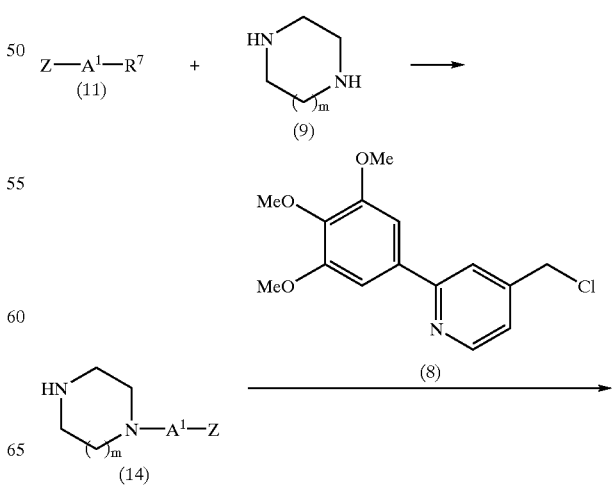

-continued

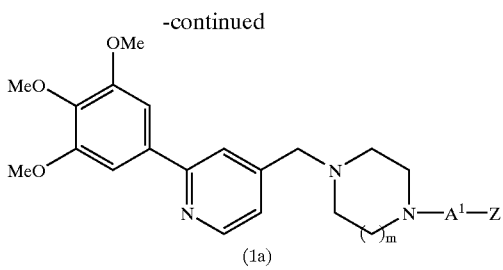
(1a)

wherein $A^1$ is $(CH_2)_n$ or $(CH_2)_n$—CH=CH, and Z, $R^7$ and m have the same meanings as defined above.

More specifically, a compound (11) is condensed with a diamine (9) to give a mono-substituted compound (14). This compound (14) is reacted with a compound (8), thereby obtaining a compound (1a) according to the present invention. In this reaction, the condensation reaction of the compound (11) with the diamine (9) and the condensation reaction of the compound (14) with the compound (8) can be conducted under the same conditions as in the reactions of the compound (8) and the compound (9).

Process c

A synthetic process in the case where A is CO—$(CH_2)_n$ or CO—$(CH_2)_n$—CH=CH.

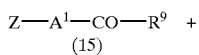
(15)

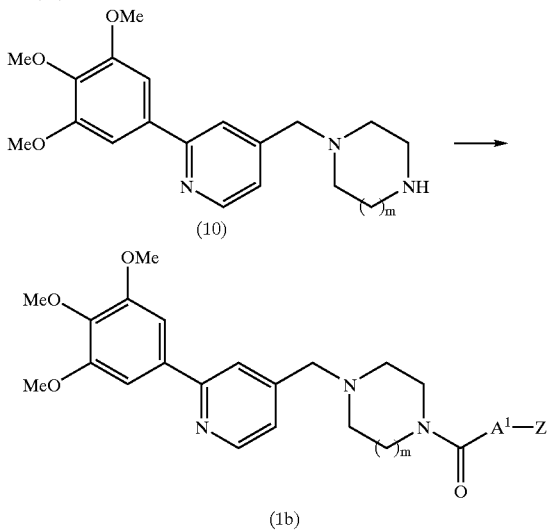
(10)

(1b)

wherein $R^9$ is a halogen atom or hydroxyl group, $A^1$ is CO—$(CH_2)_n$ or CO—$(CH_2)_n$—CH=CH, and Z and m have the same meanings as defined above.

More specifically, a compound (15), which is an acid chloride or carboxylic acid, is condensed with a compound (10), thereby obtaining a compound (1b) according to the present invention. The reaction of the acid chloride (15) with the compound (10) is conducted by, for example, stirring the reactants at 0° C. to reflux temperature, preferably room temperature for 1 hour to several days, for preferably 5 hours in a solvent such as chloroform or dichloromethane. The reaction of the carboxylic acid (15) with the compound (10) is conducted by, for example, causing the reactants to react at 0° C. to reflux temperature, preferably room temperature for 10 minutes to several days, preferably 6 hours in the presence of a dehydration-condensing agent such as dicyclohexyl-carbodiimide, 1-ethyl-3-(3-dimethylaminopropyl)-carbodiimide hydrochloride (water-soluble carbodiimide hydrochloride) or diisopropylcarbodiimide in a solvent such as chloroform or dichloromethane.

The compounds (1) according to the present invention are obtained by any of the above-described processes and may further be purified by using an ordinary purification means such as recrystallization or column chromatography as needed. Also as needed, the compounds may be converted into the desired salts or solvates by methods known in the art.

The compounds (1) according to the present invention, or acid-addition salts or solvates thereof thus obtained have excellent inhibitory effects on cell adhesion as demonstrated in the Examples, which will be described subsequently, and are useful as medicines for treatment or prevention of diseases of animals including humans, such as asthma, allergy, rheumatism, arteriosclerosis and inflammation.

The medicine according to the present invention comprises a compound (1), a salt thereof, or a solvate thereof as an active ingredient. The form of administration may be suitably selected as necessary for the therapeutic application intended without any particular limitation, including oral preparations, injections, suppositories, ointments, inhalants, eye drops, nose drops and plasters. A composition suitable for use in these administration forms can be prepared by blending a pharmaceutically acceptable carrier in accordance with the conventional preparation method publicly known by those skilled in the art.

When an oral solid preparation is formulated, an excipient, and optionally, a binder, a disintegrator, a lubricant, a colorant, a taste corrigent, a smell corrigent and the like are added to compound (1), and the resulting composition can be formulated into tablets, coated tablets, granules, powders, capsules, etc. in accordance with methods known in the art. As such additives described above, any additives may be used which are generally used in the pharmaceutical field. Examples include excipients such as lactose, sucrose, sodium chloride, glucose, starch, calcium carbonate, kaolin, microcrystalline cellulose and silicic acid; binders such as water, ethanol, propanol, simple syrup, glucose solution, starch solution, gelatin solution, carboxymethyl cellulose, hydroxypropyl cellulose, hydroxypropyl starch, methyl cellulose, ethyl cellulose, shellac, calcium phosphate and polyvinyl pyrrolidone; disintegrators such as dry starch, sodium alginate, agar powder, sodium hydrogencarbonate, calcium carbonate, sodium lauryl sulfate, monoglyceryl stearate and lactose; lubricants such as purified talc, stearic acid salts, borax and polyethylene glycol; and taste corrigents such as sucrose, orange peel, citric acid and tartaric acid.

When an oral liquid preparation is formulated, a taste corrigent, buffer, stabilizer, smell corrigent and/or the like are added to compound (1), and the resulting composition can be formulated into internal liquid preparations, syrup preparations, elixirs, etc. in accordance with methods known in the art. In this case, vanillin as the taste corrigent, may be used those mentioned above. As the buffer, sodium citrate may be mentioned. As examples of the stabilizer, tragacanth, gum arabic and gelatin may be mentioned.

When an injection is formulated, a pH adjustor, buffer, stabilizer, isotonicity agent, local anesthetic and the like may be added to compound (1) according to the present invention, and the resultant composition can be formulated into subcutaneous, intramuscular and intravenous injections in accordance with methods known in the art. Examples of the pH adjustor and buffer in this case include sodium citrate, sodium acetate and sodium phosphate. Examples of the stabilizer include sodium pyrosulfite, EDTA, thioglycolic acid and thiolactic acid. Examples of the local anesthetic include procaine hydrochloride and lidocaine hydrochloride. Examples of the isotonicity agent include sodium chloride and glucose.

When a suppository is formulated, a carrier preparation known in the art, for example, polyethylene glycol, lanoline, cacao butter, fatty acid triglyceride or the like, and optionally, a surfactant such as Tween (trade mark) and the like are added to the compound (1), and the resultant composition can be formulated into suppositories in accordance with methods known in the art.

When an ointment is formulated, a base material, stabilizer, wetting agent, preservative and the like, which are generally used, are blended with compound (1) as needed, and the resulting blend is mixed and formulated into ointments in accordance with known methods known in the art. Examples of the base material include liquid paraffin, white vaseline, bleached beeswax, octyldodecyl alcohol and paraffin. Examples of the preservative include methyl p-hydroxybenzoate, ethyl p-hydroxybenzoate and propyl p-hydroxybenzoate.

Besides the above preparations, inhalants, eye drops and nose drops may also be formulated in accordance with known methods.

The dose of the medicine according to the present invention varies according to the age, weight and condition of the patient to be treated, the administration method, the number of times of administration, and the like. It is however preferred that the medicine is generally orally or parenterally administered at once or in several portions in a dose of 1 to 1,000 mg per day in terms of compound (1), for an adult.

The present invention will hereinafter be described in more detail by the following Examples. However, the present invention is not limited to these examples.

Preparation Example 1

Synthesis of ethyl 2-(3,4,5-trimethoxyphenyl)-isonicotinate 3,4,5-Trimethoxyphenylboronic acid (20.64 g) and ethyl 2-chloroisonicotinate (19.06 g) were suspended in a mixed solvent of toluene (200 mL) and THF (100 mL), and to the suspension 2 M sodium carbonate (200 mL) and tetrakis(triphenylphosphine)palladium(0) (5.93 g) were added. The mixture was stirred overnight at 90° C. under an argon atmosphere. Ethyl acetate was added to the reaction mixture to separate an organic layer. The organic layer was washed with saturated brine, dried over anhydrous magnesium sulfate and concentrated under reduced pressure. The residue was purified by column chromatography on silica gel (hexane:ethyl acetate=5:1) to obtain the title compound.

Yield: 27.70 g (85%).

$^1$H-NMR (400 MHz, CDCl$_3$) δ: 1.45(t,3H,J=7.0 Hz), 3.92(s,3H), 3.99(s,6H), 4.46(q,2H,J=7.0 Hz), 7.30(s,2H), 7.76(dd,1H,J=5.1 Hz,1.6 Hz), 8.24(dd,1H,J=1.6 Hz,0.8 Hz), 8.81(dd,1H,J=5.1 Hz,0.8 Hz).

Preparation Example 2

Synthesis of 4-hydroxymethyl-2-(3,4,5-trimethoxyphenyl)-pyridine

Ethyl 2-(3,4,5-trimethoxyphenyl)isonicotinate (27.70 g) was dissolved in THF (200 mL), and to the solution lithium aluminum hydride (3.31 g) was added at 0° C. under an argon atmosphere, and the mixture was stirred at 0° C. for 1 hour. A small amount of water and then sodium sulfate were added to the reaction mixture, and the reaction mixture was filtered through celite. The filtrate was concentrated under reduced pressure, and the resultant crude crystals were recrystallized from ethyl acetate-hexane to obtain the title compound.

Yield: 18.15 g (76%).

$^1$H-NMR (400 MHz, CDCl$_3$) δ: 3.90(s,3H), 3.95(s,6H), 4.79(s,2H), 7.19(d,1H,J=5.1 Hz), 7.21(s,2H), 7.66(s,1H), 8.60(d,1H,J=5.1 Hz).

Preparation Example 3

Synthesis of 4-chloromethyl-2-(3,4,5-trimethoxyphenyl)-pyridine

4-Hydroxymethyl-2-(3,4,5-trimethoxyphenyl)pyridine (18.15 g) was dissolved in chloroform (300 mL), and to the solution thionyl chloride (19.2 mL) was added at 0° C. After 30 minutes, the mixture was warmed to room temperature and stirred for 4 hours. The reaction mixture was washed with a saturated aqueous solution of sodium hydrogencarbonate and saturated brine, dried over anhydrous sodium sulfate and concentrated under reduced pressure. The residue was then recrystallized from chloroform-hexane to obtain the title compound.

Yield: 17.87 g (92%).

$^1$H-NMR (400 MHz, CDCl$_3$) δ: 3.91(s,3H), 3.97(s,6H), 4.61(s,2H), 7.24(s,2H), 7.26(d,1H,J=5.1 Hz), 7.68(s,1H), 8.67(d,1H,J=5.1 Hz).

Preparation Example 4

Synthesis of 1-[[2-(3,4,5-trimethoxyphenyl)pyridin-4-yl]-methyl]piperazine

4-Chloromethyl-2-(3,4,5-trimethoxyphenyl)pyridine (13.52 g) and piperazine (11.89 g) were dissolved in DMF (100 mL), and to the solution potassium carbonate (15.89 g) was added. The mixture was stirred at room temperature for 5 hours. After the reaction mixture was concentrated under reduced pressure, chloroform was added to the residue, and the mixture was washed with water, dried over anhydrous magnesium sulfate and then concentrated under reduced pressure. The residue was purified by column chromatography on silica gel (chloroform:methanol=20:1 to chloroform:ammonia-saturated methanol=10:1) to obtain a free base of the title compound.

Yield: 10.34 g (66%).

$^1$H-NMR (400 MHz, CDCl$_3$) δ: 1.56(br,1H), 2.46(br,4H), 2.91(t,4H,J=4.9 Hz), 3.55(s,2H), 3.90(s,3H), 3.97(s,6H), 7.22(d,1H,J=5.1 Hz), 7.24(s,2H), 7.64(s,1H), 8.59(d,1H,J=5.1 Hz).

Preparation Example 5

Synthesis of 3-(3,4,5-trimethoxyphenyl)-2-propen-1-ol 3,4,5-Trimethoxycinnamic acid (1.5 g) was dissolved in THF (100 mL), triethylamine (0.64 mL) was added to the solution under ice cooling, and ethyl chlorocarbonate (0.44 mL) was then added dropwise thereto. After stirring the resultant mixture at room temperature for 1 hour, sodium borohydride (477 mg) was added to the mixture under ice cooling. After stirring the resultant mixture at room temperature for 1 hour, diluted hydrochloric acid was added to the reaction mixture to conduct extraction with chloroform. The resultant organic layer was washed with saturated brine, dried over anhydrous sodium sulfate and then concentrated under reduced pressure. The residue was purified by column chromatography on silica gel (hexane:ethyl acetate=1:1) to obtain the title compound.

Yield: 736 mg (78%).

$^1$H-NMR (400 MHz, CDCl$_3$) δ: 3.85(s,3H), 3.87(s,6H), 4.33(s,2H), 6.29(dt,1H,J=15.8 Hz,5.9 Hz), 6.55(d,1H,J=15.9 Hz), 6.62(s,2H).

Preparation Example 6

Synthesis of 3-(3,4,5-trimethoxyphenyl)propanol 3-(3,4,5-Trimethoxyphenyl)-2-propen-1-ol (120 mg) was dissolved in ethanol, and to the solution 10% palladium on carbon (60 mg) was added, and the mixture was stirred at room temperature for 3 hours under a hydrogen atmosphere. The reaction mixture was filtered through celite, the filtrate was then concentrated under reduced pressure and extracted with chloroform. The resultant organic layer was washed with saturated brine, dried over anhydrous sodium sulfate and concentrated under reduced pressure. The residue was purified by column chromatography on silica gel (chloroform:methanol=14:1) to obtain the title compound.

Yield: 44 mg (34%).

$^1$H-NMR (400 MHz, CDCl$_3$) δ: 1.82–1.90(m,2H), 2.63 (t,2H,J=7.8 Hz), 3.66(t,2H,J=6.4 Hz), 3.79(s,3H), 3.82(s, 6H), 6.39(s,2H).

Preparation Example 7

Synthesis of 3-(3,4,5-trimethoxyphenyl)propylmethane-sulfonate 3-(3,4,5-Trimethoxyphenyl)propanol (44 mg) was dissolved in dichloromethane (2 mL), and to the solution pyridine (55.6 mg) was added, and methanesulfonyl chloride (37.4 mg) was added thereto under ice cooling. The mixture was stirred at room temperature for 3 hours. Diluted hydrochloric acid was added to the reaction mixture to conduct extraction with chloroform. The resultant organic layer was washed with saturated brine, dried over anhydrous sodium sulfate and then concentrated under reduced pressure. The residue was then purified by column chromatography on silica gel (chloroform:methanol=40:1) to obtain the title compound.

Yield: 50 mg (85%).

$^1$H-NMR (400 MHz, CDCl$_3$) δ: 2.01–2.08(m,2H), 2.67 (t,2H,J=7.5 Hz), 2.99(s,3H), 3.80(s,3H), 3.82(s,6H), 4.21(t, 2H,J=6.2 Hz), 6.38(s,2H).

EXAMPLE 1

Synthesis of N-[3-(3,4,5-trimethoxyphenyl)propyl]-N'-[[2-(3,4,5-trimethoxyphenyl)pyridin-4-yl]methyl] piperazine dimaleate

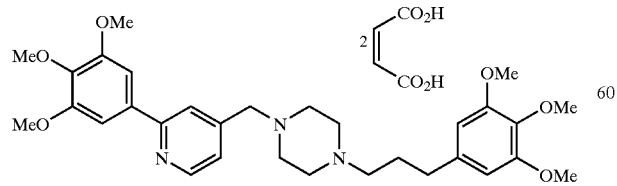

1-[[2-(3,4,5-Trimethoxyphenyl)pyridin-4-yl]-methyl] piperazine (57 mg) was dissolved in acetonitrile (4 mL), and to the solution 3-(3,4,5-trimethoxyphenyl)propyl methane-sulfonate (50 mg), potassium iodide (35 mg) and potassium carbonate (46 mg) were added, and the mixture was stirred at 70° C. for 2 hours. Water was added to the reaction mixture to conduct extraction with chloroform. The resultant organic layer was washed with saturated brine, dried over anhydrous sodium sulfate and then concentrated under reduced pressure. The residue was purified by column chromatography on silica gel (chloroform:methanol=20:1). Maleic acid was added to the resultant oil to produce a salt, thereby obtaining the title compound.

Yield: 52 mg (40%).

$^1$H-NMR (measured as a free base, 400 MHz, CDCl$_3$) δ: 1.79–1.93(m,2H), 2.37–2.68(m,12H), 3.58(s,2H), 3.82(s, 3H), 3.84(s,6H), 3.90(s,3H), 3.97(s,6H), 6.40(s,2H), 7.21–7.24(m,3H), 7.63(s,1H), 8.59(d,1H,J=5.1 Hz).

m/z (EI): 551 [M$^+$].

Preparation Example 8

Synthesis of ethyl 3-(2,3,4-trimethoxyphenyl) propenoate

Sodium hydride (60% dispersion in mineral oil; 245 mg) was suspended in THF (1 mL) under an argon atmosphere, to the suspension ethyl diethylphosphonoacetate (1.11 mL) was added dropwise under ice cooling, and the mixture was stirred for 30 minutes. After 2,3,4-trimethoxybenzaldehyde (1.0 g) was then added to the mixture, the reaction mixture was stirred at room temperature for 30 minutes and concentrated under reduced pressure. The residue was dissolved in chloroform, and the solution was washed with water and saturated brine, dried over anhydrous magnesium sulfate and then concentrated under reduced pressure. The residue was purified by column chromatography on silica gel (hexane:ethyl acetate=1:1) to obtain the title compound.

Yield: 1.15 g (84%).

$^1$H-NMR (400 MHz, CDCl$_3$) δ: 1.33(t,3H,J=7.1 Hz), 3.88(s,3H), 3.89(s,3H), 3.92(s,3H), 4.25(q,2H,J=7.2 Hz), 6.42(d,1H,J=16.0 Hz), 6.69(d,1H,J=8.8 Hz), 7.27(d,1H,J= 8.8 Hz), 7.88(d,1H,J=16.0 Hz).

Preparation Example 9

Synthesis of 3-(2,3,4-trimethoxyphenyl)propenoic acid

Ethyl 3-(2,3,4-trimethoxyphenyl)propenoate (1.15 g) was dissolved in ethanol (20 mL), and to the solution 10% potassium hydroxide (1.21 g) was added, and the mixture was stirred at room temperature for 5 hours. The reaction mixture was concentrated under reduced pressure, water was added to the residue, and the mixture was adjusted to pH 2 with 2 M hydrochloric acid and extracted with ethyl acetate. The resultant organic layer was dried over anhydrous sodium sulfate and then concentrated under reduced pressure to obtain the title compound.

Yield: 1.00 g (97%).

Preparation Example 10

Synthesis of 3-(2,3,4-trimethoxyphenyl)-2-propen-1-ol 3-(2,3,4-Trimethoxyphenyl)propenoic acid (585 mg) was treated in the same manner as in Preparation Example 5 to obtain the title compound.

Yield: 410 mg (80%).

¹H-NMR (400 MHz, CDCl₃) δ: 3.86(s,3H), 3.87(s,3H), 3.90(s,3H), 4.32(d,2H,J=6.1 Hz), 6.30(dt,1H,J=16.0 Hz,6.1 Hz), 6.66(d,1H,J=8.8 Hz), 6.80(d,1H,J=16.0 Hz), 7.17(d, 1H,J=8.8 Hz).

Preparation Example 11

Synthesis of 3-(2,3,4-trimethoxyphenyl)propanol 3-(2,3,4-trimethoxyphenyl)-2-propen-1-ol (163 mg) was treated in the same manner as in Preparation Example 6 to obtain the title compound.

Yield: 75 mg (43%).

¹H-NMR (400 MHz, CDCl₃) δ: 1.81(quint,2H,J=6.7 Hz), 1.98(t,1H,J=6.0 Hz), 2.67(t,2H,J=7.2 Hz), 3.57–3.61(m, 2H), 3.85(s,3H), 3.87(s,3H), 3.90(s,3H), 6.74(d,1H,J=8.3 Hz), 6.84(d,1H,J=8.6 Hz).

Preparation Example 12

Synthesis of 3-(2,3,4-trimethoxyphenyl) propylmethane-sulfonate 3-(2,3,4-trimethoxyphenyl)propanol (37 mg) was treated in the same manner as in Preparation Example 7 to obtain the title compound.

Yield: 14 mg (28%).

¹H-NMR (400 MHz, CDCl₃) δ: 2.02(quint,2H,J=6.7 Hz), 2.68(t,2H,J=7.4 Hz), 3.01(s,3H), 3.84(s,3H), 3.87(s,3H), 3.89(s,3H), 4.23(t,2H,J=6.3 Hz), 6.61(d,1H,J=8.3 Hz), 6.82 (d,1H,J=8.6 Hz).

EXAMPLE 2

Synthesis of N-[3-(2,3,4-trimethoxyphenyl)propyl]-N'-[[2-(3,4,5-trimethoxyphenyl)pyridin-4-yl]methyl] piperazine dimaleate

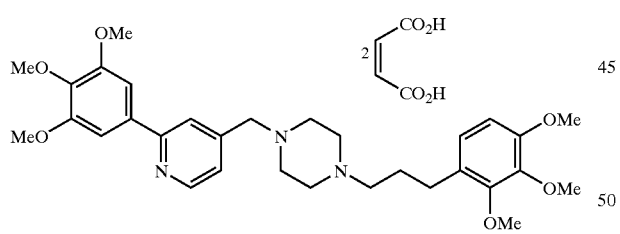

1-[[2-(3,4,5-Trimethoxyphenyl)pyridin-4-yl]methyl]-piperazine (17 mg) and 3-(2,3,4-trimethoxyphenyl) propylmethanesulfonate (14 mg) were reacted in the same manner as in Example 1 to produce a maleate, thereby obtaining the title compound.

Yield: 16 mg (45%).

¹H-NMR (measured as a free base, 400 MHz, CDCl₃) δ: 1.65–1.80(m,2H), 2.30–2.70(m,12H), 3.50(s,2H), 3.76(s, 3H), 3.78(s,3H), 3.79(s,3H), 3.83(s,3H), 3.90(s,6H), 6.52(d, 1H,J=8.6 Hz), 6.75(d,1H,J=8.4 Hz), 7.12–7.16(m,3H), 7.56 (s,1H), 8.52(d,1H,J=4.9 Hz).

m/z (EI): 551[M⁺].

EXAMPLE 3

Synthesis of N-[3-(pyridin-4-yl)propyl]-N'-[[2-(3,4, 5-trimethoxyphenyl)pyridin-4-yl)methyl]piperazine dimaleate

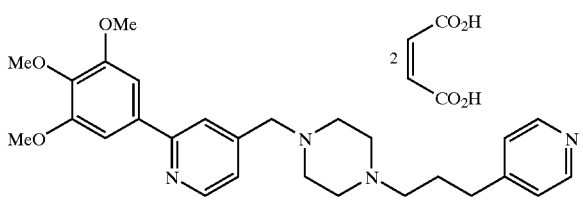

1-[[2-(3,4,5-Trimethoxyphenyl)pyridin-4-yl]methyl]-piperazine (196 mg) and 4-(3-chloropropyl)pyridine (89 mg) were reacted in the same manner as in Example 1 to produce a maleate, thereby obtaining the title compound.

Yield: 73 mg (18%).

¹H-NMR (measured as a free base, 400 MHz, CDCl₃) δ: 1.78–1.90(m,2H), 2.37(t,2H,J=6.4 Hz), 2.40–2.61(m,8H), 2.61(t,2H,J=6.6 Hz), 3.58(s,2H), 3.91(s,3H), 3.97(s,6H), 7.12(d,2H,J=5.6 Hz), 7.23–7.24(m,3H), 7.64(s,1H), 8.48(d, 1H,J=5.8 Hz), 8.60(d,2H,J=4.9 Hz).

m/z (EI): 462 [M⁺].

EXAMPLE 4

Synthesis of N-[(6-methylpyridin-2-yl)methyl]-N'-[[2-(3,4,5-trimethoxyphenyl)pyridin-4-yl]methyl] piperazine dimaleate

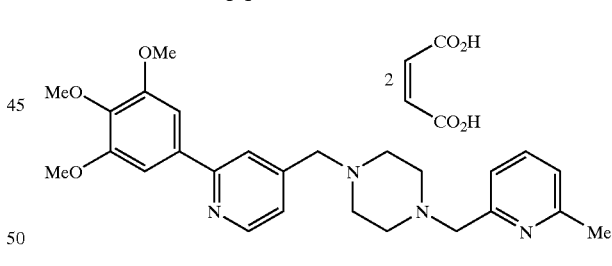

1-[(2-(3,4,5-Trimethoxyphenyl)pyridin-4-yl)methyl]-piperazine (197 mg) and 2-chloromethyl-6-methylpyridine (59 mg) were reacted in the same manner as in Example 1 to produce a maleate, thereby obtaining the title compound.

Yield: 105 mg (32%).

¹H-NMR (measured as a free base, 400 MHz, CDCl₃) δ: 2.54–2.56(m,7H) ,3.13(br,4H), 3.84(s,2H), 3.90(s,3H), 3.98 (s,6H), 5.13(s,2H), 7.22–7.25(m,4H), 7.67–7.71(m,2H), 8.06(d,1H,J=7.6 Hz), 8.60(d,1H,J=5.1 Hz).

m/z (EI) : 448[M⁺].

EXAMPLE 5

Synthesis of N-benzyl-N'-[[2-(3,4,5-trimethoxyphenyl)-pyridin-4-yl]methyl]piperazine dimaleate

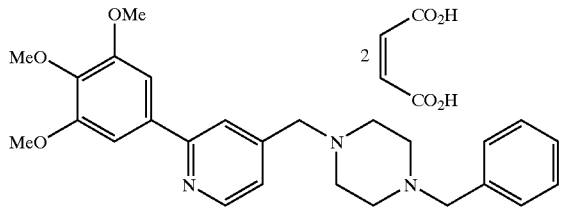

1-[[2-(3,4,5-Trimethoxyphenyl)pyridin-4-yl]methyl]-piperazine (103 mg) and benzyl bromide (46 μL) were reacted in the same manner as in Example 1 to produce a maleate, thereby obtaining the title compound.

Yield: 22 mg (11%).

$^1$H-NMR (measured as a free base, 400 MHz, CDCl$_3$) δ: 2.80–3.62(m,8H), 3.70(s,3H), 3.75(s,2H), 3.86(s,6H), 4.23 (s,2H), 7.30(d,1H,J=4.6 Hz), 7.35(s,2H), 7.45(br,5H), 7.89 (s,1H), 8.61(d,1H,J=4.9 Hz).

m/z (EI): 433 [M$^+$].

EXAMPLE 6

Synthesis of N-(4-methylbenzyl)-N'-[[2-(3,4,5-trimethoxy-phenyl)pyridin-4-yl]methyl]piperazine dimaleate

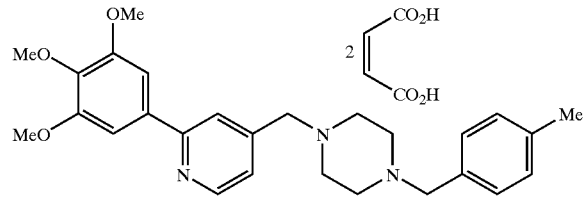

1-[[2-(3,4,5-Trimethoxyphenyl)pyridin-4-yl]methyl]-piperazine (172 mg) and 4-methylbenzyl chloride (97 mg) were reacted in the same manner as in Example 1 to produce a maleate, thereby obtaining the title compound.

Yield: 63 mg (19%).

$^1$H-NMR (measured as a free base, 400 MHz, CDCl$_3$) δ: 2.33(s,3H), 2.51(br,8H), 3.49(s,2H), 3.56(s,2H), 3.90(s,3H), 3.97(s,6H), 7.11–7.23(m,7H), 7.62(s,1H), 8.58(d,1H,J=4.9 Hz).

m/z (EI): 447 [M$^+$].

EXAMPLE 7

Synthesis of N-(3-methylbenzyl)-N'-[[2-(3,4,5-trimethoxy-phenyl)pyridin-4-yl]methyl]piperazine dimaleate

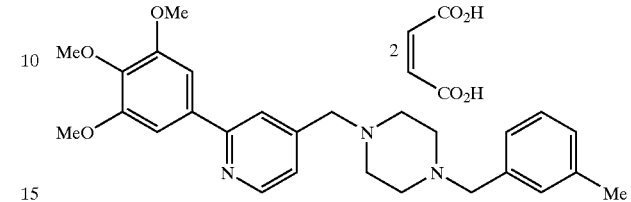

1-[[2-(3,4,5-Trimethoxyphenyl)pyridin-4-yl]methyl]-piperazine (113 mg) and 3-methylbenzyl chloride (111 mg) were reacted in the same manner as in Example 1 to produce a maleate, thereby obtaining the title compound.

Yield: 48 mg (14%).

$^1$H-NMR (measured as a free base, 400 MHz, CDCl$_3$) δ: 2.36(s,3H), 2.42–2.61(m,8H), 3.47(s,2H), 3.56(s,2H), 3.90 (s,3H), 3.97(s,6H), 7.12–7.26(m,7H), 7.64(s,1H), 8.59(d, 1H,J=4.9 Hz).

m/z (EI): 447 [M$^+$].

EXAMPLE 8

Synthesis of N-(4-tert-butylbenzyl)-N'-[[2-(3,4,5-trimethoxyphenyl)pyridin-4-yl]methyl]piperazine dimaleate

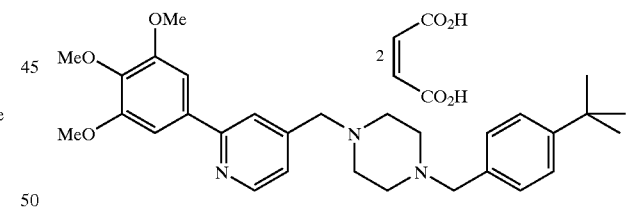

1-[[2-(3,4,5-Trimethoxyphenyl)pyridin-4-yl]methyl]-piperazine (172 mg) and 4-tert-butylbenzyl chloride (136 mg) were reacted in the same manner as in Example 1 to produce a maleate, thereby obtaining the title compound.

Yield: 43 mg (12%).

$^1$H-NMR (measured as a free base, 400 MHz, CDCl$_3$) δ: 1.31 (s, 9H), 2.50(br,8H), 3.50(s,2H), 3.57(s,2H), 3.90(s, 3H), 3.97(s,6H), 7.20–7.34(m,7H), 7.63(s,1H), 8.58(d,1H, J=5.1 Hz).

m/z (EI): 489 [M$^+$].

EXAMPLE 9

Synthesis of N-(3-methoxybenzyl)-N'-[[2-(3,4,5-trimethoxyphenyl)pyridin-4-yl)methyl]piperazine dimaleate

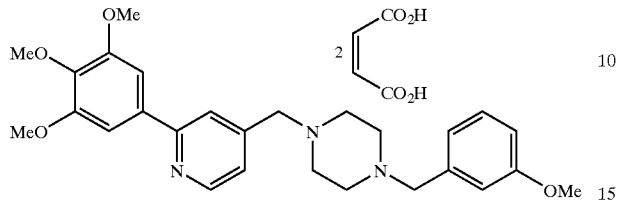

1-[[2-(3,4,5-Trimethoxyphenyl)pyridin-4-yl]methyl]-piperazine (172 mg) and 3-methoxybenzyl bromide (121 mg) were reacted in the same manner as in Example 1 to produce a maleate, thereby obtaining the title compound.

Yield: 46 mg (13%).

$^1$H-NMR (measured as a free base, 400 MHz, CDCl$_3$) δ: 2.40–2.62(m,8H), 3.51(s,2H), 3.57(s,2H), 3.81(s,3H), 3.90 (s,3H), 3.97(s,6H), 6.79–6.91(m,3H), 7.20–7.24(m,4H), 7.63(s,1H), 8.59(d,1H,J=4.9 Hz).

m/z (EI): 463 [M$^+$].

EXAMPLE 10

Synthesis of N-(4-nitrobenzyl)-N'-[[2-(3,4,5-trimethoxyphenyl)pyridin-4-yl]methyl]piperazine dimaleate

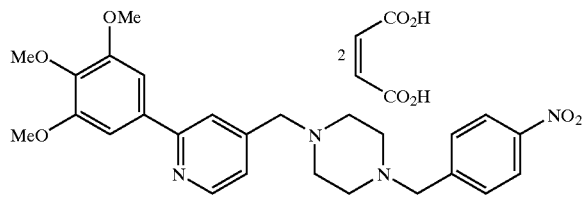

1-[[2-(3,4,5-Trimethoxyphenyl)pyridin-4-yl]methyl]-piperazine (113 mg) and 4-nitrobenzyl bromide (130 mg) were reacted in the same manner as in Example 1 to produce a maleate, thereby obtaining the title compound.

Yield: 53 mg (15%).

$^1$H-NMR (measured as a free base, 400 MHz, CDCl$_3$) δ: 2.43–2.63(m,8H), 3.59(s,2H), 3.61(s,2H), 3.91(s,3H), 4.00 (s,6H), 7.22(d,1H,J=4.9 Hz), 7.24(s,2H), 7.51(d,2H,J=8.6 Hz), 7.64(s,1H), 8.17(d,2H,J=8.8 Hz), 8.60(d,1H,J=4.9 Hz).

m/z (EI): 478 [M$^+$].

EXAMPLE 11

Synthesis of N-(4-fluorobenzyl)-N'-[[2-(3,4,5-trimethoxyphenyl)pyridin-4-yl]methyl]piperazine dimaleate

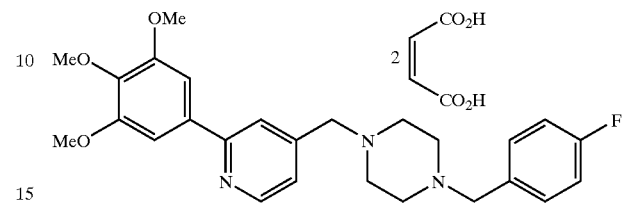

1-[[2-(3,4,5-Trimethoxyphenyl)pyridin-4-yl]methyl]-piperazine (172 mg) and 4-fluorobenzyl bromide (113 mg) were reacted in the same manner as in Example 1 to produce a maleate, thereby obtaining the title compound.

Yield: 91 mg (27%).

$^1$H-NMR (measured as a free base, 400 MHz, CDCl$_3$) δ: 2.25–2.74(m,8H), 3.48(s,2H), 3.57(s,2H), 3.90(s,3H), 3.97 (s,6H), 6.99(t,2H,J=8.8 Hz), 7.21(d,1H,J=5.1 Hz), 7.24–7.28(m,4H), 7.64(s,1H), 8.59(d,1H,J=4.9 Hz)

m/z (EI): 451[M$^+$].

EXAMPLE 12

Synthesis of N-(4-chlorobenzyl)-N'-[[2-(3,4,5-trimethoxyphenyl)pyridin-4-yl]methyl]piperazine dimaleate

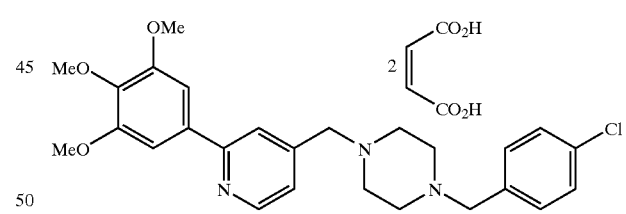

1-[[2-(3,4,5-Trimethoxyphenyl)pyridin-4-yl]methyl]-piperazine (172 mg) and 4-chlorobenzyl bromide (97 mg) were reacted in the same manner as in Example 1 to produce a maleate, thereby obtaining the title compound.

Yield: 60 mg (17%).

$^1$H-NMR (measured as a free base, 400 MHz, CDCl$_3$) δ: 2.36–2.62(m,8H), 3.48(s,2H), 3.57(s,2H), 3.90(s,3H), 3.97 (s,6H), 7.18–7.37(m,7H), 7.62(s,1H), 8.59(d,1H,J=5.1 Hz).

m/z (EI): 467, 469 [M$^+$].

EXAMPLE 13

Synthesis of N-(2-chlorobenzyl)-N'-[[2-(3,4,5-trimethoxy-phenyl)pyridin-4-yl]methyl]piperazine trihydrochloride

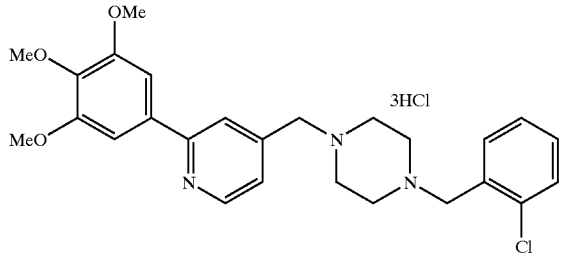

1-[[2-(3,4,5-Trimethoxyphenyl)pyridin-4-yl]methyl]-piperazine (172 mg) and 2-chlorobenzyl bromide (81 mg) were reacted in the same manner as in Example 1 to produce a hydrochloride, thereby obtaining the title compound.

Yield: 28 mg (12%).

$^1$H-NMR (measured as a trihydrochloride, 400 MHz, MeOH-$d_6$) δ: 3.11(br,4H), 3.57(br,4H), 3.86(s,3H), 3.98(s,6H), 4.19(s,2H), 4.60(s,2H), 7.31(s,2H), 7.45–7.53(m,2H), 7.59(dd,1H,J=7.9 Hz,1.5 Hz), 7.76(dd,1H,J=7.4 Hz,2.0 Hz), 8.08(d,1H,J=6.2 Hz), 8.50(s,1H), 8.76(d,1H,J=6.2 Hz).

m/z (EI): 467¤ 469 [M$^+$].

EXAMPLE 14

Synthesis of N-(2,6-dichlorobenzyl)-N'-[[2-(3,4,5-trimethoxyphenyl)pyridin-4-yl]methyl]piperazine dimaleate

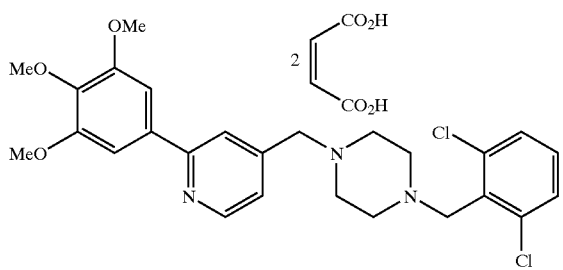

1-[[2-(3,4,5-Trimethoxyphenyl)pyridin-4-yl]methyl]-piperazine (172 mg) and 2,6-dichlorobenzyl bromide (144 mg) were reacted in the same manner as in Example 1 to produce a maleate, thereby obtaining the title compound.

Yield: 138 mg (19%).

$^1$H-NMR (measured as a free base, 400 MHz, CDCl$_3$) δ: 2.36–2.55(m,4H), 2.58–2.84(m,4H), 3.54(s,2H), 3.56(s,2H), 3.90(s,3H), 3.97(s,6H), 7.12(t,1H,J=8.0 Hz), 7.20–7.30(m,5H), 7.64(s,1H), 8.59(d,1H,J=5.1 Hz).

m/z (EI): 501, 503, 505 [M$^+$].

EXAMPLE 15

Synthesis of N-(4-pyridylmethyl)-N'-[[2-(3,4,5-trimethoxyphenyl)pyridin-4-yl]methyl]piperazine dimaleate

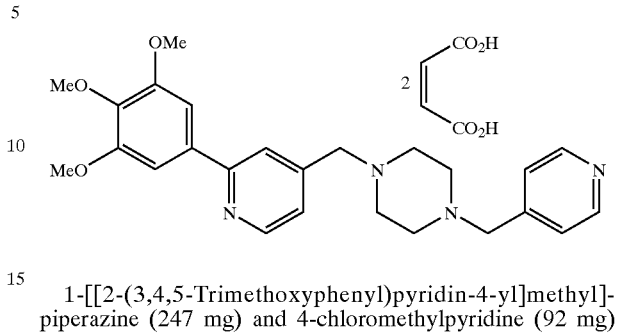

1-[[2-(3,4,5-Trimethoxyphenyl)pyridin-4-yl]methyl]-piperazine (247 mg) and 4-chloromethylpyridine (92 mg) were reacted in the same manner as in Example 1 to produce a maleate, thereby obtaining the title compound.

Yield: 170 mg (35%).

$^1$H-NMR (measured as a free base, 400 MHz, CDCl$_3$) δ: 2.39–2.68(m,8H), 3.51(s,2H), 3.58(s,2H), 3.90(s,3H), 3.97(s,6H), 7.22(d,1H,J=5.1 Hz), 7.25(s,2H), 7.27(d,2H,J=5.5 Hz), 7.64(s,1H), 8.53(d,2H,J=6.1 Hz), 8.60(d,1H,J=4.9 Hz) m/z (EI): 434 [M$^+$].

EXAMPLE 16

Synthesis of N-(2-naphthylmethyl)-N'-[[2-(3,4,5-trimethoxyphenyl)pyridin-4-yl]methyl]piperazine dimaleate

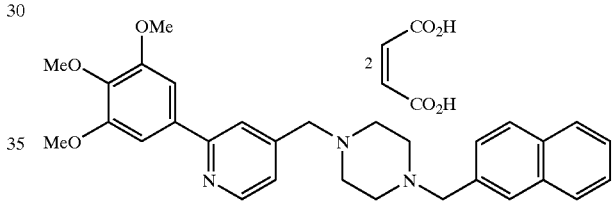

1-[[2-(3,4,5-Trimethoxyphenyl)pyridin-4-yl]methyl]-piperazine (172 mg) and 2-bromomethylnaphthalene (132 mg) were reacted in the same manner as in Example 1 to produce a maleate, thereby obtaining the title compound.

Yield: 34 mg (10%).

$^1$H-NMR (measured as a free base, 400 MHz, CDCl$_3$) δ: 2.43–2.68(m,8H), 3.57(s,2H), 3.69(s,2H), 3.90(s,3H), 3.96(s,6H), 7.21(d,1H,J=4.9 Hz), 7.23(s,2H), 7.44–7.49(m,3H), 7.63(s,1H), 7.73(s,1H), 7.79–7.83(m,3H), 8.59(d,1H,J=5.1 Hz).

m/z (EI) : 483 [M$^+$].

Preparation Example 13

Synthesis of ethyl 2-(3,4,5-trimethoxyphenyl)benzoate 3,4,5-Trimethoxyphenylboronic acid (7.1 g) and ethyl 2-bromobenzoate (7.0 g) were treated in the same manner as in Preparation Example 1 to obtain the title compound.

Yield: 4.16 g (43%).

$^1$H-NMR (400 MHz, CDCl$_3$) δ: 1.02(t,3H,J=7.1 Hz), 3.83(s,3H), 3.86(s,6H), 4.09(q,2H,J=7.1 Hz), 6.52(s,2H), 7.36–7.29(m,3H), 7.74(d,1H,J=7.8 Hz).

Preparation Example 14

Synthesis of 2-(3,4,5-trimethoxyphenyl)benzyl alcohol

Ethyl 2-(3,4,5-trimethoxyphenyl)benzoate (655 mg) was treated in the same manner as in Preparation Example 2 to obtain the title compound.

Yield: 630 mg (theoretical amount).
$^1$H-NMR (400 MHz, CDCl$_3$) δ: 3.85(s,6H), 3.90(s,3H), 4.61(s,2H), 6.61(s,2H), 7.26–7.39(m,3H), 7.53(d,1H,J=6.8 Hz).

Preparation Example 15

Synthesis of 2-(3,4,5-trimethoxyphenyl)benzyl chloride 2-(3,4,5-Trimethoxyphenyl)benzyl alcohol (630 mg) was treated in the same manner as in Preparation Example 3 to obtain the title compound.

Yield: 615 mg (theoretical amount).
$^1$H-NMR (400 MHz, CDCl$_3$) δ: 3.87(s,6H), 3.90(s,3H), 4.53(s,2H), 6.66(s,2H), 7.29–7.32(m,1H), 7.34–7.39(m,2H), 7.50–7.52(m,1H).

EXAMPLE 17

Synthesis of N-[2-(3,4,5-trimethoxyphenyl)benzyl]-N'-[[2-(3,4,5-trimethoxyphenyl)pyridin-4-yl]methyl]piperazine trihydrochloride

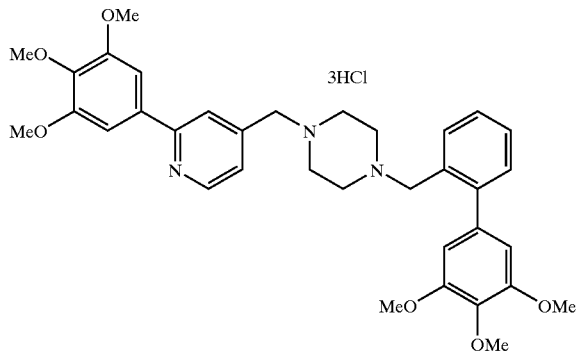

1-[[2-(3,4,5-Trimethoxyphenyl)pyridin-4-yl]-methyl]piperazine (103 mg) and 2-(3,4,5-trimethoxyphenyl)-benzyl chloride (114 mg) were reacted in the same manner as in Example 1 to produce a hydrochloride, thereby obtaining the title compound.

Yield: 52 mg (24%).
$^1$H-NMR (measured as a free base, 400 MHz, CDCl$_3$) δ: 2.35–2.63(m,8H), 3.44(s,2H), 3.55(s,2H), 3.86(s,6H), 3.90(s,3H), 3.91(s,3H), 3.97(s,6H), 6.68(s,2H), 7.20(d,1H,J=5.1 Hz), 7.24(s,2H), 7.28–7.36(m,3H), 7.47(s,1H), 7.62(s,1H), 8.59(d,1H,J=5.1 Hz).
m/z (EI): 599 [M$^+$].

Preparation Example 16

Synthesis of ethyl 3-(3,4,5-trimethoxyphenyl)benzoate 3,4,5-Trimethoxyphenylboronic acid (3.7 g) and ethyl 3-bromobenzoate (4.02 g) were reacted in the same manner as in Preparation Example 1 to obtain the title compound.

Yield: 5.09 g (92%).
$^1$H-NMR (400 MHz, CDCl$_3$) δ: 1.42(t,3H,J=7.1 Hz), 3.90(s,3H), 3.94(s,6H), 4.41(q,2H,J=7.1 Hz), 6.79(s,2H), 7.50(t,1H,J=7.8 Hz), 7.73(dt,1H,J=7.1 Hz,1.5 Hz), 8.01(dt,1H,J=7.8 Hz,1.4 Hz), 8.23(t,1H,J=1.8 Hz).

Preparation Example 17

Synthesis of 3-(3,4,5-trimethoxyphenyl)benzyl alcohol

Ethyl 3-(3,4,5-trimethoxyphenyl)benzoate (5.09 g) was treated in the same manner as in Preparation Example 2 to obtain the title compound.

Yield: 4.25 g (97%).
$^1$H-NMR (400 MHz, CDCl$_3$) δ: 1.87(t,1H,J=6.0 Hz), 3.89(s,3H), 3.92(s,6H), 4.76(d,2H,J=5.6 Hz), 6.77(s,2H), 7.34(d,1H,J=7.4 Hz), 7.42(t,1H,J=7.5 Hz), 7.48(d,1H,J=7.6 Hz), 7.55(s,1H).

Preparation Example 18

Synthesis of 3-(3,4,5-trimethoxyphenyl)benzyl chloride 3-(3,4,5-Trimethoxyphenyl)benzyl alcohol (1.21 g) was treated in the same manner as in Preparation Example 3 to obtain the title compound.

Yield: 893 mg (69.2%).
$^1$H-NMR (400 MHz, CDCl$_3$) δ: 3.87(s,3H), 3.90(s,6H), 4.62(s,2H), 6.75(s,2H), 7.33(d,1H,J=7.6 Hz), 7.39(t,1H,J=7.7 Hz), 7.48(d,1H,J=7.6 Hz), 7.54(s,1H).

EXAMPLE 18

Synthesis of N-[3-(3,4,5-trimethoxyphenyl)benzyl]-N'-[[2-(3,4,5-trimethoxyphenyl)pyridin-4-yl]methyl]piperazine difumarate

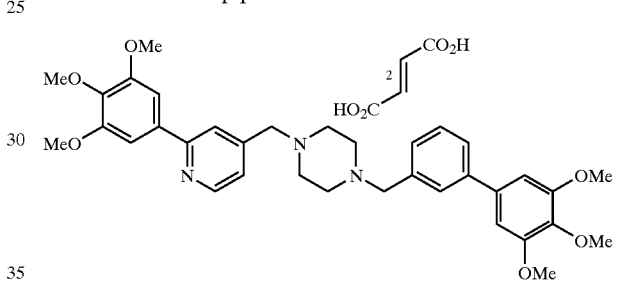

1-[[2-(3,4,5-Trimethoxyphenyl)pyridin-4-yl]-methyl]piperazine (274 mg) and 3-(3,4,5-trimethoxyphenyl)-benzyl chloride (193 mg) were reacted in the same manner as in Example 1 to produce a fumarate, thereby obtaining the title compound.

Yield: 239 mg (44%).
$^1$H-NMR (measured as a fumarate, 400 MHz, DMSO-d$_6$) δ: 2.48–2.52(m,8H), 3.59(s,4H), 3.76(s,3H), 3.78(s,3H), 3.86(s,6H), 3.88(s,6H), 6.63(s,4H), 6.85(s,2H), 7.21–7.35(m,3H), 7.33(s,2H), 7.46–7.51(m,2H), 7.73(s,1H), 8.52(d,1H,J=4.9 Hz).
m/z (EI): 599 [M$^+$].

Preparation Example 19

Synthesis of 1-[[2-(3,4,5-trimethoxyphenyl)pyridin-4-yl]-methyl]homopiperazine

4-Chloromethyl-2-(3,4,5-trimethoxyphenyl)pyridine (588 mg) and homopiperazine (801 mg) were treated in the same manner as in Preparation Example 4 to obtain the title compound.

Yield: 436 mg (61%).

EXAMPLE 19

Synthesis of N-[3-(3,4,5-trimethoxyphenyl)benzyl]-N'-[[2-(3,4,5-trimethoxyphenyl)pyridin-4-yl]methyl]homopiperazine difumarate

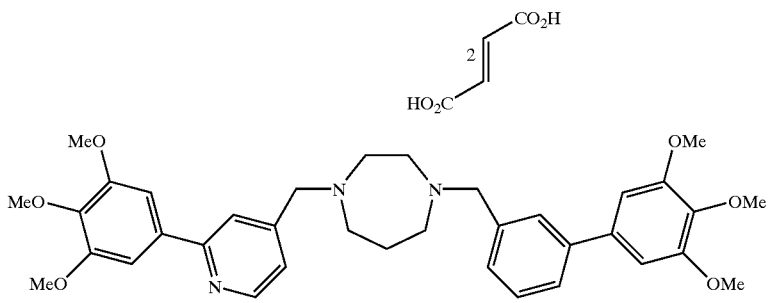

1-[[2-(3,4,5-Trimethoxyphenyl)pyridin-4-yl]-methyl] homopiperazine (257 mg) and 3-(3,4,5-trimethoxyphenyl)benzyl chloride (210 mg) were reacted in the same manner as in Example 1 to produce a fumarate, thereby obtaining the title compound.

Yield: 248 mg (41%).

$^1$H-NMR (measured as a fumarate, 400 MHz, DMSO-$d_6$) δ: 1.78–1.84(m,2H), 2.77–2.83(m,8H), 3.76(s,3H), 3.76(s,2H), 3.77(s,2H), 3.78(s,3H), 3.86(s,6H), 3.87(s,6H), 6.63(s,4H), 6.85(s,2H), 7.23(d,1H,J=4.9 Hz), 7.28–7.36(m,2H), 7.33(s,2H), 7.46(dt,1H,J=7.6 Hz,3.2 Hz), 7.55(s,1H), 7.75(s,1H), 8.52(d,1H,J=4.9 Hz).

m/z (EI): 613 [M$^+$].

Preparation Example 22

Synthesis of 4-(3,4,5-trimethoxyphenyl)benzyl chloride 4-(3,4,5-Trimethoxyphenyl)benzyl alcohol (1.83 g) was treated in the same manner as in Preparation Example 3 to obtain the title compound.

Yield: 1.65 g (84%).

$^1$H-NMR (400 MHz, CDCl$_3$) δ: 3.90(s,3H), 3.93(s,6H), 4.65(s,2H), 6.77(s,2H), 7.46(d,2H,J=8.0 Hz), 7.55(d,2H,J=8.0 Hz).

EXAMPLE 20

Synthesis of N-[4-(3,4,5-trimethoxyphenyl)benzyl]-N'-[[2-(3,4,5-trimethoxyphenyl)pyridin-4-yl]methyl]piperazine dimaleate

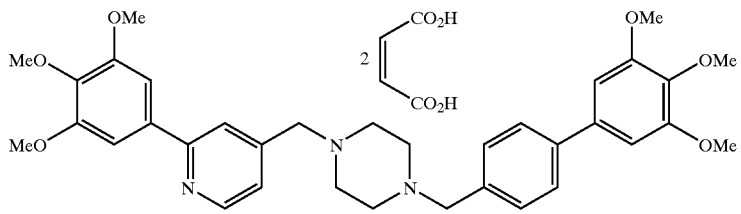

Preparation Example 20

Synthesis of ethyl 4-(3,4,5-trimethoxyphenyl)benzoate 3,4,5-Trimethoxyphenylboronic acid (2.01 g) and ethyl 4-bromobenzoate (2.29 g) were reacted in the same manner as in Preparation Example 1 to obtain the title compound.

Yield: 2.99 g (95%).

$^1$H-NMR (400 MHz, CDCl$_3$) δ: 1.42(t,3H,J=7.2 Hz), 3.90(s,3H), 3.94(s,6H), 4.38(q,2H,J=7.2 Hz), 6.81(s,2H), 7.62(d,2H,J=8.2 Hz), 8.10(d,2H,J=8.2 Hz).

Preparation Example 21

Synthesis of 4-(3,4,5-trimethoxyphenyl)benzyl alcohol

Ethyl 4-(3,4,5-trimethoxyphenyl)benzoate (2.99 g) was treated in the same manner as in Preparation Example 2 to obtain the title compound.

Yield: 1.83 g.

1-[[2-(3,4,5-Trimethoxyphenyl)pyridin-4-yl]-methyl]piperazine (343 mg) and 4-(3,4,5-trimethoxyphenyl)-benzyl chloride (293 mg) were reacted in the same manner as in Example 1 to produce a maleate, thereby obtaining the title compound.

Yield: 169 mg (41%).

$^1$H-NMR (measured as a maleate, 400 MHz, DMSO-$d_6$) δ: 2.79(t,4H,J=4.9 Hz), 3.03(t,4H,J=5.1 Hz), 3.76(s,3H), 3.78(s,3H), 3.79(s,2H), 3.87(s,6H), 3.89(s,6H), 4.09(s,2H), 6.14(s,4H), 6.91(s,2H), 7.28(d,1H,J=4.9 Hz), 7.36(s,2H), 7.49(d,2H,J=8.4 Hz), 7.68(d,2H,J=8.4 Hz), 7.80(s,1H), 8.60(d,1H, J=5.1 Hz).

m/z (EI): 599 [M$^+$].

Preparation Example 23

Synthesis of ethyl 2-phenylisonicotinate

Phenylboronic acid (147 mg) and ethyl 2-chloroisonicotinate (200 mg) were treated in the same manner as in Preparation Example 1 to obtain the title compound.

Yield: 230 mg (94%).

$^1$H-NMR (400 MHz, CDCl$_3$) δ: 1.43(t,3H,J=7.1 Hz), 4.44(q,2H,J=7.2 Hz), 7.42–7.51(m,3H), 7.77(dd,1H,J=5.0 Hz,1.5 Hz), 8.04–8.06(m,2H), 8.29(d,1H,J=1.0 Hz), 8.83(d,1H,J=0.8 Hz).

Preparation Example 24

Synthesis of 4-hydroxymethyl-2-phenylpyridine

Ethyl 2-phenylisonicotinate (230 mg) was treated in the same manner as in Preparation Example 2 to obtain the title compound.

Yield: 165 mg (88%).

$^1$H-NMR (400 MHz, CDCl$_3$) δ: 4.74(s,2H), 7.22(d,1H,J= 4.5 Hz), 7.66–7.70(m,4H), 8.01(d,2H,J=8.4 Hz), 8.56(d,1H, J=5.1 Hz).

Preparation Example 25

Synthesis of 4-chloromethyl-2-phenylpyridine

4-Hydroxymethyl-2-phenylpyridine (165 mg) was treated in the same manner as in Preparation Example 3 to obtain the title compound.

Yield: 167 mg (92%).

$^1$H-NMR (400 MHz, CDCl$_3$) δ: 4.56(s,2H), 7.22(d,1H,J= 4.9 Hz), 7.39–7.49(m,3H), 7.71(s,1H), 7.99(d,2H,J=7.0 Hz), 8.66(d,1H,J=4.9 Hz)

EXAMPLE 21

Synthesis of N-[(2-phenylpyridin-4-yl)methyl]-N'-[[2-(3,4,5-trimethoxyphenyl)pyridin-4-yl]methyl] piperazine difumarate

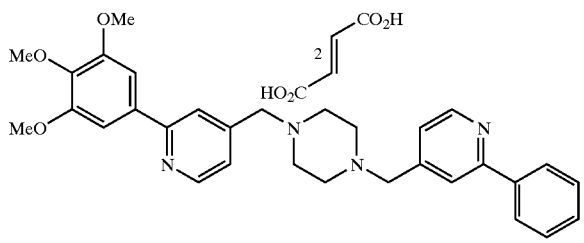

1-[[2-(3,4,5-Trimethoxyphenyl)pyridin-4-yl]-methyl] piperazine (226 mg) and 4-chloromethyl-2-phenyl-pyridine (102 mg) were reacted in the same manner as in Example 1 to produce a fumarate, thereby obtaining the title compound.

Yield: 133 mg (36%).

$^1$H-NMR (measured as a fumarate, 400 MHz, DMSO-d$_6$) δ: 2.49(s,8H), 3.56(s,4H), 3.73(s,3H), 3.83(s,6H), 6.59(s, 4H), 7.17–7.20(m,2H), 7.29(s,2H), 7.32–7.42(m,3H), 7.69 (s,1H), 7.72(s,1H), 7.96(s,1H), 7.98(s,1H), 8.48(d,1H,J=4.9 Hz), 8.51(d,1H,J=5.1 Hz).

m/z (EI) : 510 [M$^+$].

Preparation Example 26

Synthesis of ethyl 2-(4-methylphenyl)isonicotinate

4-Methylphenylboronic acid (161 mg) and ethyl 2-chloroisonicotinate (200 mg) were treated in the same manner as in Preparation Example 1 to obtain the title compound.

Yield: 239 mg (92%).

$^1$H-NMR (400 MHz, CDCl$_3$) δ: 1.40(t,3H,J=7.1 Hz), 2.38(s,3H), 4.41(q,2H,J=7.2 Hz), 7.27(d,2H,J=7.7 Hz), 7.72 (d,1H,J=5.1 Hz), 7.94(d,2H,J=8.2 Hz), 8.25(s,1H), 8.78(d, 1H,J=5.1 Hz).

Preparation Example 27

Synthesis of 4-hydroxymethyl-2-(4-methylphenyl) pyridine

Ethyl 2-(4-methylphenyl)isonicotinate (239 mg) was treated in the same manner as in Preparation Example 2 to obtain the title compound.

Yield: 190 mg (96%).

$^1$H-NMR (400 MHz, CDCl$_3$) δ: 2.34(s,3H), 4.62(s,2H), 7.06(d,1H,J=4.9 Hz), 7.19(d,2H,J=7.8 Hz), 7.56(s,1H), 7.73 (d,2H,J=7.8 Hz), 8.43(d,1H,J=4.9 Hz).

Preparation Example 28

Synthesis of 4-chloromethyl-2-(4-methylphenyl) pyridine

4-Hydroxymethyl-2-(4-methylphenyl)pyridine (190 mg) was treated in the same manner as in Preparation Example 3 to obtain the title compound.

Yield: 178 mg (86%).

EXAMPLE 22

Synthesis of N-[[2-(4-methylphenyl)pyridin-4-yl] methyl]-N'-[[2-(3,4,5-trimethoxyphenyl)pyridin-4-yl]methyl]-piperazine dimaleate

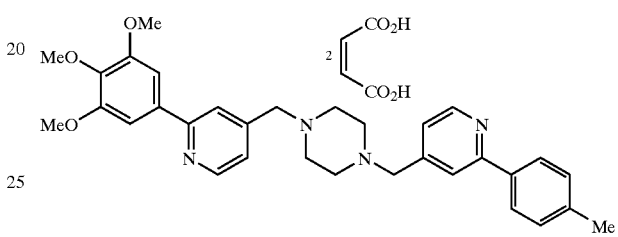

1-[[2-(3,4,5-Trimethoxyphenyl)pyridin-4-yl]-methyl] piperazine (289 mg) and 4-chloromethyl-2-(4-methylphenyl)pyridine (183 mg) were reacted in the same manner as in Example 1 to produce a maleate, thereby obtaining the title compound.

Yield: 323 mg (51%).

$^1$H-NMR (measured as a maleate, 400 MHz, DMSO-d$_6$) δ: 2.37(s,3H), 2.85(br,8H), 3.78(s,3H), 3.89(s,6H), 3.90(s, 2H), 4.08(s,2H), 6.16(s,4H), 7.28–7.31(m,4H), 7.36(s,2H), 7.83–7.84(m,2H), 7.94(d,2H,J=8.4 Hz), 8.61(d,2H,J=5.1 Hz).

m/z (EI): 524 [M$^+$].

Preparation Example 29

Synthesis of ethyl 2-(2-methoxyphenyl)isonicotinate

2-Methoxyphenylboronic acid (1.00 g) and ethyl 2-chloroisonicotinate (1.20 g) were treated in the same manner as in Preparation Example 1 to obtain the title compound.

Yield: 480 mg (28%).

Preparation Example 30

Synthesis of 4-hydroxymethyl-2-(2-methoxyphenyl) pyridine

Ethyl 2-(2-methoxyphenyl)isonicotinate (480 mg) was treated in the same manner as in Preparation Example 2 to obtain the title compound.

Yield: 206 mg (51%).

Preparation Example 31

Synthesis of 4-chloromethyl-2-(2-methoxyphenyl) pyridine

4-Hydroxymethyl-2-(2-methoxyphenyl)pyridine (206 mg) was treated in the same manner as in Preparation Example 3 to obtain the title compound Yield: 143 mg (64%)..

$^1$H-NMR (400 MHz, CDCl$_3$) δ: 3.86(s,3H), 4.58(s,2H), 7.00(d,1H,J=7.0 Hz), 7.06–7.10(m,1H), 7.23(d,1H,J=3.3 Hz), 7.36–7.38(m,1H), 7.77(dd,1H,J=7.6 Hz,2.0 Hz), 7.83 (s,1H), 8.68(d,1H,J=5.1 Hz).

EXAMPLE 23

Synthesis of N-[[2-(2-methoxyphenyl)pyridin-4-yl] methyl]-N'-[[2-(3,4,5-trimethoxyphenyl)pyridin-4-yl]methyl]-piperazine dimaleate

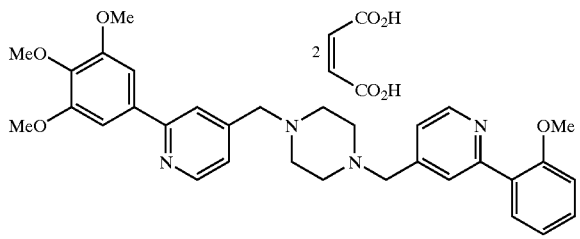

1-[[2-(3,4,5-Trimethoxyphenyl)pyridin-4-yl]-methyl] piperazine (66 mg) and 4-chloromethyl-2-(2-methoxyphenyl)pyridine (45 mg) were reacted in the same manner as in Example 1 to produce a maleate, thereby obtaining the title compound.

Yield: 54 mg (36%).

$^1$H-NMR (measured as a free base, 400 MHz, CDCl$_3$) δ: 2.90–3.25(m,8H), 3.58(s,4H), 3.84(s,3H), 3.90(s,3H), 3.97 (s,6H), 7.00(d,1H,J=8.2 Hz), 7.07(m,1H), 7.19–7.24(m,4H), 7.33–7.40(m,1H), 7.64(s,1H), 7.72–7.74(m,2H), 8.60(d,1H, J=5.1 Hz), 8.62(d,1H,J=4.5 Hz).

m/z (EI): 540 [M$^+$].

Preparation Example 32

Synthesis of ethyl 2-(3-methoxyphenyl)isonicotinate

3-Methoxyphenylboronic acid (1.00 g) and ethyl 2-chloroisonicotinate (1.20 g) were treated in the same manner as in Preparation Example 1 to obtain the title compound.

Yield: 790 mg (47%).

$^1$H-NMR (400 MHz, CDCl$_3$) δ: 1.43(t,3H,J=7.1 Hz), 3.88(s,3H), 4.44(q,2H,J=7.1 Hz), 6.99(d,1H,J=8.2 Hz), 7.39 (t,1H,J=7.9 Hz), 7.59–7.64(m,2H), 7.78(d,1H,J=5.1 Hz), 8.28(s,1H), 8.81(d,1H,J=4.9 Hz).

Preparation Example 33

Synthesis of 4-hydroxymethyl-2-(3-methoxyphenyl) pyridine

Ethyl 2-(3-methoxyphenyl)isonicotinate (705 mg) was treated in the same manner as in Preparation Example 2 to obtain the title compound.

Yield: 324 mg (55%).

Preparation Example 34

Synthesis of 4-chloromethyl-2-(3-methoxyphenyl) pyridine

4-Hydroxymethyl-2-(3-methoxyphenyl)pyridine (324 mg) was treated in the same manner as in Preparation Example 3 to obtain the title compound.

Yield: 247 mg (70%).

$^1$H-NMR (400 MHz, CDCl$_3$) δ: 3.17(s,3H), 4.56(s,2H), 6.97(d,1H,J=7.2 Hz), 7.22(d,1H,J=5.1 Hz), 7.37(t,1H,J=7.9 Hz), 7.53–7.59(m,2H), 7.70(s,1H), 8.66(d,1H,J=5.1 Hz).

EXAMPLE 24

Synthesis of N-[[2-(3-methoxyphenyl)pyridin-4-yl] methyl]-N'-[[2-(3,4,5-trimethoxyphenyl)pyridin-4-yl]methyl]-piperazine dimaleate

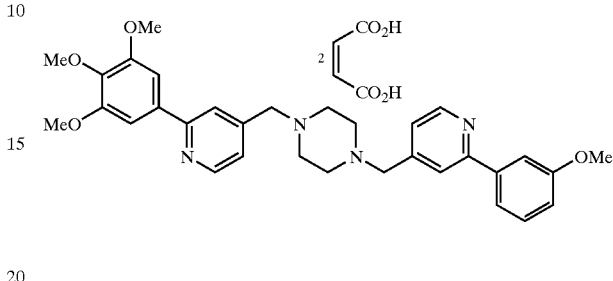

1-[[2-(3,4,5-Trimethoxyphenyl)pyridin-4-yl]-methyl] piperazine (216 mg) and 4-chloromethyl-2-(3-methoxyphenyl)pyridine (147 mg) were reacted in the same manner as in Example 1 to produce a maleate, thereby obtaining the title compound.

Yield: 157 mg (32%).

$^1$H-NMR (measured as a free base, 400 MHz, CDCl$_3$) δ: 2.46–2.64(m,8H), 3.57(s,2H), 3.58(s,2H), 3.88(s,3H), 3.90 (s,3H), 3.96(s,6H), 6.96(d,1H,J=7.4 Hz), 7.22–7.25(m,4H), 7.35–7.39(m,1H), 7.54–7.60(m,2H), 7.65(s,1H), 7.70(s,1H), 8.59–8.61(m,2H).

m/z (EI): 540 [M$^+$].

Preparation Example 35

Synthesis of ethyl 2-(4-methoxyphenyl)isonicotinate

4-Methoxyphenylboronic acid (179 mg) and ethyl 2-chloroisonicotinate (200 mg) were treated in the same manner as in Preparation Example 1 to obtain the title compound.

Yield: 225 mg (81%).

$^1$H-NMR (400 MHz, CDCl$_3$) δ: 1.42(t,3H,J=7.1 Hz), 3.85(s,3H), 4.43(q,2H,J=7.1 Hz), 7.00(d,2H,J=8.6 Hz), 7.70 (dd,1H,J=5.0 Hz), 8.01(d,2H,J=8.6 Hz), 8.22(s,1H), 8.77(d, 1H,J=5.1 Hz).

Preparation Example 36

Synthesis of 4-hydroxymethyl-2-(4-methoxyphenyl) pyridine

Ethyl 2-(4-methoxyphenyl)isonicotinate (227 mg) was treated in the same manner as in Preparation Example 2 to obtain the title compound.

Yield: 184 mg (97%).

$^1$H-NMR (400 MHz, CDCl$_3$) δ: 3.80(s,3H), 4.65(s,2H), 6.91(d,2H,J=8.8 Hz), 7.06(d,1H,J=4.1 Hz), 7.55(s,1H), 7.81 (d,2H,J=8.8 Hz), 8.45(d,1H,J=5.1 Hz).

Preparation Example 37

Synthesis of 4-chloromethyl-2-(4-methoxyphenyl) pyridine

4-Hydroxymethyl-2-(4-methoxyphenyl)pyridine (184 mg) was treated in the same manner as in Preparation Example 3 to obtain the title compound.

Yield: 176 mg (88%).

EXAMPLE 25

Synthesis of N-[[2-(4-methoxyphenyl)pyridin-4-yl]methyl]-N'-[[2-(3,4,5-trimethoxyphenyl)pyridin-4-yl]methyl]-piperazine difumarate

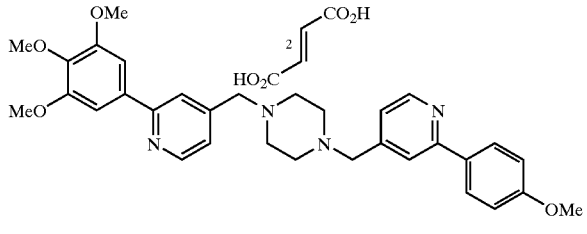

1-[[2-(3,4,5-Trimethoxyphenyl)pyridin-4-yl]-methyl] piperazine (216 mg) and 4-chloromethyl-2-(4-methoxyphenyl)pyridine (147 mg) were reacted in the same manner as in Example 1 to produce a fumarate, thereby obtaining the title compound.

Yield: 157 mg (32%).

$^1$H-NMR (measured as a fumarate, 400 MHz, DMSO-$d_6$) δ: 2.49(s,8H), 3.55(s,2H), 3.57(s,2H), 3.73(s,3H), 3.78(s,3H), 3.83(s,6H), 6.60(s,4H), 6.97(d,2H,J=8.8 Hz), 7.14(d,1H,J=4.9 Hz), 7.19(d,1H,J=4.9 Hz), 7.30(s,2H), 7.66(s,1H), 7.72(s,1H), 7.93(d,2H,J=8.8 Hz), 8.47(d,1H,J=4.9 Hz), 8.50 (d,1H,J=4.9 Hz).

m/z (EI): 540 [M$^+$].

Preparation Example 38

Synthesis of ethyl 2-(3,4-dimethoxyphenyl)isonicotinate 3,4-Dimethoxyphenylboronic acid (215 mg) and ethyl 2-chloroisonicotinate (200 mg) were treated in the same manner as in Preparation Example 1 to obtain the title compound.

Yield: 277 mg (90%).

$^1$H-NMR (400 MHz, CDCl$_3$) δ: 1.35(t,3H,J=7.1 Hz), 3.86(s,3H), 3.92(s,3H), 4.36(q,2H,J=7.2 Hz), 6.89(d,1H,J=8.6 Hz), 7.52(dd,1H,J=8.4 Hz,2.1 Hz), 7.64(dd,1H,J=4.4 Hz,1.4 Hz), 7.64(s,1H), 8.16(s,1H), 8.70(d,1H,J=4.9 Hz).

Preparation Example 39

Synthesis of 2-(3,4-dimethoxyphenyl)-4-hydroxymethyl-pyridine

Ethyl 2-(3,4-dimethoxyphenyl)isonicotinate (227 mg) was treated in the same manner as in Preparation Example 2 to obtain the title compound.

Yield: 209 mg (88%).

$^1$H-NMR (400 MHz, CDCl$_3$) δ: 3.82(s,3H), 3.88(s,3H), 4.62(s,2H), 6.82(d,1H,J=8.4 Hz), 7.03(d,1H,J=4.7 Hz), 7.34 (dd,1H,J=8.3 Hz,1.9 Hz), 7.50(d,1H,J=1.8 Hz), 7.54(s,1H), 8.42(d,1H,J=4.9 Hz).

Preparation Example 40

Synthesis of 4-chloromethyl-2-(3,4-dimethoxyphenyl)-pyridine 2-(3,4-Dimethoxyphenyl)-4-hydroxymethylpyridine (209 mg) was treated in the same manner as in Preparation Example 3 to obtain the title compound.

Yield: 178 mg (80%).

EXAMPLE 26

Synthesis of N-[[2-(3,4-dimethoxyphenyl)pyridin-4-yl]methyl]-N'-[[2-(3,4,5-trimethoxyphenyl)pyridin-4-yl]methyl]piperazine difumarate

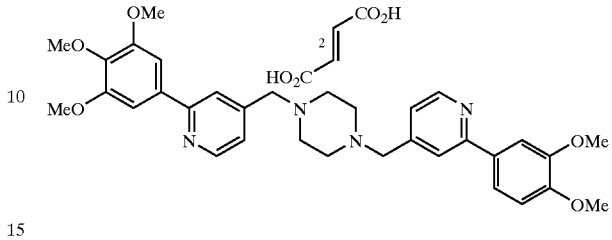

1-[[2-(3,4,5-Trimethoxyphenyl)pyridin-4-yl]-methyl] piperazine (226 mg) and 4-chloromethyl-2-(3,4-dimethoxyphenyl)pyridine (132 mg) were reacted in the same manner as in Example 1 to produce a fumarate, thereby obtaining the title compound.

Yield: 189 mg (47%).

$^1$H-NMR (measured as a fumarate, 400 MHz, DMSO-$d_6$) δ: 2.49(s,8H), 3.55(s,2H), 3.56(s,2H), 3.73(s,3H), 3.78(s,3H), 3.81(s,3H), 3.83(s,6H), 6.59(s,4H), 6.98(d,1H,J=8.3 Hz), 7.14(d,1H,J=4.9 Hz), 7.18(d,1H,J=4.9 Hz), 7.29(s,2H), 7.53(dd,1H,J=8.3 Hz,2.2 Hz), 7.62(d,1H,J=2.2 Hz), 7.66(s,1H), 7.70(s,1H), 8.46(d,1H,J=5.1 Hz), 8.49(d,1H,J=4.9 Hz).

m/z (EI): 570 [M$^+$].

Preparation Example 41

Synthesis of ethyl 2-(3,4,5-trimethoxyphenyl)nicotinate 3,4,5-Trimethoxyphenylboronic acid (694 mg) and ethyl 2-chloronicotinate (608 mg) were reacted in the same manner as in Preparation Example 1 to obtain the title compound.

Yield: 799 mg (77%).

$^1$H-NMR (400 MHz, CDCl$_3$) δ: 1.10(t,3H,J=7.2 Hz), 3.89(s,9H), 4.19(q,2H,J=7.2 Hz), 6.79(s,2H), 7.34(dd,1H,J=7.8 Hz,4.8 Hz), 8.06(dd,1H,J=7.8 Hz,1.7 Hz), 8.75(dd,1H,J=4.8 Hz,1.7 Hz).

Preparation Example 42

Synthesis of 3-hydroxymethyl-2-(3,4,5-trimethoxyphenyl)-pyridine

Ethyl 2-(3,4,5-trimethoxyphenyl)nicotinate (468 mg) was treated in the same manner as in Preparation Example 2 to obtain the title compound.

Yield: 293 mg (72%).

$^1$H-NMR (400 MHz, CDCl$_3$) δ: 3.90(s,9H), 4.72(s,2H), 6.83(s,2H), 7.32(dd,1H,J=7.9 Hz,4.8 Hz), 7.92(dd,1H,J=7.9 Hz,1.7 Hz), 8.62(dd,1H,J=4.8 Hz,1.7 Hz).

Preparation Example 43

Synthesis of 3-chloromethyl-2-(3,4,5-trimethoxyphenyl)-pyridine

3-Hydroxymethyl-2-(3,4,5-trimethoxyphenyl)pyridine (293 mg) was treated in the same manner as in Preparation Example 3 to obtain the title compound.

Yield: 311 mg (theoretical amount).

EXAMPLE 27

Synthesis of N-[[2-(3,4,5-trimethoxyphenyl)pyridin-3-yl]methyl]-N'-[[2-(3,4,5-trimethoxyphenyl)pyridin-4-yl]methyl]piperazine tetrahydrochloride

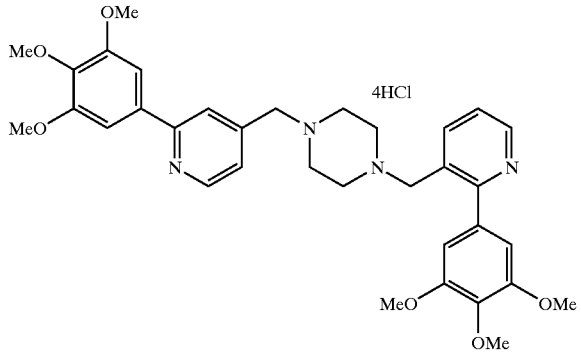

1-[[2-(3,4,5-Trimethoxyphenyl)pyridin-4-yl]-methyl]piperazine (103 mg) and 3-chloromethyl-2-(3,4,5-trimethoxyphenyl)pyridine (88 mg) were reacted in the same manner as in Example 1 to produce a hydrochloride, thereby obtaining the title compound.

Yield: 189 mg (47%).

$^1$H-NMR (measured asa free base, 400 MHz, CDCl$_3$) δ: 2.54(br,8H), 3.58(s,4H), 3.90(s,3H), 3.91(s,3H), 3.96(s,6H), 3.97(s,6H), 7.21(br,1H), 7.23(s,4H), 7.61–7.68(m,2H), 7.72 (d,1H,J=8.4 Hz), 8.56–8.62(m,2H).

m/z (EI) : 600 [M$^+$].

Preparation Example 44

Synthesis of ethyl 6-(3,4,5-trimethoxyphenyl)nicotinate 3,4,5-Trimethoxyphenylboronic acid (1.16 g) and ethyl 6-chloronicotinate (1.02 g) were reacted in the same manner as in Preparation Example 1 to obtain the title compound.

Yield: 1.42 g (82%).

$^1$H-NMR (400 MHz, CDCl$_3$) δ: 1.43(t,3H, J=7.2 Hz), 3.92(s,3H), 3.98(s,6H), 4.44(q,2H,J=7.2 Hz), 7.32(s,2H), 7.76(d,1H,J=8.3 Hz), 8.33(dd,1H,J=8.2 Hz,2.2 Hz), 9.26(d, 1H,J=2.2 Hz).

Preparation Example 45

Synthesis of 5-hydroxymethyl-2-(3,4,5-trimethoxyphenyl)-pyridine

Ethyl 6-(3,4,5-trimethoxyphenyl)nicotinate (658 mg) was treated in the same manner as in Preparation Example 2 to obtain the title compound.

Yield: 482 mg (85%).

$^1$H-NMR (400 MHz, CDCl$_3$) δ: 3.91(s,3H), 3.97(s,6H), 4.76(s,2H), 7.23(s,2H), 7.68(d,1H,J=7.4 Hz), 7.78(dd,1H,J= 7.4 Hz,2.3 Hz), 8.63(d,1H,J=2.3 Hz).

Preparation Example 46

Synthesis of 5-chloromethyl-2-(3,4,5-trimethoxyphenyl)-pyridine

5-Hydroxymethyl-2-(3,4,5-trimethoxyphenyl)pyridine (685 mg) was treated in the same manner as in Preparation Example 3 to obtain the title compound.

Yield: 717 mg (theoretical amount).

EXAMPLE 28

Synthesis of N-[[2-(3,4,5-trimethoxyphenyl)pyridin-5-yl]methyl]-N'-[[2-(3,4,5-trimethoxyphenyl)pyridin-4-yl]methyl]piperazine tetrahydrochloride

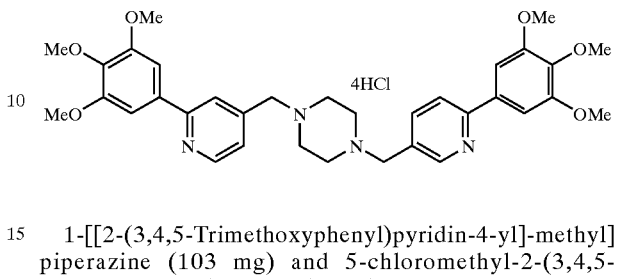

1-[[2-(3,4,5-Trimethoxyphenyl)pyridin-4-yl]-methyl]piperazine (103 mg) and 5-chloromethyl-2-(3,4,5-trimethoxyphenyl)pyridine (88 mg) were reacted in the same manner as in Example 1 to produce a hydrochloride, thereby obtaining the title compound.

Yield: 24 mg (11%).

$^1$H-NMR (measured as a freebase, 400 MHz, CDCl$_3$) δ: 2.50(br,8H), 3.49(s,2H), 3.56(s,2H), 3.89(s,6H), 3.90(s,3H), 3.93(s,3H), 3.97(s,6H), 6.94(s,2H), 7.20(d,1H,J=4.3 Hz), 7.23(s,2H), 7.25(br,1H), 7.62(s,1H), 7.80(d,1H,J=6.4 Hz), 8.57–8.62(m,2H).

m/z (EI): 600 [M$^+$].

Preparation Example 47

Synthesis of ethyl 5-(3,4,5-trimethoxyphenyl)nicotinate 3,4,5-Trimethoxyphenylboronic acid (6.36 g) and ethyl 5-chloronicotinate (6.90 g) were reacted in the same manner as in Preparation Example 1 to obtain the title compound.

Yield: 7.19 g (76%).

$^1$H-NMR (400 MHz, CDCl$_3$) δ: 1.44(t,3H,J=7.1 Hz), 3.91(s,3H), 3.95(s,6H), 4.46(q,2H,J=7.1 Hz), 6.79(s,2H), 8.44(t,1H,J=2.1 Hz), 8.96(d,1H,J=2.1 Hz), 9.18(d,1H,J=1.8 Hz).

Preparation Example 48

Synthesis of 3-hydroxymethyl-5-(3,4,5-trimethoxyphenyl)-pyridine

Ethyl 5-(3,4,5-trimethoxyphenyl)nicotinate (7.19 g) was treated in the same manner as in Preparation Example 2 to obtain the title compound.

Yield: 3.83 g (61.3%).

$^1$H-NMR (400 MHz, CDCl$_3$) δ: 3.88(s,3H), 3.89(s,6H), 4.39(br,1H), 4.80(s,2H), 6.72(s,2H), 7.89(t,1H,J=1.2 Hz), 8.47(d,1H,J=2.1 Hz), 8.63(d,1H,J=2.2 Hz).

Preparation Example 49

Synthesis of 3-chloromethyl-5-(3,4,5-trimethoxyphenyl)-pyridine

3-Hydroxymethyl-5-(3,4,5-trimethoxyphenyl)pyridine (2.85 g) was treated in the same manner as in Preparation Example 3 to obtain the title compound.

Yield: 1.97 g (65%).

$^1$H-NMR (400 MHz, CDCl$_3$) δ: 3.90(s,3H), 3.94(s,6H), 4.67(s,2H), 6.75(s,2H), 7.87(t,1H,J=2.1 Hz), 8.59(d,1H,J= 2.0 Hz), 8.76(d,1H,J=2.1 Hz)

EXAMPLE 29

Synthesis of N-[[5-(3,4,5-trimethoxyphenyl)pyridin-3-yl]methyl]-N'-[[2-(3,4,5-trimethoxyphenyl)pyridin-4-yl]methyl]piperazine tetrahydrochloride

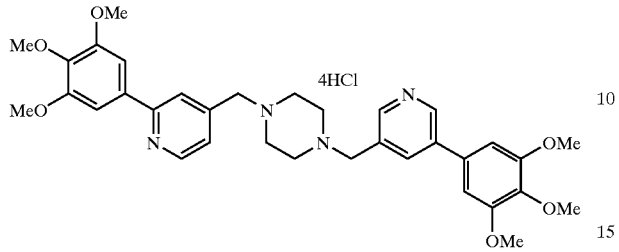

1-[[2-(3,4,5-Trimethoxyphenyl)pyridin-4-yl]-methyl]piperazine (103 mg) and 3-chloromethyl-5-(3,4,5-trimethoxyphenyl)pyridine (88 mg) were reacted in the same manner as in Example 1 to produce a hydrochloride, thereby obtaining the title compound.

Yield: 20 mg (9%).

$^1$H-NMR (measured as a free base, 400 MHz, CDC$_3$) δ: 2.64(br,8H), 3.62(s,2H), 3.68(s,2H), 3.90(s,6H), 3.95(s,6H), 3.97(s,6H), 6.80(s,2H), 7.22(dd,1H,J=4.9 Hz,1.2 Hz), 2.26 (s,2H), 7.69(s,1H), 7.93(s,1H), 8.51(d,1H,J=1.8 Hz), 8.60 (d,1H,J=4.9 Hz), 8.73(d,1H,J=2.2 Hz).

m/z (EI) : 600 [M$^+$].

Preparation Example 50

Synthesis of ethyl 2-(4-fluorophenyl)isonicotinate

4-Fluorophenylboronic acid (166 mg) and ethyl 2-chloroisonicotinate (200 mg) were reacted in the same manner as in Preparation Example 1 to obtain the title compound.

Yield: 226 mg (85%).

$^1$H-NMR (400 MHz, CDCl$_3$) δ: 1.43(t,3H,J=7.1 Hz), 4.44(q,2H,J=7.2 Hz), 7.17(t,2H,J=8.6 Hz), 7.77(d,1H,J=3.9 Hz), 8.02–8.06(m,2H), 8.23(s,1H),8.80(d,1H,J=4.9 Hz).

Preparation Example 51

Synthesis of 2-(4-fluorophenyl)-4-hydroxymethylpyridine

Ethyl 2-(4-fluorophenyl)isonicotinate (226 mg) was treated in the same manner as in Preparation Example 2 to obtain the title compound.

Yield: 181 mg (97%).

$^1$H-NMR (400 MHz, CDCl$_3$) δ: 4.60(s,2H), 6.99–7.06(m, 3H), 7.50(s,1H), 7.76(dd,2H,J=8.9 Hz,5.3 Hz), 8.40(d,1H, J=5.1 Hz).

Preparation Example 52

Synthesis of 4-chloromethyl-2-(4-fluorophenyl)pyridine 2-(4-Fluorophenyl)-4-hydroxymethylpyridine (181 mg) was treated in the same manner as in Preparation Example 3 to obtain the title compound.

Yield: 184 mg (93%).

$^1$H-NMR (400 MHz, CDCl$_3$) δ: 4.58(s,2H), 7.12–7.18(m, 2H), 7.23(dd,1H,J=4.9 Hz,1.6 Hz), 7.68(s,1H), 7.95–8.00 (m,2H), 8.65(d,1H,J=5.1 Hz).

EXAMPLE 30

Synthesis of N-[[2-(4-fluorophenyl)pyridin-4-yl]methyl]-N'-[[2-(3,4,5-trimethoxyphenyl)pyridin-4-yl]methyl]-piperazine dimaleate

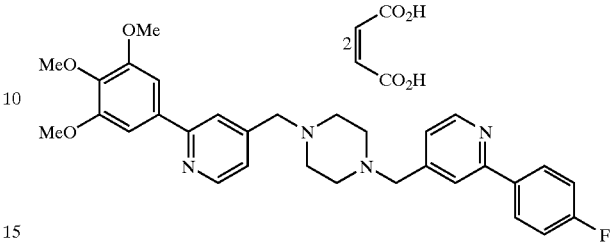

1-[[2-(3,4,5-Trimethoxyphenyl)pyridin-4-yl]-methyl]piperazine (285 mg) and 4-chloromethyl-2-(4-fluorophenyl)pyridine (183 mg) were reacted in the same manner as in Example 1 to produce a maleate, thereby obtaining the title compound.

Yield: 466 mg (74%).

$^1$H-NMR (measured as a maleate, 400 MHz, DMSO-d$_6$) δ: 2.86(br,8H), 3.78(s,3H), 3.89(s,6H), 3.89(s,2H), 3.91(s, 2H), 6.16(s,4H), 7.24–7.29(m,2H), 7.31–7.33(m,2H), 7.36 (s,2H), 7.85(s,2H),8.07–8.11(m,2H), 8.62(d,1H,J=4.9 Hz), 8.63(d,1H,J=4.9 Hz).

m/z (EI): 528 [M$^+$].

Preparation Example 53

Synthesis of ethyl 2-(4-chlorophenyl)isonicotinate

4-Chlorophenylboronic acid (185 mg) and ethyl 2-chloroisonicotinate (200 mg) were reacted in the same manner as in Preparation Example 1 to obtain the title compound.

Yield: 227 mg (81%).

$^1$H-NMR (400 MHz, CDCl$_3$) δ: 1.43(t,3H,J=7.1 Hz), 4.44(q,2H,J=7.1 Hz), 7.44(dd,2H,J=7.2 Hz,1.7 Hz), 7.77(dd, 1H,J=5.1 Hz,1.4 Hz), 7.98(dd,2H,J=6.7 Hz,1.7 Hz), 8.23(s, 1H), 8.79(d,1H,J=4.9 Hz).

Preparation Example 54

Synthesis of 2-(4-chlorophenyl)-4-hydroxymethylpyridine

Ethyl 2-(4-chlorophenyl)isonicotinate (255 mg) was treated in the same manner as in Preparation Example 2 to obtain the title compound.

Yield: 188 mg (88%).

$^1$H-NMR (400 MHz, CDCl$_3$) δ: 4.67(s,2H), 7.13(d,1H,J= 4.9 Hz), 7.36(d,2H,J=8.4 Hz), 7.58(s,1H), 7.78(d,2H,J=8.6 Hz), 8.48(d, 1H, J=4.9 Hz).

Preparation Example 55

Synthesis of 4-chloromethyl-2-(4-chlorophenyl)pyridine 2-(4-Chlorophenyl)-4-hydroxymethylpyridine (188 mg) was treated in the same manner as in Preparation Example 3 to obtain the title compound.

Yield: 176 mg (87%).

$^1$H-NMR (400 MHz, CDCl$_3$) δ: 4.59(s,2H), 7.25(d,1H,J= 4.9 Hz), 7.44(d,2H,J=8.6 Hz), 7.70(s,1H), 7.94(d,2H,J=8.6 Hz), 8.67(d,1H,J=5.1 Hz).

EXAMPLE 31

Synthesis of N-[[2-(4-chlorophenyl)pyridin-4-yl]methyl]-N'-[[2-(3,4,5-trimethoxyphenyl)pyridin-4-yl]methyl]-piperazine dimaleate

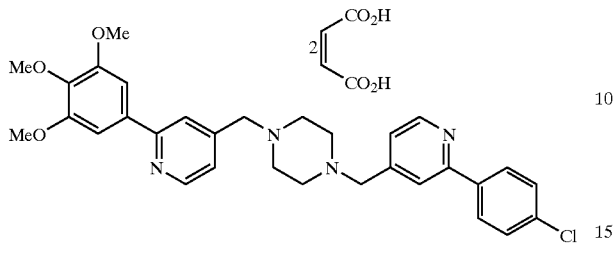

1-[[2-(3,4,5-Trimethoxyphenyl)pyridin-4-yl]-methyl]piperazine (250 mg) and 4-chloromethyl-2-(4-chlorophenyl)pyridine (175 mg) were reacted in the same manner as in Example 1 to produce a maleate, thereby obtaining the title compound.

Yield: 399 mg (70%).

$^1$H-NMR (measured as a maleate, 400 MHz, DMSO-$d_6$) δ: 2.88(br,8H), 3.78(s,3H), 3.89(s,6H), 3.91(s,2H), 3.94(s,2H), 6.16(s,4H), 7.32(d,1H,J=4.9 Hz), 7.35(d,1H,J=4.9 Hz), 7.37(s,2H), 7.51(d,2H,J=8.6 Hz), 7.86(s,1H), 7.88(s,1H), 8.06(d,2H,J=8.6 Hz), 8.62(d,1H,J=5.1 Hz), 8.64(d,1H,J=5.1 Hz).

m/z (EI): 545, 547 [M$^+$].

Preparation Example 56

Synthesis of ethyl 2-(4-trifluoromethylphenyl)-isonicotinate

4-Trifluoromethylphenylboronic acid (255 mg) and ethyl 2-chloroisonicotinate (200 mg) were reacted in the same manner as in Preparation Example 1 to obtain the title compound.

Yield: 215 mg (68%).

$^1$H-NMR (400 MHz, CDCl$_3$) δ: 1.28(br,3H), 4.43(br,2H), 7.63(dd,2H,J=8.5 Hz,3.0 Hz), 7.71–7.73(m,1H), 8.06(br,2H), 8.21(dd,1H,J=2.6 Hz,1.6 Hz), 8.74(dt,1H,J=5.0 Hz,0.9 Hz).

Preparation Example 57

Synthesis of 4-hydroxymethyl-2-(4-trifluoromethylphenyl)-pyridine

Ethyl 2-(4-trifluoromethylphenyl)isonicotinate (215 mg) was treated in the same manner as in Preparation Example 2 to obtain the title compound.

Yield: 170 mg (92%).

$^1$H-NMR (400 MHz, CDCl$_3$) δ: 4.74(s,2H), 7.22(d,1H,J=5.1 Hz), 7.69(d,2H,J=7.6 Hz), 7.70(s,1H), 8.01(d,2H,J=8.4 Hz), 8.56(d,1H,J=5.1 Hz).

Preparation Example 58

Synthesis of 4-chloromethyl-2-(4-trifluoromethylphenyl)-pyridine

4-Hydroxymethyl 2-(4-trifluoromethylphenyl)-pyridine (170 mg) was treated in the same manner as in Preparation Example 3 to obtain the title compound.

Yield: 175 mg (96%).

EXAMPLE 32

Synthesis of N-[[2-(4-trifluoromethylphenyl)pyridin-4-yl]methyl]-N'-[[2-(3,4,5-trimethoxyphenyl)pyridin-4-yl]methyl]piperazine dimaleate

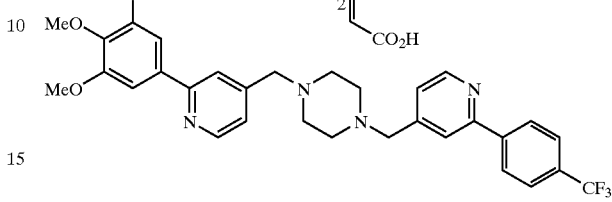

1-[[2-(3,4,5-Trimethoxyphenyl)pyridin-4-yl]-methyl]piperazine (203 mg) and 4-chloromethyl-2-(4-trifluoromethylphenyl)pyridine (159 mg) were reacted in the same manner as in Example 1 to produce a maleate, thereby obtaining the title compound.

Yield: 359 mg (75%).

$^1$H-NMR (measured as a maleate, 400 MHz, DMSO-$d_6$) δ: 2.82–2.88(m,8H), 3.78(s,4H), 3.89(s,6H), 3.92(s,3H), 6.16(s,4H), 7.31(d,1H,J=5.1 Hz), 7.36(s,2H), 7.40(d,1H,J=5.1 Hz), 7.82(d,2H,J=8.2 Hz), 7.84(s,1H), 7.95(s,1H), 8.26 (d,2H,J=8.2 Hz), 8.62(d,1H,J=5.1 Hz), 8.69(d,1H,J=5.1 Hz).

m/z (EI): 578 [M$^+$].

Preparation Example 59

Synthesis of ethyl 2-(4-biphenyl)isonicotinate

4-Biphenylboronic acid (3.50 g) and ethyl 2-chloroisonicotinate (3.15 g) were reacted in the same manner as in Preparation Example 1 to obtain the title compound.

Yield: 4.30 g (84%).

Preparation Example 60

Synthesis of 2-(4-biphenyl)-4-hydroxymethylpyridine

Ethyl 2-(4-biphenyl)isonicotinate (4.30 g) was treated in the same manner as in Preparation Example 2 to obtain the title compound.

Yield: 2.70 g (72%).

Preparation Example 61

Synthesis of 2-(4-biphenyl)-4-chloromethylpyridine 2-(4-Biphenyl)-4-hydroxymethylpyridine (2.70 g) was treated in the same manner as in Preparation Example 3 to obtain the title compound.

Yield: 2.00 g (76%).

EXAMPLE 33

Synthesis of N-[[2-(4-biphenyl)pyridin-4-yl]methyl]-N'-[[2-(3,4,5-trimethoxyphenyl)pyridin-4-yl]methyl]-piperazine

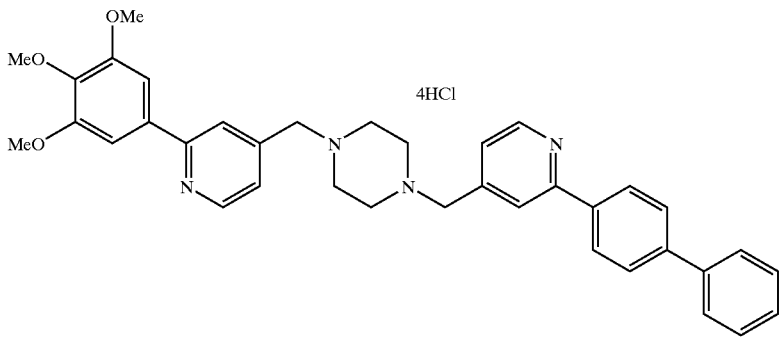

1-[(2-(3,4,5-Trimethoxyphenyl)pyridin-4-yl)-methyl]piperazine (69 mg) and 2-(4-biphenyl)-4-chloromethylpyridine (56 mg) were reacted in the same manner as in Example 1 to obtain the title compound as a free base.

Yield: 75 mg (42%).

$^1$H-NMR (400 MHz, CDCl$_3$) δ: 2.32–2.87(m,8H), 3.50–3.75(m,4H), 3.90(s,3H), 3.96(s,6H), 7.18–7.30(m,5H), 7.31–7.47(m,3H), 7.63–7.81(m,5H), 8.07(d,2H,J=8.4 Hz), 8.10(m,2H).

m/z (EI): 586 [M$^+$].

Preparation Example 62

Synthesis of ethyl 2-(2-naphthyl)isonicotinate

2-Naphthylboronic acid (3.50 g) and ethyl 2-chloroisonicotinate (3.77 g) were reacted in the same manner as in Preparation Example 1 to obtain the title compound.

Yield: 5.00 g (88%).

Preparation Example 63

Synthesis of 4-hydroxymethyl-2-(2-naphthyl)pyridine

Ethyl 2-(2-naphthyl)isonicotinate (5.00 g) was treated in the same manner as in Preparation Example 2 to obtain the title compound.

Yield: 3.30 g (79%).

Preparation Example 64

Synthesis of 4-chloromethyl-2-(2-naphthyl)pyridine

4-Hydroxymethyl-2-(2-naphthyl)pyridine (3.30 g) was treated in the same manner as in Preparation Example 3 to obtain the title compound.

Yield: 3.30 g (92%).

EXAMPLE 34

Synthesis of N-[[2-(2-naphthyl)pyridin-4-yl]methyl]-N'-[[2-(3,4,5-trimethoxyphenyl)pyridin-4-yl]methyl]-piperazine tetrahydrochloride

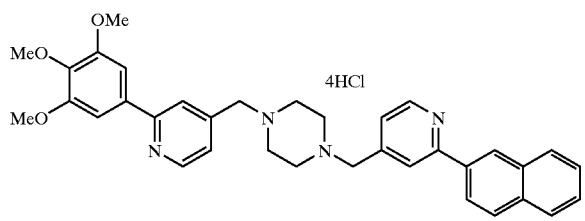

1-[[2-(3,4,5-Trimethoxyphenyl)pyridin-4-yl]-methyl]piperazine (69 mg) and 4-chloromethyl-2-(2-naphthyl)pyridine (56 mg) were reacted in the same manner as in Example 1 to obtain the title compound in the form of a hydrochloride.

Yield: 20 mg (14%).

$^1$H-NMR (measured as a free base, 400 MHz, CDCl$_3$) δ: 2.57(br,8H), 3.59(s,2H), 3.62(s,2H), 3.90(s,3H), 3.97(s,6H), 7.22–7.24(m,4H), 7.45–7.52(m,2H), 7.64(s,1H), 7.86–7.95(m,4H), 8.14(d,1H,J=6.8 Hz), 8.49(s,1H), 8.60(d,1H,J=4.9 Hz), 8.67(d,1H,J=5.1 Hz).

m/z (EI): 560 [M$^+$].

Preparation Example 65

Synthesis of 4-hydroxy-6-methylpyrimidine

4-Hydroxy-2-mercapto-6-methylpyrimidine (3.0 g) was dissolved in a mixed solvent of ethanol (50 mL) and aqueous ammonia (10 mL). Raney nickel (R=100, wet type, 6.0 g) was added to the solution, and the mixture was stirred at 90° C. for 2 hours. The reaction mixture was filtered through celite, and the filtrate was concentrated under reduced pressure. Water was added to the residue to conduct extraction with ethyl acetate. The resultant organic layer was washed with saturated brine and dried over anhydrous sodium sulfate. The resultant crude crystals were recrystallized from chloroform-ether to obtain the title compound.

Yield: 1.20 g (52%).

$^1$H-NMR (400 MHz, CDCl$_3$) δ: 2.30(s,3H), 6.29(s,1H), 8.07(s,1H).

Preparation Example 66

Synthesis of 4-chloro-6-methylpyrimidine

4-Hydroxy-6-methylpyrimidine (782 mg) was dissolved in phosphoryl chloride (6.6 mL), and the solution was stirred for 1 hour at reflux temperature. The reaction mixture was added dropwise to ice water, neutralized with an aqueous solution of 2 M sodium hydroxide and extracted with chloroform. The resultant organic layer was washed with saturated brine, dried over anhydrous sodium sulfate, and concentrated under reduced pressure to obtain the title compound.

Yield: 913 mg (theoretical amount).

Preparation Example 67

Synthesis of 4-methyl-6-(3,4,5-trimethoxyphenyl)-pyrimidine

4-Chloro-6-methylpyrimidine (913 mg) and 3,4,5-trimethoxyphenylboronic acid (2.73 g) were reacted in the same manner as in Preparation Example 1 to obtain the title compound.

Yield: 920 mg (50%).

$^1$H-NMR (400 MHz, CDCl$_3$) δ: 2.51(s,3H), 3.84(s,3H), 3.88(s,6H), 7.25(s,2H), 7.44(d,1H,J=0.6 Hz), 8.02(d,1H,J= 1.2 Hz).

Preparation Example 68

Synthesis of 6-(3,4,5-trimethoxyphenyl)-pyrimidine-4-carboaldehyde

4-Methyl-6-(3,4,5-trimethoxyphenyl)pyrimidine (920 mg) was dissolved in dioxane (100 mL), and to the solution selenium dioxide (784 mg) was added, and the mixture was stirred overnight at 105° C. Water was added to the reaction mixture to conduct extraction with ethyl acetate, and the resultant organic layer was washed with saturated brine, dried over anhydrous sodium sulfate, and then concentrated under reduced pressure. The residue was purified by column chromatography on silica gel (hexane:ethyl acetate=1:1) to obtain the title compound.

Yield: 492 mg (51%).

$^1$H-NMR (400 MHz, CDCl$_3$) δ: 3.95 (s, 3H), 3.99 (s, 6H), 7.44 (s,2H), 8.17(s,1H), 9.43(s,1H), 10.11(s,1H).

Preparation Example 69

Synthesis of 4-hydroxy-6-(3,4,5-trimethoxyphenyl)-pyrimidine 6-(3,4,5-Trimethoxyphenyl)pyrimidine-4-carboaldehyde (364 mg) was dissolved in methanol (50 mL), and to the solution sodium borohydride (25 mg) was added under ice cooling, and the mixture was stirred at room temperature for 2 hours. The reaction mixture was concentrated under reduced pressure, and the residue was purified by column chromatography on silica gel (chloroform:methanol=50:1) to obtain the title compound.

Yield: 339 mg (92%).

$^1$H-NMR (400 MHz, CDCl$_3$) δ: 3.93(s,3H), 3.98(s,6H), 4.84(s,2H), 7.37(s,2H), 7.68(s,1H), 9.18(s,1H).

Preparation Example 70

Synthesis of 4-chloromethyl-6-(3,4,5-trimethoxyphenyl)-pyrimidine

4-Hydroxymethyl-6-(3,4,5-trimethoxyphenyl)-pyrimidine (339 mg) was treated in the same manner as in Preparation Example 3 to obtain the title compound.

Yield: 174 mg (60%).

$^1$H-NMR (400 MHz, CDCl$_3$) δ: 3.86(s,3H), 3.91(s,6H), 4.61(s,2H), 7.30(s,2H), 7.78(s,1H), 9.10(s,1H).

EXAMPLE 35

Synthesis of N-[[2-(3,4,5-trimethoxyphenyl)pyridin-4-yl]methyl]-N'-[[6-(3,4,5-trimethoxyphenyl)pyrimidin-4-yl]methyl]piperazine dimaleate

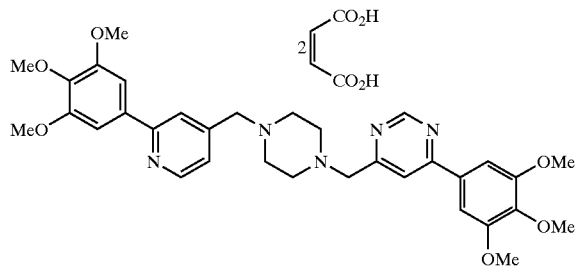

1-[[2-(3,4,5-Trimethoxyphenyl)pyridin-4-yl]-methyl] piperazine (113 mg) and 4-chloromethyl-6-(3,4,5-trimethoxyphenyl)pyrimidine (126 mg) were reacted in the same manner as in Example 1 to obtain the title compound in the form of a maleate.

Yield: 20 mg (14%).

$^1$H-NMR (measured as a free base, 400 MHZ,CDCl$_3$) δ: 2.50–2.75(m,8H), 3.61(s,2H), 3.72(s,2H), 3.91(s,3H), 3.93 (s,3H), 3.97(s,6H), 3.98(s,6H), 7.22–7.24(m,3H), 7.36(s, 2H), 7.65(s,1H), 7.78(s,1H), 8.60(d,1H,J=5.1 Hz), 9.17(s, 1H).

m/z (EI): 601 [M$^+$].

Preparation Example 71

Synthesis of 5,6,7-trimethoxynaphthalene-2-carbonitrile 2.0 M Lithium diisopropylamide (2.55 mL) was added to dry THF (5 mL) at −75° C. under an argon atmosphere, and a solution of 3-cyanopropionaldehyde dimethylacetal (672 mg) in dry THF (5 mL) was then added dropwise to the mixture, and the resulting mixture was stirred at −75° C. for 1 hour. A solution of 3,4,5-trimethoxy-benzaldehyde (1.0 g) in dry THF (5 mL) was then added dropwise to the reaction mixture. After the mixture was warmed to room temperature and stirred for 1 hour, a saturated aqueous solution of ammonium chloride was added to the reaction mixture to conduct extraction with ethyl acetate. The resultant organic layer was washed with saturated brine, dried over anhydrous magnesium sulfate and then concentrated under reduced pressure. The resultant residue was dissolved in methanol (6 mL), sulfuric acid (1 mL) was slowly added to the solution, and the mixture was stirred at 100° C. for 1 hour. The reaction mixture was weakly alkalified with an aqueous solution of 4 M potassium hydroxide at 0° C. to conduct extraction with chloroform. The resultant organic layer was washed with water and saturated brine, dried over anhydrous magnesium sulfate and then concentrated under reduced pressure. The residue was purified by column chromatography on silica gel (ethyl acetate:hexane=1:3 to 1:1) to obtain the title compound.

Yield: 847 mg (68%).

Preparation Example 72

Synthesis of 5,6,7-trimethoxynaphthalene-2-carboxylic acid 5,6,7-Trimethoxynaphthalene-2-carbonitrile (5.8 g) obtained above was dissolved in ethanol (40 mL), an aqueous solution (10 mL) of potassium hydroxide (11.2 g) was added to the solution, and the mixture was stirred for 1 hour under reflux. After cooling, the solvent was distilled off, the residue was dissolved in water, and the solution was washed with ether. The resultant water layer was then neutralized with diluted hydrochloric acid and then extracted with ethyl acetate. The resultant organic layer was washed with saturated brine and water dried over anhydrous magnesium sulfate and then concentrated under reduced pressure to obtain the title compound.

Yield: 5.2 g (85%).

$^1$H-NMR (400 MHz, CDCl$_3$) δ ppm: 4.00(s,3H), 4.02(s, 3H), 4.06(s,3H), 7.08(s,1H), 8.00(dd,1H,J=8.8 Hz,1.7 Hz), 8.12(d,1H,J=8.8 Hz), 8.55(d,1H,J=1.5 Hz).

Preparation Example 73

Synthesis of 2-hydroxymethyl-5,6,7-trimethoxynaphthalene

Lithium aluminum hydride (579 mg) was added to dry THF (40 mL) under an argon atmosphere and ice cooling, a solution of 5,6,7-trimethoxynaphthalene-2-carboxylic acid (4.0 g) in dry THF (40 mL) was then added dropwise thereto, and the mixture was stirred at room temperature for 4 hours. Ether (150 mL) was added to the reaction mixture, sodium sulfate decahydrate was added thereto, and the resultant mixture was stirred for 15 minutes. The reaction mixture was filtered, the filtrate was concentrated, and the residue was purified by column chromatography on silica gel (ethyl acetate:hexane=1:2) to obtain the title compound.

Yield: 3.8 g (theoretical amount).

$^1$H-NMR (400 MHz, CDCl$_3$) δ ppm: 3.97(s,6H), 4.04(s, 3H), 4.82(d,2H,J=5.6 Hz), 6.93(s,1H), 7.35(dd,1H,J=8.6 Hz,1.7 Hz), 7.66(s,1H), 8.03(d, 1H, J=8.6 Hz).

Preparation Example 74

Synthesis of 5,6,7-trimethoxynaphthalene-2-carboaldehyde

2-Hydroxymethyl-5,6,7-trimethoxynaphthalene (3.78 g) was dissolved in dichloromethane (100 mL), pyridinium dichromate (8. 61 g) was added to the solution, and the mixture was stirred at room temperature for 4 hours. The reaction mixture was filtered, and insoluble matter was washed with chloroform. After the filtrate was concentrated under reduced pressure, the residue was diluted with ethyl acetate, washed with 2 M hydrochloric acid, water and saturated brine, dried over anhydrous magnesium sulfate and then concentrated under reduced pressure. The residue was purified by column chromatography on silica gel (ethyl acetate:hexane=1:3 to 1:1) and further recrystallized from ethyl acetate-hexane to obtain the title compound.

Yield: 3.24 g (86%).

$^1$H-NMR (400 MHz, CDCl$_3$) δ ppm: 4.01(s,3H), 4.02(s, 3H), 4.05(s,3H), 7.10(s,1H), 7.82(dd,1H,J=8.7 Hz,1.6 Hz), 8.15(d,1H,J=8.7 Hz), 8.19(d,1H,J=1.5 Hz), 10.11(s,1H).

Preparation Example 75

Synthesis of ethyl 3-(5,6,7-trimethoxynaphthalen-2-yl)propenoate 5,6,7-Trimethoxynaphthalene-2-carboaldehyde (1.23 g) was treated in the same manner as in Preparation Example 8 to obtain the title compound.

Yield: 1.79 g (theoretical amount).

$^1$H-NMR (400 MHz, CDCl$_3$) δ ppm: 1.35(t,3H,J=7.1 Hz), 3.98(s,6H), 4.04(s,3H), 4.24(q,2H,J=7.1 Hz), 6.53(d,1H,J=16.1 Hz), 6.96(s,1H), 7.55(d,1H,J=8.8 Hz), 7.78(s,1H), 7.80 (d,1H,J=16.1 Hz), 8.03(d,1H,J=8.8 Hz).

Preparation Example 76

Synthesis of ethyl 3-(5,6,7-trimethoxynaphthalen-2-yl)propionate

Ethyl 3-(5,6,7-trimethoxynaphthalen-2-yl)propenoate (1.70 g) was treated in the same manner as in Preparation Example 6 to obtain the title compound.

Yield: 1.28 g (81%).

$^1$H-NMR (400 MHz, CDCl$_3$) δ ppm: 1.23(t,3H,J=7.2 Hz), 2.68(t,2H,J=7.8 Hz), 3.07(t,2H,J=7.8 Hz), 3.95(s,3H), 3.96 (s,3H), 4.03(s,3H), 4.13(q,2H,J=7.1 Hz), 6.89(s,1H), 7.21 (dd,1H,J=8.6 Hz,1.6 Hz), 7.50(s,1H), 7.96(d,1H,J=8.5 Hz).

Preparation Example 77

Synthesis of 2-(3-hydroxypropyl)-5,6,7-trimethoxynaphthalene

Ethyl 3-(5,6,7-trimethoxynaphthalen-2-yl)propionate (1.28 g) was treated in the same manner as in Preparation Example 2 to obtain the title compound.

Yield: 1.13 g (theoretical amount).

$^1$H-NMR (400 MHz, CDCl$_3$) δ ppm: 1.55(s,1H), 1.97(m, 2H), 2.84(t,2H,J=7.6 Hz), 3.71(dd,2H,J=2.0 Hz,6.3 Hz), 3.96(s,3H), 3.97(s,3H), 4.04(s,3H), 6.89(s,1H), 7.22(dd,1H, J=8.6 Hz,1.7 Hz), 7.49(s,1H), 7.96(d,1H,J=8.5 Hz).

Preparation Example 78

Synthesis of 2-(3-methanesulfonyloxypropyl)-5,6,7-trimethoxynaphthalene 2-(3-Hydroxypropyl)-5,6,7-trimethoxynaphthalene (1.26 g) was treated in the same manner as in Preparation Example 7 to obtain the title compound.

Yield: 1.55 g (95%).

$^1$H-NMR (400 MHz, CDCl$_3$) δ ppm: 2.16(quint,2H,J=7.8 Hz), 2.90(t,2H,J=7.8 Hz), 3.00(s,3H), 3.97(s,6H), 4.05(s, 3H), 4.25(t,3H,J=7.8 Hz), 6.93(s,1H), 7.24(dd,1H,J=8.4 Hz,1.7 Hz), 7.63(d,1H,J=8.4 Hz), 7.83(d,1H,J=1.7 Hz).

EXAMPLE 36

Synthesis of N-[[3-(5,6,7-trimethoxynaphthalen-2-yl)propyl]-N'-[[2-(3,4,5-trimethoxyphenyl)pyridin-4-yl]methyl]piperazine dimaleate

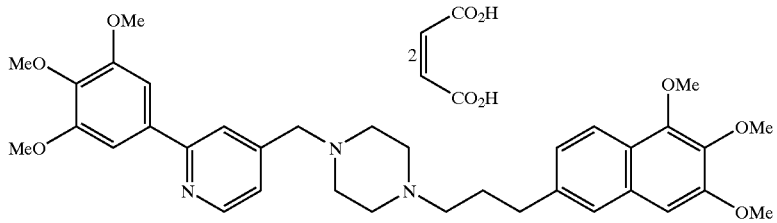

1-[[2-(3,4,5-Trimethoxyphenyl)pyridin-4-yl]-methyl] piperazine (113 mg) and 2-(3-methanesulfonyloxy-propyl)-5,6,7-trimethoxynaphthalene (117 mg) were reacted in the same manner as in Example 1 to obtain the title compound in the form of a maleate.

Yield: 145 mg (53%).

$^1$H-NMR (measured as a free base, 400 MHz, CDCl$_3$) δ: 1.88(quint,2H,J=7.8 Hz), 2.40(t,2H,J=7.8 Hz), 2.51(br,8H), 2.74(t,2H,J=7.8 Hz), 3.46(s,3H), 3.55(s,2H), 3.88(s,3H), 3.93(s,3H), 3.95(s,6H), 4.01(s,3H), 6.86(s,1H), 7.15–7.20 (m,2H), 7.21(s,2H), 7.44(s,1H), 7.61(s,1H), 7.92(d,1H,J= 8.6 Hz), 8.56(d,1H,J=3.1 Hz).

m/z (EI): 601 [M$^+$].

Preparation Example 79

Synthesis of 5,6,7-trimethoxy-2-vinylnaphthalene

Methyltriphenylphosphonium bromide (2.8 g) was suspended in dry THF (10 mL) under an argon atmosphere, and a hexane solution (3.3 mL) of 1.7 M tert-butyllithium was added to the suspension at −20° C. After the reaction mixture was warmed to room temperature and stirred for 1 hour, it was cooled again to −20° C., a solution of 5,6,7-trimethoxynaphthalene-2-carboaldehyde (1.26 g) in dry THF (30 mL) was added dropwise thereto, and the mixture was stirred overnight at room temperature. The solvent was distilled off, and water was added to the residue to conduct extraction with ethyl acetate. The resultant organic layer was washed with water and saturated brine, dried over anhydrous magnesium sulfate and then concentrated under reduced pressure. The residue was purified by column chromatography on silica gel (ethyl acetate:hexane=1:8) to obtain the title compound.

Yield: 1.15 g (93%).

$^1$H-NMR (400 MHz, CDCl$_3$) δ ppm: 3.93(s,3H), 3.98(s,3H), 4.04(s,3H), 5.31(d,1H,J=10.9 Hz), 5.85(d,1H,J=17.6 Hz), 6.83(dd,1H,J=17.5 Hz,10.7 Hz), 6.90(s,1H), 7.51(dd, 1H,J=8.7 Hz,1.7 Hz), 7.59(s,1H), 8.01(d,1H,J=8.6 Hz).

Preparation Example 80

Synthesis of 2-(2-hydroxyethyl)-5,6,7-trimethoxynaphthalene 5,6,7-Trimethoxy-2-vinylnaphthalene (1.215 g) was dissolved in dry THF (10 mL) under an argon atmosphere, a THF solution (4.7 mL) of 1 M borane was added dropwise to the solution at 0° C., and the mixture was stirred at room temperature for 2 hours. Water (4 mL) was added to the reaction mixture at 0° C., and an aqueous solution (1.2 mL) of 4 M sodium hydroxide was then added. 31% Aqueous hydrogen peroxide (0.5 mL) was added to the reaction mixture at 0° C., and the mixture was stirred at 50° C. for 50 minutes. The reaction mixture was concentrated under reduced pressure, and water was added to the residue to conduct extraction with ethyl acetate. The resultant organic layer was washed with water and saturated brine, dried over anhydrous magnesium sulfate and then concentrated under reduced pressure. The residue was purified by column chromatography on silica gel (ethyl acetate:hexane=1:8) to obtain the title compound.

Yield: 1.03 g (84%).

$^1$H-NMR (400 MHz, CDCl$_3$) δ ppm: 2.02(br,1H), 2.95 (d,2H,J=6.6 Hz), 3.87(t,2H,J=6.6 Hz), 3.93(s,3H), 3.95(s, 3H), 4.02(s,3H), 6.88(s,1H), 7.20(dd,1H,J=8.5 Hz,1.7 Hz), 7.50(s,1H), 7.97(d,1H,J=8.6 Hz).

Preparation Example 81

Synthesis of 2-(2-methanesulfonyloxyethyl)-5,6,7-trimethoxynaphthalene 2-(2-Hydroxyethyl)-5,6,7-trimethoxynaphthalene (1.26 g) was treated in the same manner as in Preparation Example 7 to obtain the title compound.

Yield: 1.55 g (95%).

$^1$H-NMR (400 MHz, CDCl$_3$) δ ppm: 2.84(s,3H), 3.18(t, 2H,J=6.9 Hz), 3.96(s,3H), 3.97(s,3H), 4.04(s,3H), 4.49(t, 2H,J=6.9 Hz), 6.90(s,1H), 7.22(dd,1H,J=9.4 Hz,1.2 Hz), 7.54(s,1H), 8.00(d,1H,J=8.6 Hz).

EXAMPLE 37

Synthesis of N-[2-(5,6,7-trimethoxynaphthalen-2-yl) ethyl]-N'-[[2-(3,4,5-trimethoxyphenyl)pyridin-4-yl] methyl]-piperazine dimaleate

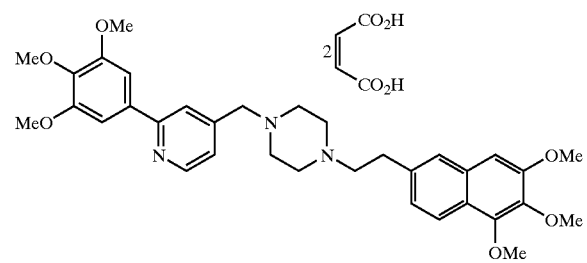

1-[[2-(3,4,5-Trimethoxyphenyl)pyridin-4-yl]-methyl] piperazine (290 mg) and 2-(2-methanesulfonyloxy-ethyl)-5,6,7-trimethoxynaphthalene (218 mg) were reacted in the same manner as in Example 1 to obtain the title compound in the form of a maleate.

Yield: 131 mg (25%).

$^1$H-NMR (measured as a maleate, 400 MHz, DMSO-d$_6$) δ: 2.79(t,4H,J=4.9 Hz), 3.07–3.11(m,2H), 3.23(t,4H,J=4.9 Hz), 3.29–3.33(m,2H), 3.76(s,2H), 3.79(s,3H), 3.88(s,3H), 3.90(s,6H), 3.93(s,3H), 3.98(s,3H), 6.12(s,4H), 7.04(s,1H), 7.25(dd,1H,J=8.5 Hz,1.7 Hz), 7.28(dd,1H,J=5.9 Hz,1.0 Hz), 7.36(s,2H), 7.61(s,1H), 7.79(s,1H), 7.91(d,1H,J=4.2 Hz), 8.59(d,1H,J=4.7 Hz).

m/z (EI): 587 [M$^+$].

Preparation Example 82

Synthesis of 2-chloromethyl-5,6,7-trimethoxynaphthalene

2-Hydroxymethyl-5,6,7-trimethoxynaphthalene (781 mg) was treated in the same manner as in Preparation Example 3 to obtain the title compound.

Yield: 608 mg (73%).

$^1$H-NMR (400 MHz, CDCl$_3$) δ ppm: 3.96(s,3H), 3.97(s, 3H), 4.03(s,3H), 4.71(s,2H), 6.29(s,1H), 7.36(dd,1H,J=8.6 Hz,1.5 Hz), 7.67(s,1H), 8.04(d,1H,J=8.7 Hz).

EXAMPLE 38

Synthesis of N-[(5,6,7-trimethoxynaphthalen-2-yl)methyl]-N'-[[2-(3,4,5-trimethoxyphenyl)pyridin-4-yl]methyl]-piperazine dimaleate

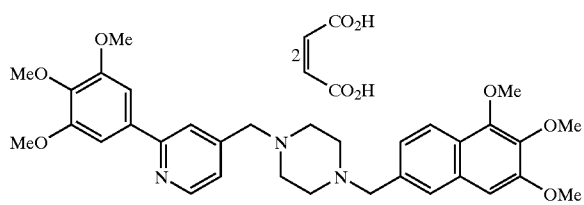

1-[[2-(3,4,5-Trimethoxyphenyl)pyridin-4-yl]-methyl] piperazine (529 mg) and 2-chloromethyl-5,6,7-trimethoxynaphthalene (411 mg) were reacted in the same manner as in Example 1 to obtain the title compound in the form of a maleate.

Yield: 198 mg (16%). $^1$H-NMR (measured as a free base, 400 MHz, CDCl$_3$) δ: 2.52(br,8H), 3.55(s,2H), 3.63(s,2H), 3.88(s,3H), 3.94(s,6H), 3.95(s,6H), 4.02(s,3H), 6.90(s,1H), 7.18(d,1H,J=5.7 Hz), 7.21(s,2H), 7.32(dd,1H,J=8.6 Hz,1.6 Hz), 7.57(s,1H), 7.60(s,1H), 7.96(d,1H,J=8.6 Hz), 8.56(d,1H,J=5.7 Hz).

m/z (EI): 587 [M$^+$].

Preparation Example 83

Synthesis of (E)-5-bromo-1-phenyl-1-pentene

Metal sodium (303 mg) was added to dry 2-propanol (30 mL), and the mixture was stirred at 70° C. After the sodium was dissolved, benzaldehyde (1.0 g) was added to the solution at 0° C., 4-bromobutyltriphenylphosphonium bromide (5.4 g) was then added, and the mixture was gradually warmed to room temperature. After 5 hours, the reaction mixture was concentrated under reduced pressure, ethyl acetate was added to the residue, and the resultant mixture was washed with water and saturated brine, dried over anhydrous sodium sulfate and concentrated under reduced pressure. The residue was then purified by column chromatography on silica gel (hexane) to obtain the title compound.

Yield: 806 mg (38%).

$^1$H-NMR (400 MHz, CDCl$_3$) δ: 1.96–2.02(m,2H), 2.34–2.46(m,2H), 3.41(t,2H,J=6.7 Hz), 6.12(dd,1H,J=17.4 Hz,6.8 Hz), 6.42(d,1H,J=16.0 Hz), 7.18–7.33(m,5H).

EXAMPLE 39

Synthesis of N-[(E)-5-phenyl-4-pentenyl]-N'-[[2-(3,4,5-trimethoxyphenyl)pyridin-4-yl]methyl] piperazine difumarate

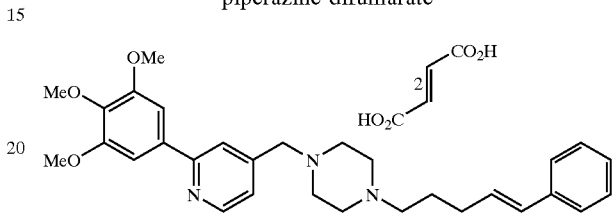

1-[[2-(3,4,5-Trimethoxyphenyl)pyridin-4-yl]-methyl] piperazine (226 mg) and (E)-5-bromo-1-phenyl-1-pentene (113 mg) were reacted in the same manner as in Example 1 to obtain the title compound in the form of a fumarate.

Yield: 150 mg (42%).

$^1$H-NMR (measured as a fumarate, 400 MHz, DMSO-d$_6$) δ: 1.59–1.61(m,2H), 2.18–2.24(m,2H), 2.28–2.51(m,10H), 3.58(s,2H), 3.77(s,3H), 3.83(s,6H), 6.19–6.28(m,1H), 6.39 (d,1H,J=15.6 Hz), 6.62(s,4H), 7.14–7.34(m,6H), 7.34(s, 2H), 7.74(s,1H), 8.53(d,1H,J=5.1 Hz).

m/z (EI): 487 [M$^+$].

Preparation Example 84

Synthesis of (E)-5-bromo-1-(3,4,5-trimethoxyphenyl)-1-pentene 3,4,5-Trimethoxybenzaldehyde (9.81 g) and 4-bromobutyltriphenylphosphonium bromide (23.93 g) were treated in the same manner as in Preparation Example 83 to obtain the title compound.

Yield: 5.10 g (32%).

EXAMPLE 40

Synthesis of N-[(E)-5-(3,4,5-trimethoxyphenyl)-4-pentenyl-]-N'-[[2-(3,4,5-trimethoxyphenyl)pyridin-4-yl]methyl]piperazine difumarate

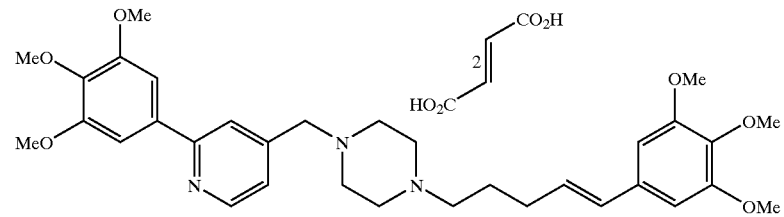

1-[[2-(3,4,5-Trimethoxyphenyl)pyridin-4-yl]-methyl] piperazine (151 mg) and (E)-5-bromo-1-(3,4,5-trimethoxyphenyl)-1-pentene (114 mg) were reacted in the same manner as in Example 1 to obtain the title compound in the form of a fumarate.

Yield: 106 mg (36%).

$^1$H-NMR (measured as a fumarate, 400 MHz, DMSO-$d_6$) δ: 1.62–1.67(m,2H), 2.17–2.22(m,2H), 2.43–2.47(m,2H), 2.51–2.56(m,8H), 3.40(s,3H), 3.70(s,3H), 3.78(s,2H), 3.79 (s,6H), 3.88(s,6H), 6.16(dt,1H,J=15.8 Hz,6.6 Hz), 6.31(d, 1H,J=15.8 Hz), 6.62(s,2H), 6.63(s,4H), 7.22(d,1H,J=4.9 Hz), 7.34(s,2H), 7.73(s,1H), 8.53(d,1H,J=5.1 Hz).

m/z (EI): 577

Preparation Example 85

Synthesis of 1-[(E)-5-(3,4,5-trimethoxyphenyl)-4-pentenyl]homopiperazine (E)-5-Bromo-1-(3,4,5-trimethoxyphenyl)-1-pentene (434 mg) and homopiperazine (276 mg) were reacted in the same manner as in Preparation Example 4 to obtain the title compound.

Yield: 279 mg (60%).

$^1$H-NMR (400 MHz, CDCl$_3$) δ: 1.62–1.70(m,2H), 1.74–1.80(m,2H), 2.20–2.25(m,2H), 2.53–2.56(m,2H), 2.66–2.72(m,4H), 2.90–2.95(m,4H), 3.84(s,3H), 3.87(s,6H), 6.14(dt,1H,J=15.6 Hz,6.8 Hz), 6.32(d,1H,J=15.6 Hz), 6.57 (s,2H).

EXAMPLE 41

Synthesis of N-[(E)-5-(3,4,5-trimethoxyphenyl)-4-pentenyl]-N'-[[2-(3,4,5-trimethoxyphenyl)pyridin-4-yl]methyl]homopiperazine difumarate

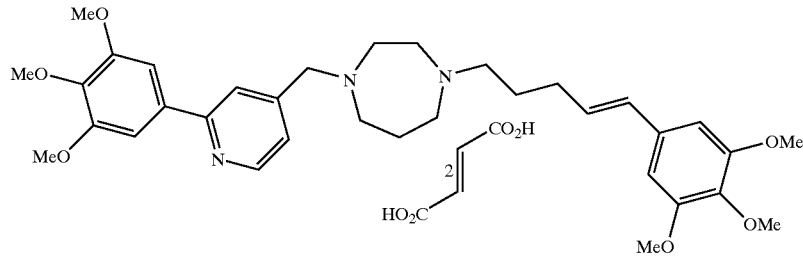

1-[(E)-5-(3,4,5-trimethoxyphenyl)-4-pentenyl]-homopiperazine (279 mg) and 4-chloromethyl-2-(3,4,5-trimethoxyphenyl)pyridine (24 mg) were reacted in the same manner as in Example 1 to obtain the title compound in the form of a fumarate.

Yield: 267 mg (39%).

$^1$H-NMR (measured as a fumarate, 400 MHz, DMSO-$d_6$) δ: 1.63–1.70(m,2H), 1.80–1.86(m,2H), 2.19–2.24(m,2H), 2.65–2.69(m,2H), 2.75–2.79(m,4H), 2.83–2.89(m,4H), 3.70 (s,2H), 3.75(s,3H), 3.78(s,3H), 3.79(s,6H), 3.89(s,6H), 6.16 (dt,1H,J=15.9 Hz,6.6 Hz), 6.32(d,1H,J=15.9 Hz), 6.59(s, 6H), 7.24(d,1H,J=3.7 Hz), 7.34(s,2H), 7.76(s,1H), 8.53(d, 1H,J=4.9 Hz).

m/z (EI): 591

Preparation Example 86

Synthesis of (E)-5-bromo-1-(4-fluorophenyl)-1-pentene

4-Fluorobenzaldehyde (1.0 g) and 4-bromobutyl-triphenylphosphonium bromide (4.62 g) were treated in the same manner as in Preparation Example 83 to obtain the title compound.

Yield: 811 mg (41%).

$^1$H-NMR (400 MHz, CDCl$_3$) δ: 1.98–2.06(m,2H), 2.34–2.45(m,2H), 3.45(t,2H,J=6.7 Hz), 6.07(dt,1H,J=15.8 Hz,7.0 Hz), 6.40(d,1H,J=15.9 Hz), 6.96–7.31(m,4H).

EXAMPLE 42

Synthesis of N-[(E)-5-(4-fluorophenyl)-4-pentenyl]-N'-[[2-(3,4,5-trimethoxyphenyl)pyridin-4-yl]methyl] piperazine difumarate

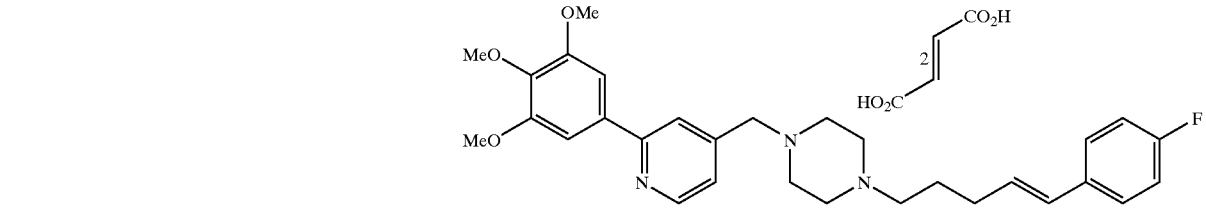

1-[[2-(3,4,5-Trimethoxyphenyl)pyridin-4-yl]-methyl] piperazine (226 mg) and (E)-5-bromo-1-(4-fluorophenyl)-

1-pentene (122 mg) were reacted in the same manner as in Example 1 to obtain the title compound in the form of a fumarate.

Yield: 76 mg (21%).

$^1$H-NMR (measured as a fumarate, 400 MHz, DMSO-$d_6$) δ: 1.54–1.66(m,2H), 2.17–2.23(m,2H), 2.40–2.53(m,10H), 3.60(s,2H), 3.77(s,3H), 3.88(s,6H), 6.14–6.22(m,1H), 6.36–6.40(m,1H), 6.63(s,4H), 7.00–7.08(m,2H), 7.23(d,1H, J=4.9 Hz), 7.34(s,2H), 7.31–7.37(m,2H), 7.74(s,1H), 8.53 (d,1H,J=4.9 Hz).

m/z (EI) : 505 [M$^+$].

Preparation Example 87

Synthesis of (E)-5-bromo-1-(4-chlorophenyl)-1-pentene

4-Chlorobenzaldehyde (1.0 g) and 4-bromobutyl-triphenylphosphonium bromide (4.08 g) were treated in the same manner as in Preparation Example 83 to obtain the title compound.

Yield: 401 mg (22%).

$^1$H-NMR (400 MHz, CDCl$_3$) δ: 1.92–2.03(m,2H), 2.32–2.45(m,2H), 3.42(t,2H,J=6.7 Hz), 6.11(dt,1H,J=15.8 Hz,7.0 Hz), 6.37(d,1H,J=15.9 Hz), 7.16–7.29(m,4H).

EXAMPLE 43

Synthesis of N-[(E)-5-(4-chlorophenyl)-4-pentenyl]-N'-[[2-(3,4,5-trimethoxyphenyl)pyridin-4-yl]methyl] piperazine difumarate

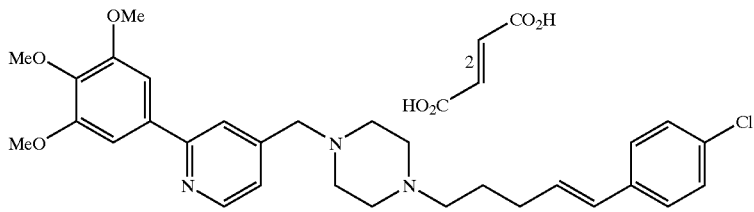

1-[[2-(3,4,5-Trimethoxyphenyl)pyridin-4-yl]-methyl] piperazine (480 mg) and (E)-5-bromo-1-(4-chlorophenyl)-1-pentene (364 mg) were reacted in the same manner as in Example 1 to obtain the title compound in the form of a fumarate.

Yield: 144 mg (14%).

$^1$H-NMR (measured as a fumarate, 400 MHz, DMSO-$d_6$) δ: 1.56–1.64(m,2.H), 2.14–2.20(m,2H), 2.40–2.53(m,10H), 3.56(s,2H), 3.74(s,3H), 3.84(s,6H), 6.19–6.26(m,1H), 6.35 (d,1H,J=8.0 Hz), 6.59(s,4H), 7.20(d,1H,J=4.9 Hz), 7.25(d, 2H,J=8.6 Hz), 7.31(s,2H), 7.32(d,2H,J=8.6 Hz), 7.72(s,1H), 8.51(d,1H,J=4.9 Hz).

m/z (EI): 522, 524 [M$^+$].

EXAMPLE 44

Synthesis of N-[(E)-3-(3,4,5-trimethoxyphenyl)-2-propenyl]-N'-[[2-(3,4,5-trimethoxyphenyl)pyridin-4-yl]methyl]piperazine dimaleate

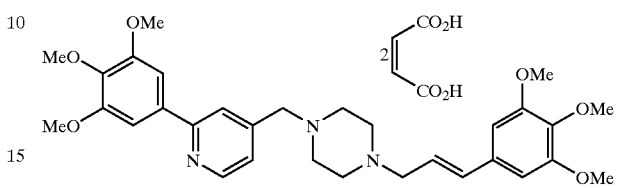

3-(3,4,5-Trimethoxyphenyl)-2-propen-1-ol (50 mg) was dissolved in carbon tetrachloride (5.0 mL), and to the solution triphenylphosphine (75.5 mg) was added, and the mixture was stirred overnight at reflux temperature. The reaction mixture was concentrated under reduced pressure, and the residue was then dissolved in acetonitrile (5.0 ml). To the solution 1-[[2-(3,4,5-trimethoxyphenyl)-pyridin-4-yl]methyl]piperazine (70 mg), potassium iodide (47 mg) and potassium carbonate (55 mg) were added, and the mixture was stirred at room temperature for 3 hours. Water was added to the reaction mixture to conduct extraction with chloroform, and the resultant organic layer was washed with saturated brine, dried over anhydrous sodium sulfate and concentrated under reduced pressure. The residue was purified by column chromatography on silica gel (chloroform:methanol=20:1) to obtain the title compound in the form of a maleate.

Yield: 48 mg (26%).

$^1$H-NMR (measured as a free base, 400 MHz, CDCl$_3$) δ: 2.42–2.78(m,8H), 3.17(d,2H,J=6.6 Hz), 3.59(s,2H), 3.48(s, 3H), 3.86(s,6H), 3.91(s,3H), 3.98(s,6H), 6.10–6.25(m,1H), 6.45(d,1H,J=15.6 Hz), 6.11(s,2H), 7.22–7.24(m,3H), 7.64(s, 1H), 8.60(d,1H,J=4.9 Hz).

m/z (EI): 549 [M$^+$].

EXAMPLE 45

Synthesis of N-[(E)-3-(2,3,4-trimethoxyphenyl)-2-propenyl]-N'-[[2-(3,4,5-trimethoxyphenyl)pyridin-4-yl]methyl]piperazine dimaleate

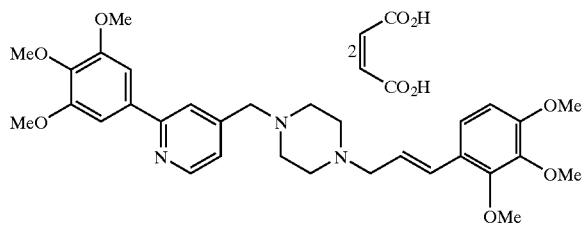

3-(2,3,4-Trimethoxyphenyl)-2-propen-1-ol (122 mg) was treated in the same manner as in Example 44, and 1-[[2-(3,4,5-trimethoxyphenyl)pyridin-4-yl]methyl]piperazine (180 mg) was allowed to react in the same manner as in Example 44 to obtain the title compound in the form of a maleate.

Yield: 17 mg (9%).

$^1$H-NMR (measured as a free base, 400 MHz, CDCl$_3$) δ: 2.45–2.80(m,8H), 3.19(d,2H,J=7.2 Hz), 3.59(s,2H), 3.85(s,3H), 3.86(s,3H), 3.87(s,3H), 3.91(s,3H), 4.00(s,6H), 6.18 (dt,1H,J=16.0 Hz,7.2 Hz), 6.65(d,1H,J=8.8 Hz), 6.73(d,1H, J=15.8 Hz), 7.17(d,1H,J=8.8 Hz), 7.22–7.24(m,3H), 7.64(s,1H), 8.60(d,1H,J=5.1 Hz).

m/z (EI): 549 [M$^+$].

EXAMPLE 46

Synthesis of N-phenylacetyl-N'-[[2-(3,4,5-trimethoxy-phenyl)pyridin-4-yl]methyl]piperazine hydrochloride

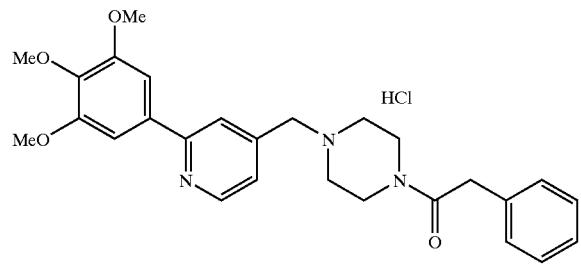

1-[[2-(3,4,5-Trimethoxyphenyl)pyridin-4-yl]methyl]-piperazine (103 mg) was dissolved in dichloromethane (0.9 mL), and to the solution phenylacetyl chloride (60 mg) was added, and the mixture was stirred for 1 hour under ice cooling. A saturated aqueous solution of sodium hydrogencarbonate was added to the reaction mixture to conduct extraction with chloroform. The resultant organic layer was dried over anhydrous sodium sulfate and concentrated under reduced pressure, and the residue was purified by column chromatography on silica gel (chloroform:methanol=50:1) to obtain the title compound in the form of a hydrochloride.

Yield: 10 mg (7%).

$^1$H-NMR (measured as a free base, 400 MHz, CDCl$_3$) δ: 2.28 (br,2H), 2.46(br,2H), 3.47(br,2H), 3.53(s,2H), 3.69(br,2H), 3.74(s,2H), 3.90(s,3H), 3.97(s,6H), 7.18–7.32(m,8H), 7.59(s,1H), 8.59(d,1H,J=5.1 Hz).

m/z (EI): 461 [M$^+$].

EXAMPLE 47

Synthesis of N-(4-methoxyphenyl)acetyl-N'-[[2-(3,4,5-trimethoxyphenyl)pyridin-4-yl]methyl]piperazine hydrochloride

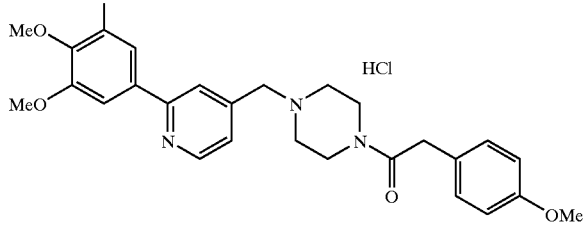

1-[[2-(3,4,5-Trimethoxyphenyl)pyridin-4-yl]methyl]-piperazine (103 mg) and (4-methoxyphenyl)acetyl chloride (60 mg) were reacted in the same manner as in Example 46 to obtain the title compound in the form of a hydrochloride.

Yield: 18 mg (11%).

$^1$H-NMR (measured as a free base, 400 MHz, CDCl$_3$) δ: 2.32 (br, 2H), 2.48(br,2H), 3.48(br,2H), 3.53(s,2H), 3.57(s,2H),3.66–3.72(m,2H), 3.79(s,3H), 3.90(s,3H), 3.96(s,6H), 6.85(d,2H,J=8.4 Hz), 7.14(d,2H,J=8.6 Hz), 7.21–7.25(m,3H), 7.62(s,1H), 8.61(d,1H,J=4.9 Hz).

m/z (EI): 491 [M$^+$].

EXAMPLE 48

Synthesis of N-benzoyl-N'-[[2-(3,4,5-trimethoxyphenyl)-pyridin-4-yl]methyl]piperazine

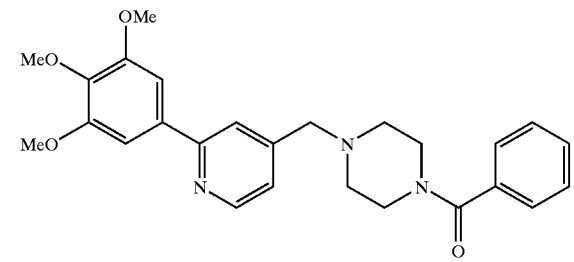

1-[[2-(3,4,5-Trimethoxyphenyl)pyridin-4-yl]methyl]-piperazine (103 mg) and benzoyl chloride (55 mg) were reacted in the same manner as in Example 46 to obtain the title compound as a free base.

Yield: 97 mg (73%).

$^1$H-NMR (400 MHz, CDCl$_3$) δ: 2.27–2.80(m,4H), 3.40–3.57(m,4H), 3.61(s,2H), 3.75–3.88(m,2H), 3.91(s,3H), 3.97(s,6H), 7.22–7.24(m,3H), 7.40(s,5H), 7.64(s,1H), 8.61 (d,1H,J=4.9 Hz)

m/z: 447 [M$^+$].

EXAMPLE 49

Synthesis of N-(4-methoxybenzoyl)-N'-[[2-(3,4,5-trimethoxyphenyl)pyridin-4-yl]methyl]piperazine maleate

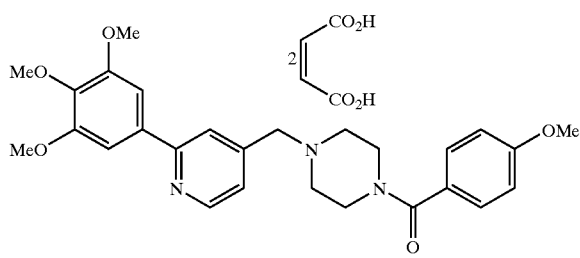

1-[[2-(3,4,5-Trimethoxyphenyl)pyridin-4-yl]methyl]-piperazine (103 mg) and 4-methoxybenzoyl chloride (67 mg) were reacted in the same manner as in Example 46 to obtain the title compound as a maleate.

Yield: 15 mg (8%).

$^1$H-NMR (measured as a free base, 400 MHz, CDCl$_3$) δ: 2.38–2.67(br,4H), 3.60(s,2H), 3.55–3.76(m,4H), 3.83(s,3H), 3.91(s,3H), 3.97(s,6H), 6.91(d,2H,J=8.8 Hz), 7.22–7.23(m,3H), 7.39(d,2H,J=8.8 Hz), 7.63(s,1H), 8.61(d,1H,J=4.9 Hz).

m/z: 477 [M$^+$].

EXAMPLE 50

Synthesis of N-(2,4,6-trichlorobenzoyl)-N'-[[2-(3,4,5-trimethoxyphenyl)pyridin-4-yl]methyl]piperazine hydrochloride

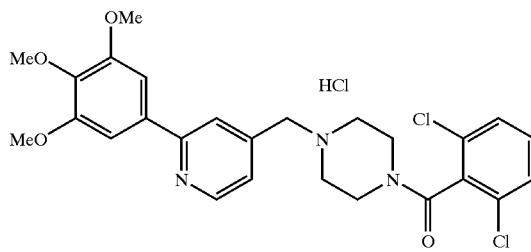

1-[[2-(3,4,5-Trimethoxyphenyl)pyridin-4-yl]methyl]-piperazine (103 mg) and 2,4,6-trichlorobenzoyl chloride (95 mg) were reacted in the same manner as in Example 46 to obtain the title compound as a hydrochloride.

Yield: 29 mg (16%).

$^1$H-NMR (measured as a free base, 400 MHz, CDCl$_3$) δ: 2.49(t,2H,J=5.0 Hz), 2.61(t,2H,J=5.0 Hz), 3.28(t,2H,J=5.0 Hz), 3.61(s,2H), 3.85–3.92(m,2H), 3.91(s,3H), 3.97(s,6H), 7.20–7.25(m,3H), 7.36(s,2H), 7.62(s,1H), 8.60(d,1H,J=4.9 Hz)

m/z: 549 [M$^+$].

EXAMPLE 51

Synthesis of N-(4-bromobenzoyl)-N'-[[2-(3,4,5-trimethoxyphenyl)pyridin-4-yl]methyl]piperazine

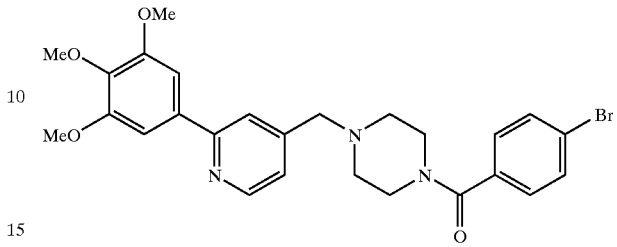

1-[[2-(3,4,5-Trimethoxyphenyl)pyridin-4-yl]methyl]-piperazine (103 mg) and 4-bromobenzoyl chloride (66 mg) were reacted in the same manner as in Example 46 to obtain the title compound as a free base.

Yield: 35 mg (22%).

$^1$H-NMR (measured as a free base, 400 MHz, CDCl$_3$) δ: 3.37(br,8H), 3.86(s,3H), 3.98(s,6H), 4.62(s,2H), 7.41(s,2H), 7.42(d,2H,J=8.6 Hz), 7.66(d,2H,J=6.5 Hz), 8.00(dd,1H,J=5.9 Hz,1.8 Hz), 8.77(s,1H),8.82(d,1H,J=5.9 Hz).

m/z: 526 [M$^+$].

EXAMPLE 52

Synthesis of N-(4-nitrobenzoyl)-N'-[[2-(3,4,5-trimethoxyphenyl)pyridin-4-yl]methyl]piperazine

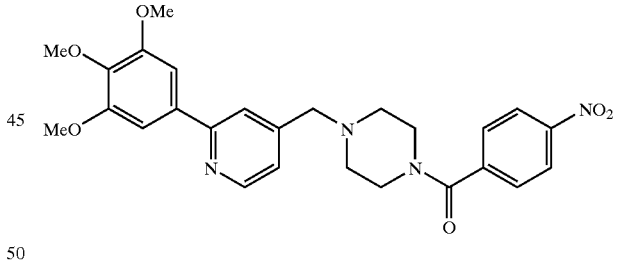

1-[[2-(3,4,5-Trimethoxyphenyl)pyridin-4-yl]methyl]-piperazine (103 mg) and 4-nitrobenzoyl chloride (72 mg) were reacted in the same manner as in Example 46 to obtain the title compound as a free base.

Yield: 76 mg (51%).

$^1$H-NMR (measured as a free base, 400 MHz, CDCl$_3$) δ: 2.35–2.72(m,4H), 3.33–3.48(m,2H), 3.62(s,2H), 3.80–3.89(m,2H), 3.91(s,3H), 3.97(s,6H), 7.21–7.23(m,3H), 7.58(d,2H,J=8.4 Hz), 7.62(s,1H), 8.28(d,2H,J=8.4 Hz), 8.62(d,1H,J=4.9 Hz).

m/z: 492 [M$^+$].

EXAMPLE 53

Synthesis of N-nicotinoyl-N'-[[2-(3,4,5-trimethoxyphenyl)-pyridin-4-yl]methyl]piperazine

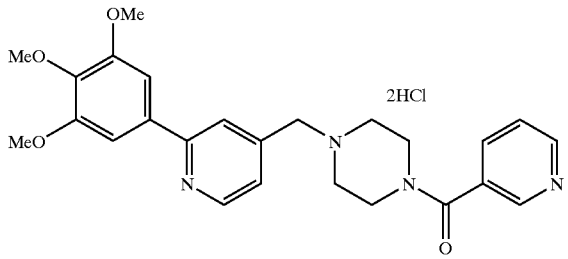

1-[[2-(3,4,5-Trimethoxyphenyl)pyridin-4-yl]methyl]-piperazine (103 mg) and nicotinic acid chloride hydrochloride (70 mg) were reacted in the same manner as in Example 46 to obtain the title compound as a hydrochloride.

Yield: 45 mg (29%).

$^{1}$H-NMR (measured as a free base, 400 MHz, CDCl$_3$) δ: 2.39–2.68(m,4H), 3.41–3.54(m,2H), 3.48(s,2H), 3.77–3.88 (m,2H), 3.91(s,3H), 3.97(s,6H), 7.22–7.25(m,3H), 7.34–7.38(m,1H), 7.63(s,1H), 7.75–7.77(m,1H), 8.62(d,1H, J=5.1 Hz), 8.66(d,1H,J=1.7 Hz), 8.67(s,1H).

m/z: 448 [M$^+$].

EXAMPLE 54

Synthesis of N-(2-naphthoyl)-N'-[[2-(3,4,5-trimethoxyphenyl)pyridin-4-yl]methyl]piperazine

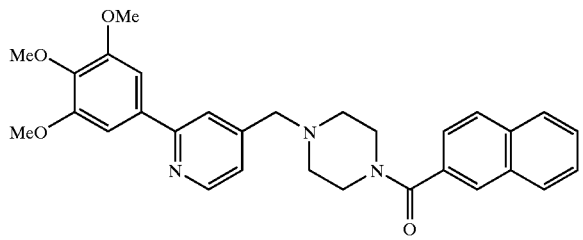

1-[[2-(3,4,5-Trimethoxyphenyl)pyridin-4-yl]methyl]-piperazine (103 mg) and 2-naphthoyl chloride (57 mg) were reacted in the same manner as in Example 46 to obtain the title compound as a free base.

Yield: 21 mg (14%).

$^{1}$H-NMR (measured as a free base, 400 MHz, CDCl$_3$) δ: 2.49 (br,2H), 2.64(br,2H), 3.54(br,4H), 3.68(s,2H), 3.80(s, 3H), 3.92(s,6H), 7.24(s,2H), 7.38(dd,1H,J=5.1 Hz,1.4 Hz), 7.48(dd,1H,J=8.4 Hz,1.8 Hz), 7.52–7.57(m,2H), 7.84(s,1H), 7.88–7.94(m,4H), 8.52(d,1H,J=5.1 Hz).

m/z: 497 [M$^+$].

EXAMPLE 55

Synthesis of N-(4-phenylbenzoyl)-N'-[[2-(3,4,5-trimethoxyphenyl)pyridin-4-yl]methyl]piperazine

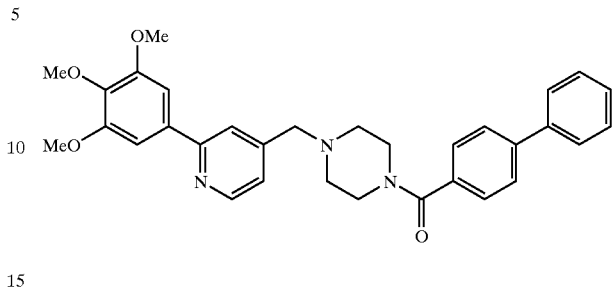

1-[[2-(3,4,5-Trimethoxyphenyl)pyridin-4-yl]methyl]-piperazine (103 mg) and 4-phenylbenzoyl chloride (45 mg) were reacted in the same manner as in Example 46 to obtain the title compound as a free base.

Yield: 78 mg (50%).

$^{1}$H-NMR (measured as a free base, 400 MHz, CDCl$_3$) δ: 2.36–2.72(m,4H), 3.48(br,2H), 3.62(s,2H), 3.82(br,2H), 3.91(s,3H), 3.97(s,6H), 7.24–7.28(m,3H), 7.37–7.39(m,1H), 7.44–7.63(m,9H), 8.62(d,1H,J=5.1 Hz).

m/z: 523 [M$^+$].

Preparation Example 88

Synthesis of 3-(3,4,5-trimethoxyphenyl)benzoic acid

Ethyl 3-(3,4,5-trimethoxyphenyl)benzoate (1.19 g) was treated in the same manner as in Preparation Example 9 to obtain the title compound.

Yield: 986 mg (91%).

EXAMPLE 56

Synthesis of N-[3-(3,4,5-trimethoxyphenyl)benzoyl]-N'-[[2-(3,4,5-trimethoxyphenyl)pyridin-4-yl]methyl]piperazine

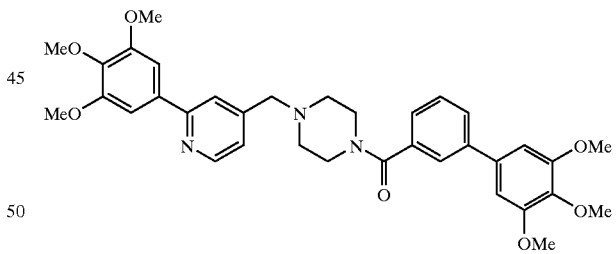

1-[[2-(3,4,5-Trimethoxyphenyl)pyridin-4-yl]methyl]-piperazine (226 mg), 3-(3,4,5-trimethoxyphenyl)benzoic acid (173 mg) and 4-(dimethylamino)pyridine (61 mg) were dissolved in dichloromethane (3 mL), and triethylamine (2.1 μL) was added to the solution. Water-soluble carbodiimide hydrochloride (115 mg) was added to the mixture at 0° C., and the resultant mixture was stirred for 2 hours at 0° C. and overnight at room temperature. The reaction mixture was concentrated under reduced pressure, ethyl acetate was added to the residue, and the resultant mixture was washed with a saturated aqueous solution of sodium hydrogencarbonate and saturated brine, dried over anhydrous sodium sulfate and then concentrated under reduced pressure. The residue was purified by column chromatography on silica gel (chloroform:methanol=40:1) to obtain the title compound as a free base.

Yield: 94 mg (32%).

¹H-NMR (measured as a free base, 400 MHz, CDCl₃) δ: 2.44(br,4H), 2.60(br,4H), 3.61(s,2H), 3.89(s,3H), 3.90(s,3H), 3.92(s,6H), 3.97(s,6H), 6.77(s,2H), 7.22–7.24(m,1H), 7.23(s,2H), 7.46(t,1H,J=3.9 Hz), 7.59–7.62(m,4H), 8.61(d,1H,J=4.9 Hz).

m/z: 613 [M⁺].

EXAMPLE 57

Synthesis of N-[4-(3,4,5-trimethoxyphenyl)benzoyl]-N'-[[2-(3,4,5-trimethoxyphenyl)pyridin-4-yl]methyl]piperazine

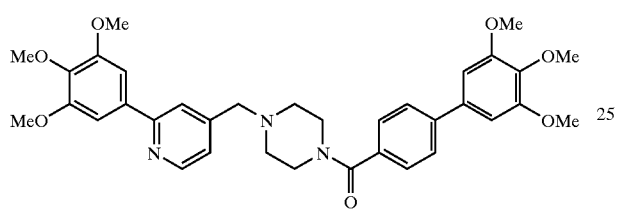

1-[[2-(3,4,5-Trimethoxyphenyl)pyridin-4-yl]methyl]-piperazine (103 mg) was dissolved in dichloromethane (0.9 mL), and a saturated aqueous solution (0.9 mL) of sodium hydrogencarbonate was added to the solution. 4-(3,4,5-Trimethoxyphenyl)benzoyl chloride (55 mg) was then added dropwise to the mixture under ice cooling, and the resultant mixture was stirred for 1 hour. After water was added to the reaction mixture to conduct extraction with chloroform, the resultant organic layer was dried over anhydrous sodium sulfate and concentrated under reduced pressure. The residue was purified by column chromatography on silica gel (chloroform:methanol=50:1) to obtain the title compound as a free base.

Yield: 134 mg (74%).

¹H-NMR (measured as a free base, 400 MHz, CDCl₃) δ: 2.49–2.59(m,4H), 3.55–3.58(m,2H), 3.62(s,2H), 3.80–3.88(m,2H), 3.90(s,3H), 3.91(s,3H), 3.92(s,6H), 4.00(s,6H), 6.77(s,2H), 7.23–7.24(m,3H), 7.48(d,2H,J=8.1 Hz), 7.59(d,2H,J=4.9 Hz), 7.64(s,1H), 8.62(d,1H,J=4.9 Hz).

m/z: 613 [M⁺].

Preparation Example 89

Synthesis of 2-(3,4,5-trimethoxyphenyl)isonicotinic acid

Ethyl 2-(3,4,5-trimethoxyphenyl)isonicotinate (3.17 g) was treated in the same manner as in Preparation Example 9 to obtain the title compound.

Yield: 2.60 g (90%).

EXAMPLE 58

Synthesis of N-[2-(3,4,5-trimethoxyphenyl)isonicotinoyl]-N'-[[2-(3,4,5-trimethoxyphenyl)pyridin-4-yl]methyl]-piperazine

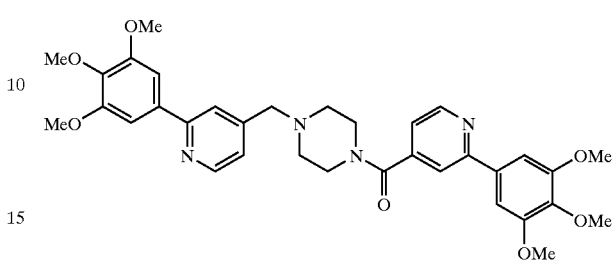

1-[[2-(3,4,5-Trimethoxyphenyl)pyridin-4-yl]methyl]-piperazine (160 mg) and 2-(3,4,5-trimethoxyphenyl)-isonicotinic acid (113 mg) were reacted in the same manner as in Example 56 to obtain the title compound as a free base.

Yield: 111 mg (47%).

¹H-NMR (measured as a free base, 400 MHz, CDCl₃) δ: 2.40–2.52(m,2H), 2.57–2.67(m,2H), 3.40–3.51(m,2H), 3.62(s,2H), 3.83–3.87(m,2H), 3.90(s,3H), 3.91(s,3H), 3.96(s,6H), 3.97(s,6H), 7.17(d,1H,J=4.8 Hz), 7.20–7.35(m,5H), 7.63(s,1H), 7.69(s,1H), 8.62(d,1H,J=5.1 Hz), 8.72(d,1H,J=4.9 Hz).

m/z: 614 [M⁺].

EXAMPLE 59

Synthesis of N-cinnamoyl-N'-[[2-(3,4,5-trimethoxyphenyl)-pyridin-4-yl]methyl]piperazine

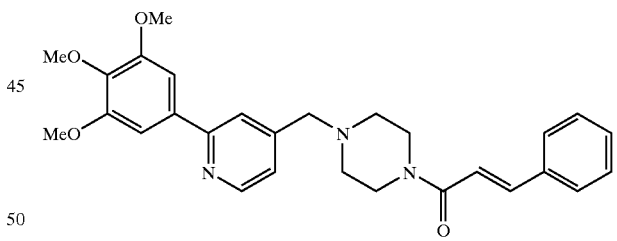

1-[[2-(3,4,5-Trimethoxyphenyl)pyridin-4-yl]methyl]-piperazine (103 mg) and cinnamoyl chloride (65 mg) were reacted in the same manner as in Example 46 to obtain the title compound as a free base.

Yield: 94 mg (66%).

¹H-NMR (measured as a free base, 400 MHz, CDCl₃) δ: 2.48–2.61(m,4H), 3.48(br,2H), 3.61(s,2H), 3.63–3.83(m,2H), 3.91(s,3H), 3.98(s,6H), 6.87(d,1H,J=15.4 Hz), 7.23–7.27(m,3H), 7.36–7.37(m,3H), 7.51–7.53(m,2H), 7.65–7.70(s,2H), 8.63(d,1H,J=4.9 Hz).

m/z: 473 [M⁺].

EXAMPLE 60

Synthesis of N-(3,4,5-trimethoxycinnamoyl)-N'-[[2-(3,4,5-trimethoxyphenyl)pyridin-4-yl]methyl] piperazine

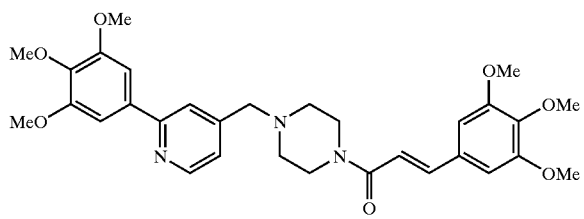

1-[[2-(3,4,5-Trimethoxyphenyl)pyridin-4-yl]methyl]-piperazine (103 mg) and 3,4,5-trimethoxycinnamic acid (65 mg) were reacted in the same manner as in Example 56 to obtain the title compound as a free base.

Yield: 59 mg (53%).

$^1$H-NMR (measured as a free base, 400 MHz, CDCl$_3$) δ: 2.55 (m, 4H), 3.62(s,2H), 3.67–3.85(m,4H), 3.87(s,3H), 3.89(s,6H), 3.91(s,3H), 3.98(s,6H), 6.72(s,2H), 6.73(d,1H, J=15.4 Hz), 7.22–7.35(m,3H), 7.61(d,1H,J=15.4 Hz), 7.64 (s,1H), 8.63(d,1H,J=5.1 Hz)

m/z: 563 [M$^+$].

EXAMPLE 61

Synthesis of N-(2,3,4-trimethoxycinnamoyl)-N'-[[2-(3,4,5-trimethoxyphenyl)pyridin-4-yl]methyl] piperazine

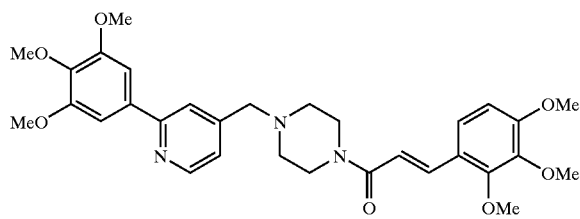

1-[[2-(3,4,5-Trimethoxyphenyl)pyridin-4-yl]methyl]-piperazine (103 mg) and 2,3,4-trimethoxycinnamic acid (65 mg) were reacted in the same manner as in Example 56 to obtain the title compound as a free base.

Yield: 97 mg (59%).

$^1$H-NMR (measured as a free base, 400 MHz, CDCl$_3$) δ: 2.53 (s, 4H), 3.61(s,2H), 3.64–3.84(m,4H), 3.87(s,3H), 3.88 (s,3H), 3.90(s,3H), 3.91(s,3H), 4.00(s,6H), 6.67(d,1H,J=8.8 Hz), 6.92(d,1H,J=15.6 Hz), 7.21(d,1H,J=8.6 Hz), 7.23–7.35 (m,3H), 7.65(s,1H), 7.80(d,1H,J=15.4 Hz), 8.62(d,1H,J=5.1 Hz).

m/z: 563 [M$^+$].

Test Example 1
(Inhibitory Effect on Cell Adhesion)

This test was conducted by reference to the method of Ross et al. (J. Biol. Chem., 267, 8537–8543 (1992)). More specifically, after human umbilical venous endothelial cells (HUVEC) were cultured on a 48-well plate to confluent growth, IL-1β or TNFα was added thereto. Upon elapsed time of 5 hours after the addition, U937, which is a human monocytic/histocytic cell fluorescence-labeled with PKH2 (product of Dainippon Pharmaceutical Co., Ltd.), was added in a proportion of 1×10$^6$ cells per well. After the plate was left at rest at room temperature for 1 hour, unadhered U937 was washed out and lysed in 1% Triton X-100 to measure a remaining fluorescence intensity (excitation wavelength: 480 nm; measuring wavelength: 530 nm). HUVEC and U937 were cultured in EGM-2 (product of Sanko Junyaku K.K.) and 10% FCS-containing RPMI1640, respectively. Each test agent was added to HUVEC upon the addition of IL-1β or TNFα and to U937 24 hours prior to the cell adhesion test. The inhibitory activity was calculated out according to the equation [100−(C−B)/(A−B)×100(%)], wherein A is the number of U937 cells adhered to HUVEC stimulated by IL-1β or TNFα when no test agent was added, B is the number of U937 cells adhered to HUVEC not stimulated by IL-1β or TNFα when no test agent was added, and C is the number of U937 cells adhered to HUVEC stimulated by IL-1β or TNFα when the test agent was added. The results are shown in Table 1. As control compounds, Test Compound 1 described in Japanese Patent Application Laid-Open No. 9-143075 and dilazep described in Japanese Patent Application Laid-Open No. 11-92382 were simultaneously evaluated.

TABLE 1

Inhibitory activity of each compound at 1 μM against cell adhesion

| | Percent inhibition (%) | |
|---|---|---|
| Example | Stimulation by TNFα | Stimulation by IL-1β |
| 18 | 54 | 37 |
| 19 | 58 | 33 |
| 21 | 60 | 44 |
| 25 | 70 | 78 |
| 26 | 69 | 75 |
| 37 | 56 | 68 |
| 38 | 76 | 59 |
| 40 | 55 | 44 |
| 41 | 67 | 56 |
| 42 | 56 | 54 |
| 56 | 52 | 76 |
| Test compound 1 | 5 | 10 |
| Dilazep | 12 | 0 |

Specific formulation examples will hereinafter be described.

| Preparation Example 90 (Capsule preparation) | |
|---|---|
| N-[(E)-5-(3,4,5-trimethoxyphenyl)-4-pentenyl]-N'-[[2-(3,4,5-trimethoxyphenyl)pyridin-4-yl]methyl]piperazine difumarate | 30 mg |
| Microcrystalline cellulose | 30 mg |
| Lactose | 30 mg |
| Magnesium stearate | 3 mg |
| Total amount | 93 mg. |

The above ingredients were mixed in accordance with a method known per se in the art and then charged in a gelatin capsule to obtain a capsule preparation.

| Preparation Example 91: (Tablet preparation) | |
|---|---|
| N-[(E)-5-(3,4,5-trimethoxyphenyl)-4-pentenyl]-N'-[[2-(3,4,5-trimethoxyphenyl)pyridin-4-yl]methyl]piperazine difumarate | 30 mg |
| Starch | 44 mg |

-continued

Preparation Example 91: (Tablet preparation)

| | |
|---|---|
| Starch (for glue) | 5.6 mg |
| Magnesium stearate | 0.4 mg |
| Calcium carboxymethyl cellulose | 20 mg |
| Total amount | 100 mg. |

The above ingredients were mixed in accordance with a method known per se in the art to obtain a tablet preparation.

Preparation Example 92
(Injection Preparation)

N-[(E)-5-(3,4,5-Trimethoxyphenyl)-4-pentenyl]-N'-[[2-(3,4,5-trimethoxyphenyl)pyridin-4-yl]methyl]piperazine difumarate (100 mg) and sodium chloride (900 mg) were dissolved in distilled water (about 80 mL) for injection, and distilled water for injection was added to the resultant solution to 100 mL in total. This diluted solution was sterilized by filtration and then subdivided and charged into 10 light-screening ampoules, and the ampoules were sealed to obtain sterile injection preparations.

As described above, the compounds (1) according to the present invention have inhibitory effects on both cell adhesion and cell infiltration and are useful for prevention or treatment of diseases such as allergy, asthma, rheumatism, arteriosclerosis and inflammation.

Obviously, numerous modifications of the above teachings are apparent to those skilled in the art. Therefore, within the scope of the appended claims, the invention may be practiced otherwise than as specifically described herein.

What is claimed is:

1. A cyclic diamine compound of formula (1):

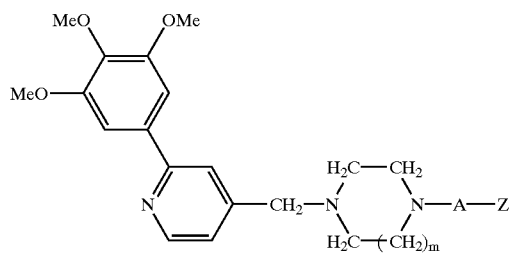

wherein

A is $(CH_2)_n$, $(CH_2)_n$—CH=CH, CO—$(CH_2)_n$ or CO—$(CH_2)_n$—CH=CH, in which n is a number of 0 to 3; Z represents a formula (2) or (3):

(2)

(3)

in which $R^1$, $R^2$, $R^4$, $R^5$ and $R^6$ are individually a hydrogen atom, alkyl group, alkoxy group, halogen atom or nitro group; $R^3$ is a hydrogen atom, alkyl group, alkoxy group, halogen atom, nitro group, naphthyl group, or phenyl group optionally substituted by 1 to 3 substituents selected from the group consisting of alkyl groups, alkoxy groups, halogen atoms, a nitro group and a phenyl group; and X and Y are individually CH or a nitrogen atom; and m is 1 or 2;

an acid-addition salt thereof, or a hydrate thereof.

2. The cyclic diamine compound of claim 1, wherein $R^1$, $R^2$, $R^4$, $R^5$ and $R^6$ are individually a hydrogen atom, $C_1$–$C_6$-alkyl group, $C_1$–$C_6$-alkoxy group, halogen atom or nitro group; and $R^3$ is a hydrogen atom, $C_1$–$C_6$-alkyl group, $C_1$–$C_6$-alkoxy group, halogen atom, nitro group, naphthyl group, or phenyl group optionally substituted by 1 to 3 substituents selected from $C_1$–$C_6$-alkyl groups, $C_1$–$C_6$-alkoxy groups, halogen atoms and a phenyl group.

3. The cyclic diamine compound of claim 1, wherein said cyclic diamine compound is N-[3-(3,4,5-trimethoxyphenyl)benzyl]-N'-[[2-(3,4,5-trimethoxyphenyl)pyridin-4-yl]methyl]piperazine.

4. The cyclic diamine compound of claim 1, wherein said cyclic diamine compound is N-[3-(3,4,5-trimethoxyphenyl)benzyl]-N'-[[2-(3,4,5-trimethoxyphenyl)pyridin-4-yl]methyl]homopiperazine.

5. The cyclic diamine compound of claim 1, wherein said cyclic diamine compound is N-[(2-phenylpyridin-4-yl)methyl]-N'-[[2-(3,4,5-trimethoxyphenyl)pyridin-4-yl]methyl]piperazine.

6. The cyclic diamine compound of claim 1, wherein said cyclic diamine compound is N-[[2-(4-methoxyphenyl)pyridin-4-yl]methyl]-N'-[[2-(3,4,5-trimethoxyphenyl)pyridin-4-yl]methyl]-piperazine.

7. The cyclic diamine compound of claim 1, wherein said cyclic diamine compound is N-[[2-(3,4-dimethoxyphenyl)pyridin-4-yl]methyl]-N'-[[2-(3,4,5-trimethoxyphenyl)pyridin-4-yl]methyl]piperazine.

8. The cyclic diamine compound of claim 1, wherein said cyclic diamine compound is N-[2-(5,6,7-trimethoxynaphthalen-2-yl)ethyl]-N'-[[2-(3,4,5-trimethoxyphenyl)pyridin-4-yl]methyl]-piperazine.

9. The cyclic diamine compound of claim 1, wherein said cyclic diamine compound is N-[(5,6,7-trimethoxynaphthalen-2-yl)methyl]-N'-[[2-(3,4,5-trimethoxyphenyl)pyridin-4-yl]methyl]-piperazine.

10. The cyclic diamine compound of claim 1, wherein said cyclic diamine compound is N-[(E)-5-(3,4,5-trimethoxyphenyl)-4-pentenyl]-N'-[[2-(3,4,5-trimethoxyphenyl)pyridin-4-yl]methyl]piperazine.

11. The cyclic diamine compound of claim 1, wherein said cyclic diamine compound is N-[(E)-5-(3,4,5-trimethoxyphenyl)-4-pentenyl]-N'-[[2-(3,4,5-trimethoxyphenyl)pyridin-4-yl]methyl]homopiperazine.

12. The cyclic diamine compound of claim 1, wherein said cyclic diamine compound is N-[(E)-5-(4-fluorophenyl)-4-pentenyl]-N'-[[2-(3,4,5-trimethoxyphenyl)pyridin-4-yl]methyl]piperazine.

13. The cyclic diamine compound of claim 1, wherein said cyclic diamine compound is N-[3-(3,4,5-trimethoxyphenyl)benzoyl]-N'-[[2-(3,4,5-trimethoxyphenyl)pyridin-4-yl]methyl]piperazine.

14. A pharmaceutical composition comprising, as an active ingredient, a cyclic diamine compound of formula (1):

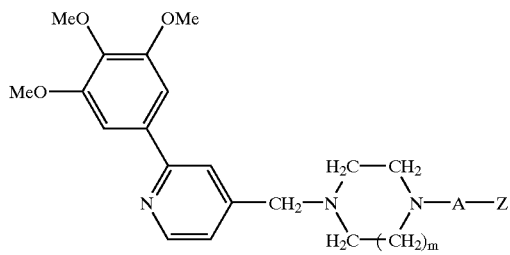

(1)

wherein

A is $(CH_2)_n$, $(CH_2)_n$—CH=CH, CO—$(CH_2)_n$ or CO—$(CH_2)_n$—CH=CH, in which n is a number of 0 to 3; Z represents a formula (2) or (3):

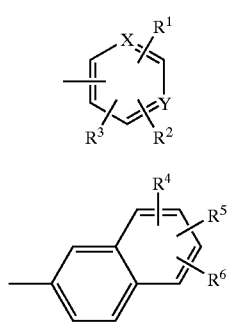

(2)

(3)

in which $R^1$, $R^2$, $R^4$, $R^5$ and $R^6$ are individually a hydrogen atom, alkyl group, alkoxy group, halogen atom or nitro group; $R^3$ is a hydrogen atom, alkyl group, alkoxy group, halogen atom, nitro group, naphthyl group, or phenyl group optionally substituted by 1 to 3 substituents selected from the group consisting of alkyl groups, alkoxy groups, halogen atoms, a nitro group and a phenyl group; and X and Y are individually CH or a nitrogen atom; and m is 1 or 2; an acid-addition salt thereof, or a hydrate thereof.

15. The pharmaceutical composition of claim 14, wherein $R^1$, $R^2$, $R^4$, $R^5$ are individually a hydrogen atom, $C_1$–$C_6$-alkyl group, $C_1$–$C_6$-alkoxy group, halogen atom or nitro group; and $R^3$ is a hydrogen atom, $C_1$–$C_6$-alkyl group, $C_1$–$C_6$-alkoxy group, halogen atom, nitro group, naphthyl group, or phenyl group optionally substituted by 1 to 3 substituents selected from $C_1$–$C_6$-alkyl groups, $C_1$–$C_6$-alkoxy groups, halogen atoms and a phenyl group.

16. The pharmaceutical composition of claim 14, comprising an effective amount of said cyclic diamine compound for treating a disease caused by cell adhesion and/or cell infiltration.

17. The pharmaceutical composition of claim 14, wherein said cyclic diamine compound is N-[3-(3,4,5-trimethoxyphenyl)benzyl]-N'-[[2-(3,4,5-trimethoxyphenyl)pyridin-4-yl]m ethyl]piperazine.

18. The pharmaceutical composition of claim 14, wherein said cyclic di amine compound is N-[3-(3,4,5-trimethoxyphenyl)benzyl]-N'-[[2-(3,4,5-trimethoxyphenyl)pyridin-4-yl]methyl]homopiperazine.

19. The pharmaceutical composition of claim 14, wherein said cyclic diamine compound is N-[(2-phenylpyridin-4-yl)methyl]-N'-[[2-(3,4,5-trimethoxyphenyl)pyridin-4-yl]methyl]piperazine.

20. The pharmaceutical composition of claim 14, wherein said cyclic diamine compound is N-[[2-(4-methoxyphenyl) pyridin-4-yl]methyl]-N'-[[2-(3,4,5-trimethoxyphenyl) pyridin-4-yl]methyl]-piperazine.

21. The pharmaceutical composition of claim 14, wherein said cyclic diamine compound is N-[[2-(3,4-dimethoxyphenyl)pyridin-4-yl]methyl]-N'-[[2-(3,4,5-trimethoxyphenyl)pyridin-4-yl]methyl]piperazine.

22. The pharmaceutical composition of claim 14, wherein said cyclic diamine compound is N-[2-(5,6,7-trimethoxynaphthalen-2-yl)ethyl]-N'-[[2-(3,4,5-trimethoxyphenyl)pyridin-4-yl]methyl]-piperazine.

23. The pharmaceutical composition of claim 14, wherein said cyclic diamine compound is N-[(5,6,7-trimethoxyhaphthalen-2-yl)methyl]-N'-[[2-(3,4,5-trimethoxyphenyl)pyridin-4-yl]methyl]-piperazine.

24. The pharmaceutical composition of claim 14, wherein said cyclic diamine compound is N-[(E)-5-(3,4,5-trimethoxyphenyl)-4-pentenyl]-N'-[[2-(3,4,5-trimethoxyphenyl)pyridin-4-yl]methyl]piperazine.

25. The pharmaceutical composition of claim 14, wherein said cyclic diamine compound is N-[(E)-5-(3,4,5-trimethoxyphenyl)-4-pentenyl]-N'-[[2-(3,4,5-trimethoxyphenyl)pyridin-4-yl]methyl]homopiperazine.

26. The pharmaceutical composition of claim 14, wherein said cyclic diamine compound is N-[(E)-5-(4-fluorophenyl)-4-pentenyl]-N'-[[2-(3,4,5-trimethoxyphenyl)pyridin-4-yl]methyl]piperazine.

27. The pharmaceutical composition of claim 14, wherein said cyclic diamine compound is N-[3-(3,4,5-trimethoxyphenyl)benzoyl]-N'-[[2-(3,4,5-trimethoxyphenyl)pyridin-4-yl]methyl]piperazine.

28. A method for treating a disease caused by cell adhesion and/or cell infiltration, which comprises administering to a patient in need thereof an effective amount of a cyclic diamine compound of formula (1):

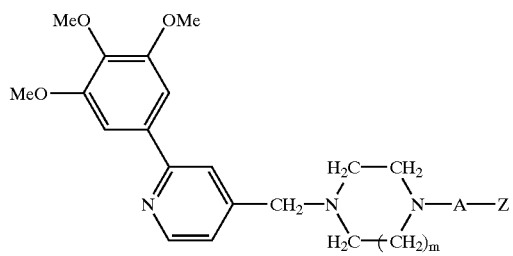

(1)

wherein

A is $(CH_2)_n$, $(CH_2)_n$—CH=CH, CO—$(CH_2)_n$ or CO—$(CH_2)_n$—CH=CH, in which n is a number of of 0 to 3; Z represents a formula (2) or (3):

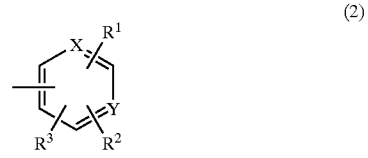

(2)

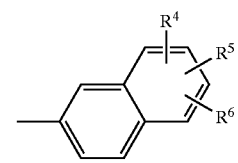

(3)

in which $R^1$, $R^2$, $R^4$, $R^5$ and $R^6$ are individually a hydrogen atom, alkyl group, alkoxy group, halogen atom or nitro group; R3 is a hydrogen atom, alkyl group, alkoxy group, halogen atom, nitro group, naphthyl group, or phenyl group optionally substituted by 1 to 3 substituents selected from the group consisting of alkyl groups, alkoxy groups, halogen atoms, a nitro group and a phenyl group; and X and Y are individually CH or a nitrogen atom; and m is 1 or 2;

an acid-addition salt thereof, or a hydrate thereof.

29. The method of claim 28, wherein $R^1$, $R^2$, $R^4$, $R^5$ and $R^6$ are individually a hydrogen atom, $C_1$–$C_6$-alkyl group, $C_1$–$C_6$-alkoxy group, halogen atom or nitro group; and $R^3$ is a hydrogen atom, $C_1$–$C_6$-alkyl group, $C_1$–$C_6$-alkoxy group, halogen atom, nitro group, naphthyl group, or phenyl group optionally substituted by 1 to 3 substituents selected from $C_1$–$C_6$-alkyl groups, $C_1$–$C_6$-alkoxy groups, halogen atoms and a phenyl group.

30. The method according to claim 28, wherein the disease is selected from the group consisting of allergy, asthma, inflammation, rheumatism and arteriosclerosis.

31. The method according to claim 28, wherein said cyclic diamine compound is N-[3-(3,4,5-trimethoxyphenyl)benzyl]-N'-[[2-(3,4,5-trimethoxyphenyl)pyridin-4-yl]methyl]piperazine.

32. The method according to claim 28, wherein said cyclic diamine compound is N-[3-(3,4,5-trimethoxyphenyl)benzyl]-N'-[[2-(3,4,5-trimethoxyphenyl)pyridin-4-yl]methyl]homopiperazine.

33. The method according to claim 28, wherein said cyclic diamine compound is N-[(2-phenylpyridin-4-yl)methyl]-N'-[[2-(3,4,5-trimethoxyphenyl)pyridin-4-yl]methyl]piperazine.

34. The method according to claim 28, wherein said cyclic diamine compound is N-[[2-(4-methoxyphenyl)pyridin-4-yl]methyl]-N'-[[2-(3,4,5-trimethoxyphenyl)pyridin-4-yl]methyl]-piperazine.

35. The method according to claim 28, wherein said cyclic diamine compound is N-[[2-(3,4-dimethoxyphenyl)pyridin-4-yl]methyl]-N'-[[2-(3,4,5-trimethoxyphenyl)pyridin-4-yl]methyl]piperazine.

36. The method according to claim 28, wherein said cyclic diamine compound is N-[2-(5,6,7-trimethoxynaphthalen-2-yl)ethyl]-N'-[[2-(3,4,5-trimethoxyphenyl)pyridin-4-yl]methyl]-piperazine.

37. The method according to claim 28, wherein said cyclic diamine compound is N-[(5,6,7-trimethoxynaphthalen-2-yl)methyl]-N'-[[2-(3,4,5-trimethoxyphenyl)pyridin-4-yl]methyl]-piperazine.

38. The method according to claim 28, wherein said cyclic diamine compound is N-[(E)-5-(3,4,5-trimethoxyphenyl)-4-pentenyl]-N'-[[2-(3,4,5-trimethoxyphenyl)pyridin-4-yl]methyl]piperazine.

39. The method according to claim 28, wherein said cyclic diamine compound is N-[(E)-5-(3,4,5-trimethoxyphenyl)-4-pentenyl]-N'-[[2-(3,4,5-trimethoxyphenyl)pyridin-4-yl]methyl]homopiperazine.

40. The method according to claim 28, wherein said cyclic diamine compound is N-[(E)-5-(4-fluorophenyl)-4-pentenyl]-N'-[[2-(3,4,5-trimethoxyphenyl)pyridin-4-yl]methty]piperazine.

41. The method according to claim 28, wherein said cyclic diamine compound is N-[3-(3,4,5-trimethoxyphenyl)benzoyl]-N'-[[2-(3,4,5-trimethoxyphenyl)pyridin-4-yl]methyl]piperazine.

* * * * *

UNITED STATES PATENT AND TRADEMARK OFFICE
CERTIFICATE OF CORRECTION

PATENT NO. : 6,552,188 B2
DATED : April 22, 2003
INVENTOR(S) : Tatsuhiko Kodama et al.

It is certified that error appears in the above-identified patent and that said Letters Patent is hereby corrected as shown below:

Column 53,
First formula

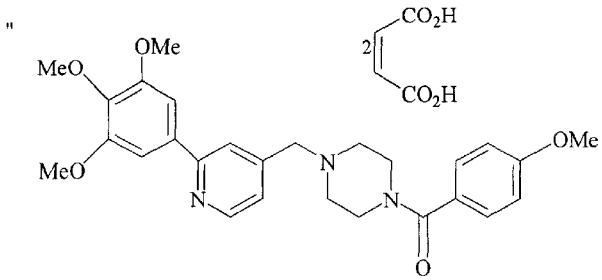

should read

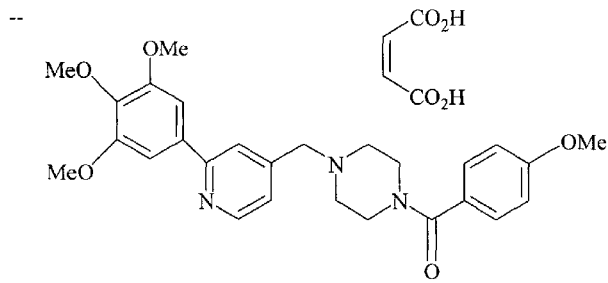

Signed and Sealed this

Twentieth Day of January, 2004

JON W. DUDAS
*Acting Director of the United States Patent and Trademark Office*